(12) United States Patent
Zeng et al.

(10) Patent No.: US 9,190,620 B2
(45) Date of Patent: Nov. 17, 2015

(54) ORGANIC ELECTROLUMINESCENT MATERIALS AND DEVICES

(71) Applicant: Universal Display Corporation, Ewing, NJ (US)

(72) Inventors: Lichang Zeng, Lawrenceville, NJ (US); Suman Layek, Lawrenceville, NJ (US); Harvey Wendt, Medford Lakes, NJ (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 17 days.

(21) Appl. No.: 14/194,689

(22) Filed: Mar. 1, 2014

(65) Prior Publication Data

US 2015/0249221 A1    Sep. 3, 2015

(51) Int. Cl.
*H01L 51/50*    (2006.01)
*H01L 51/00*    (2006.01)
*C07D 333/76*    (2006.01)
*C07D 409/04*    (2006.01)

(52) U.S. Cl.
CPC .......... *H01L 51/0074* (2013.01); *C07D 333/76* (2013.01); *C07D 409/04* (2013.01); *H01L 51/005* (2013.01); *H01L 51/0054* (2013.01); *H01L 51/0072* (2013.01); *H01L 51/5016* (2013.01); *H01L 51/5024* (2013.01); *H01L 51/5076* (2013.01); *H01L 51/5096* (2013.01)

(58) Field of Classification Search
USPC .................. 257/50, 52; 428/690; 252/519.21
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Michael Lebentritt
(74) *Attorney, Agent, or Firm* — Duane Morris LLP

(57) ABSTRACT

A novel compound containing terphenylene connected to dibenzothiophene, dibenzofuran or dibenzoselenophene that can be used as hosts in phosphorescent organic light-emitting device is disclosed.

21 Claims, 3 Drawing Sheets

(56) References Cited

U.S. PATENT DOCUMENTS

| | | | |
|---|---|---|---|
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0151042 | A1 | 8/2003 | Hueschen |
| 2003/0152802 | A1 | 8/2003 | Tsuboyama et al. |
| 2003/0165713 | A1* | 9/2003 | Oguma et al. ............ 428/690 |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Prakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2012/0012833 | A1* | 1/2012 | Shirasawa et al. ............ 257/40 |
| 2012/0199820 | A1* | 8/2012 | Ito et al. ............ 257/40 |
| 2014/0225085 | A1* | 8/2014 | Hayashi et al. ............ 257/40 |
| 2014/0332792 | A1* | 11/2014 | Tada et al. ............ 257/40 |
| 2015/0014649 | A1* | 1/2015 | Ma et al. ............ 257/40 |
| 2015/0053939 | A1* | 2/2015 | Adamovich et al. ............ 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 200215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2012133644 A1 | 10/2012 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiciiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

(56) References Cited

OTHER PUBLICATIONS

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).

Huang, Wei-Sheng et al., "Highly Phosphorescent Bis-Cyclometalated Iridium Complexes Containing Benzoimidazole-Based Ligands," Chem. Mater, 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett, 77(15)2280-2282 (2000).

Lo, Shih-Chun et al., "Blue Phosphorescence from Iridium(111) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergard et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett, 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner formula (I)

formula (II)

formula (III)

ORGANIC ELECTROLUMINESCENT MATERIALS AND DEVICES

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to organic materials used in such devices. More specifically, the present invention relates to host compounds for phosphorescent OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

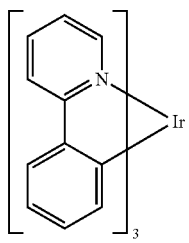

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

The present disclosure provides novel compounds containing terphenylene connected to dibenzothiophene, dibenzofuran or dibenzoselenophene that can be used as hosts in phosphorescent organic light-emitting device.

According to an embodiment of the present disclosure, a novel compound having a formula (I),

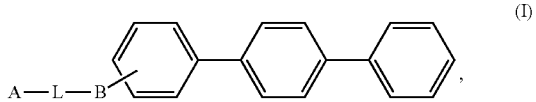

is disclosed where

A is selected from a group consisting of triphenylene, phenanthrene, anthracene, biphenyl, terphenyl, carbazole, dibenzothiophene, dibenzofuran, dibenzoselenophene, fluorene, azatriphenylene, azacarbazole, azadibenzothiophene, azadibenzofuran, azadibenzoselenophene, triazine, or combinations thereof;

wherein L is selected from a group consisting of a direct bond, benzene, biphenyl and terphenyl, pyridine, or combinations thereof, and wherein L is optionally further substituted with alkyl, halogen, hydrogen, deuterium, nitrile or aryl;

wherein B is selected from a group consisting of dibenzothiophene, dibenzofuran and dibenzoselenophene; and wherein A and B are independently optionally further substituted with one or more substituents selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, and for each of A and B, two adjacent substituents are optionally joined to form a ring.

According to an aspect of the present disclosure, a device comprising a phosphorescent organic light-emitting device is disclosed. The phosphorescent organic light-emitting device comprising: an anode; a cathode; and an organic layer, disposed between the anode and the cathode, comprising the novel compound of the formula (I). A formulation comprising the novel compound is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al, "Very high-efficiency green organic light-emitting devices based on electrophosphorescence," Appl. Phys. Lett., vol, 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
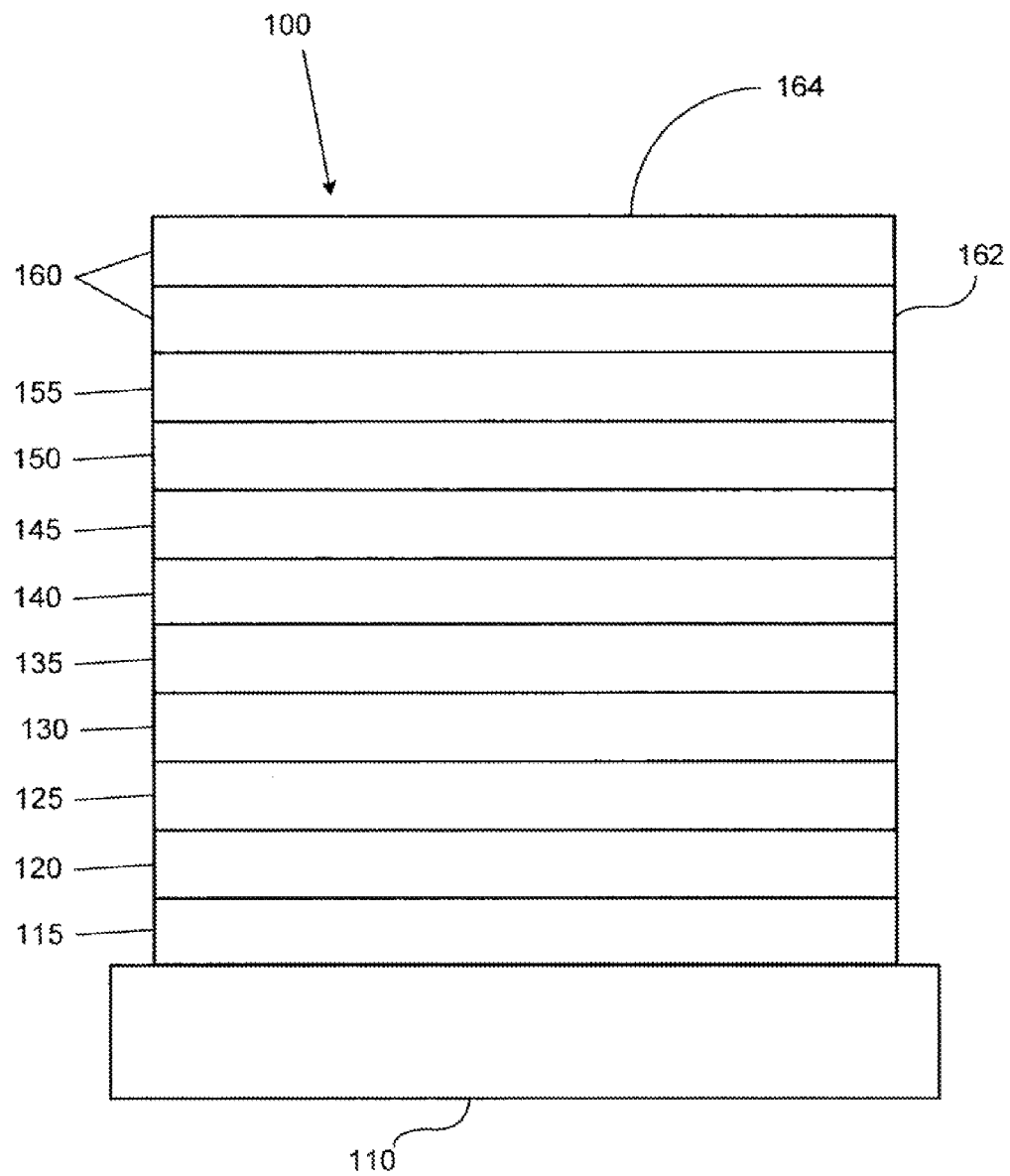
FIG. 1 shows an organic light emitting device that can incorporate the inventive compound disclosed herein.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
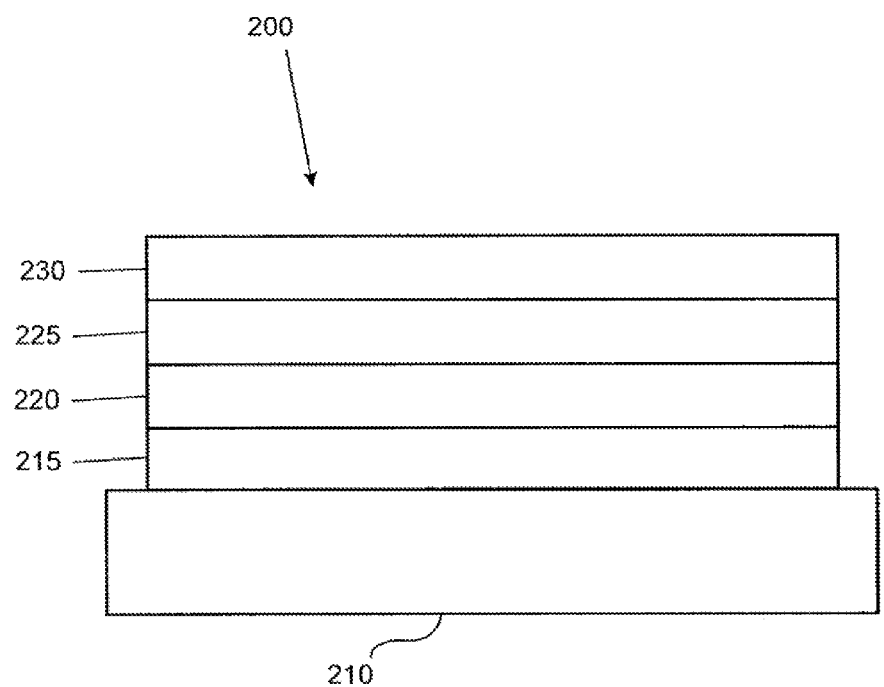
FIG. 2 shows an inverted organic light emitting device that can incorporate the inventive compound disclosed herein.
Figure 3:
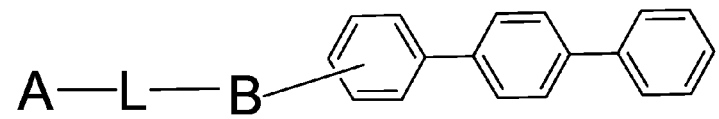
FIG. 3 shows the formulas (I), (II), and (III) representing the inventive compound.
Figure 3:
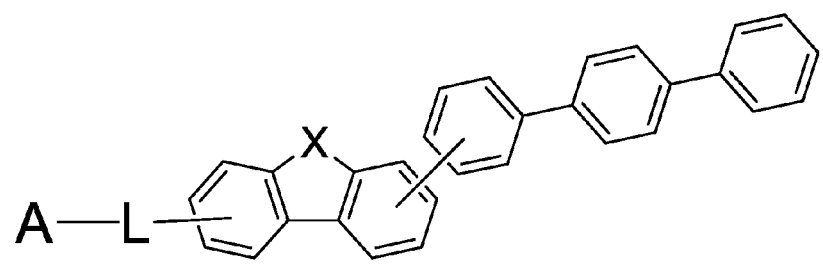
Figure 3:
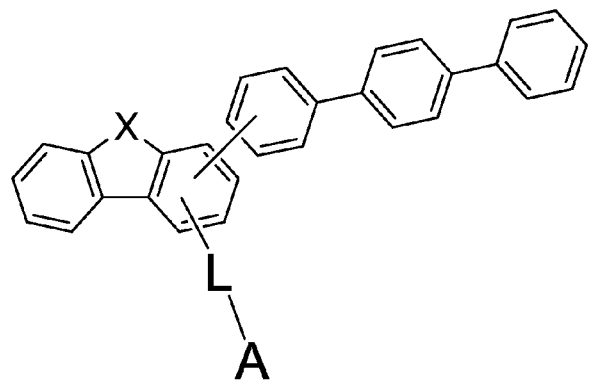

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et at., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

Compounds consisting of various building blocks have been reported as organic electroluminescent materials. Depending on the unique ways individual building blocks are connected, these compounds have different energy levels, molecular packing and charge-transport properties, all of which heavily affect device performance. The present disclosure discloses a new class of compounds containing terphenylene connected to dibenzothiophene, dibenzofuran or dibenzoselenophene. Unexpectedly, phosphorescent OLED devices using these invented compounds as host materials demonstrate superior performance compared to the compounds reported in the literature.

According to an embodiment of the present disclosure, a novel compound having a formula (I),

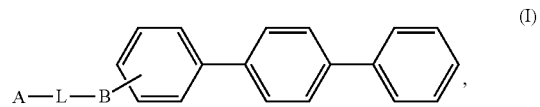

(I)

is disclosed. In the formula (I),

A is selected from a group consisting of triphenylene, phenanthrene, anthracene, biphenyl, terphenyl, carbazole, dibenzothiophene, dibenzofuran, dibenzoselenophene, fluorene, azatriphenylene, azacarbazole, azadibenzothiophene, azadibenzofuran, azadibenzoselenophene, triazine, or combinations thereof;

wherein L is selected from a group consisting of a direct bond, benzene, biphenyl and terphenyl, pyridine, or combinations thereof, and wherein L is optionally further substituted with alkyl, halogen, hydrogen, deuterium, nitrile or aryl;

wherein B is selected from a group consisting of dibenzothiophene, dibenzofuran and dibenzoselenophene; and wherein A and B are independently optionally further substituted with one or more substituents selected from the group consisting of deuterium, halide, alkyl, cycloalkyl, heteroalkyl, arylalkyl, alkoxy, aryloxy, amino, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, and for each of A and B, two adjacent substituents are optionally joined to form a ring.

According to an embodiment, the compound having the formula (I) can be further defined as having formula (II) or (III)

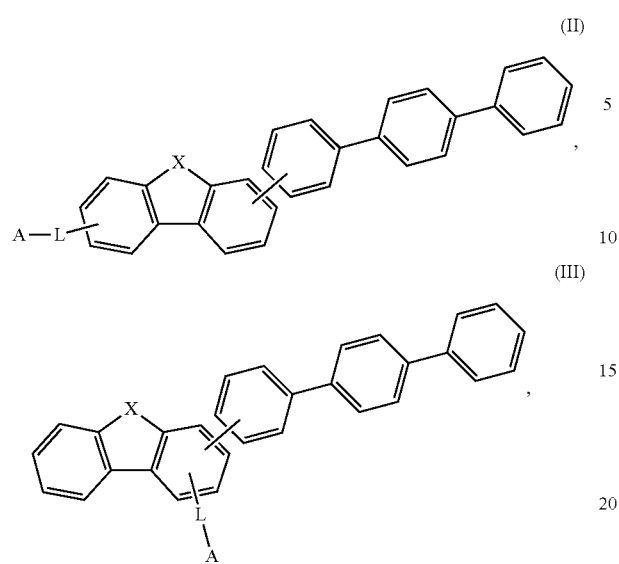
wherein X is selected from a group consisting of O, S and Se.
In one embodiment of the present disclosure, A in the formulas (I), (II), and (III) is selected from the group consisting of
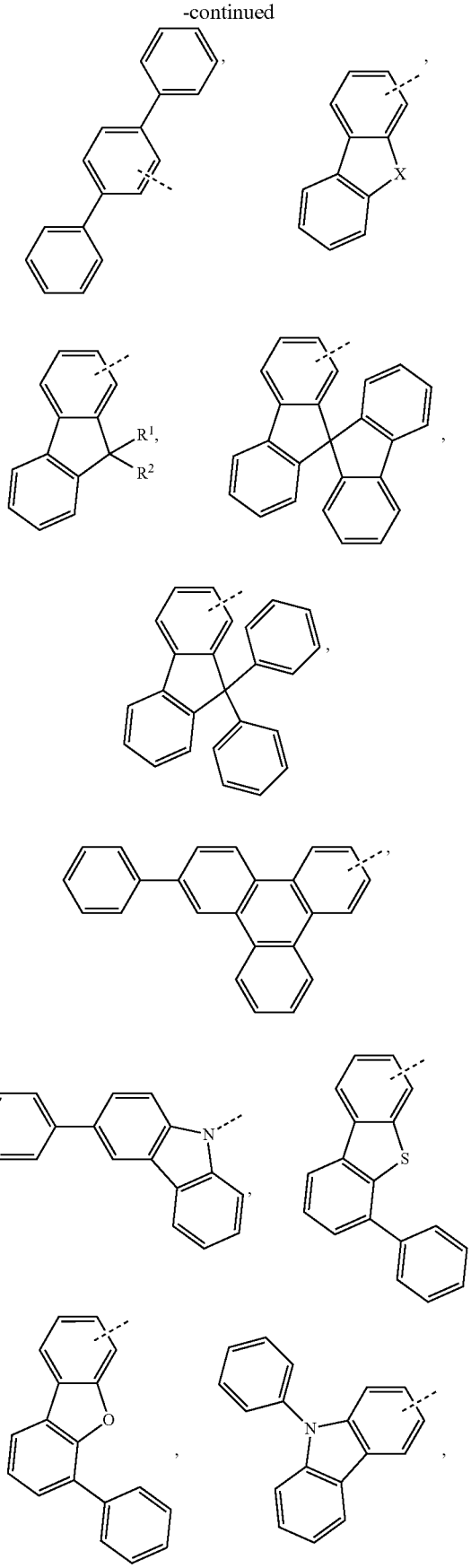

-continued
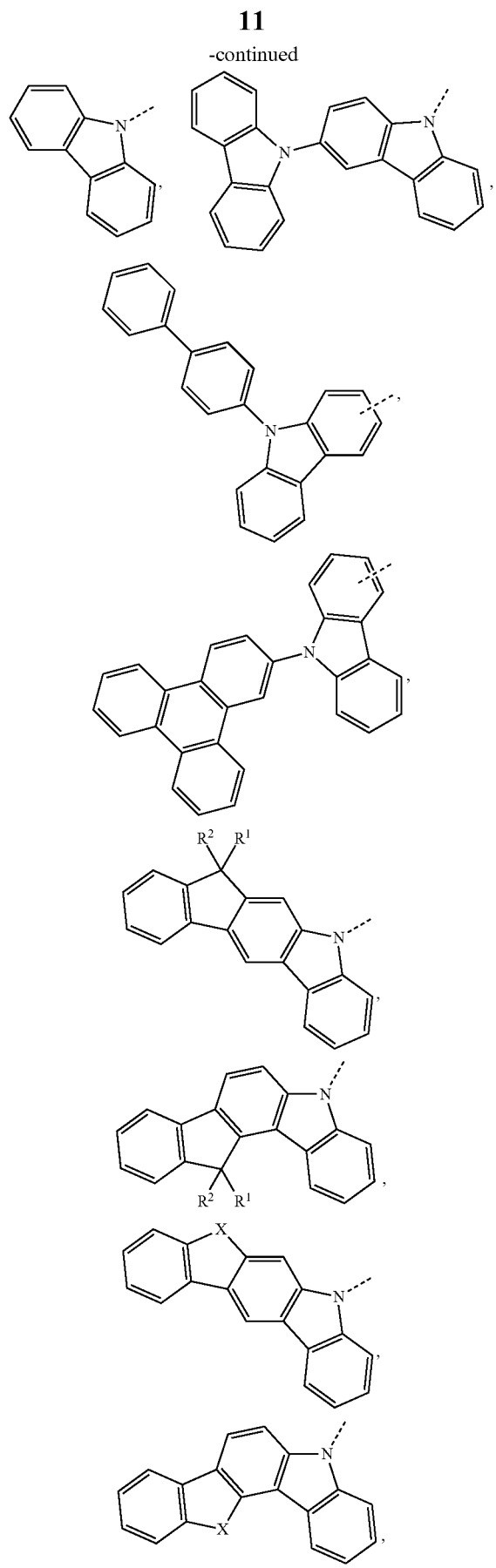
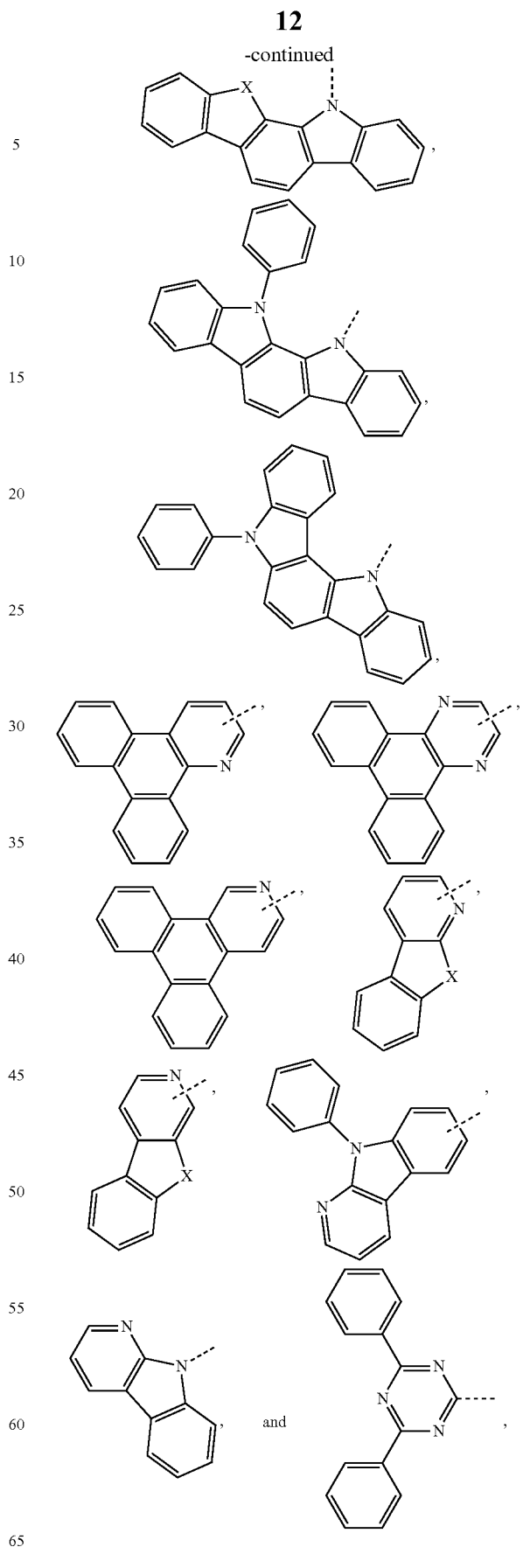
wherein X is S, O or Se; and $R^1$ and $R^2$ are, independently, linear or branched alkyl with 1 to 12 carbon atoms, and $R^1$ and $R^2$ are optionally jointed to form a ring.

In the formula (I), B is selected from the group consisting of

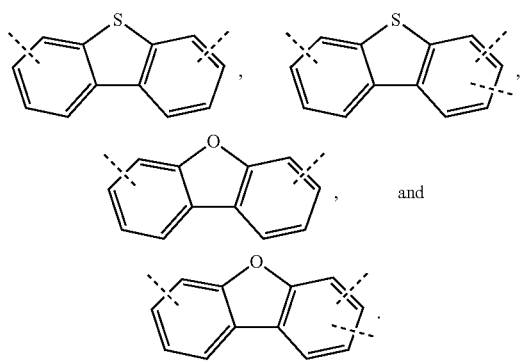

and

L in the formulas (I), (II), and (III) is selected from the group consisting of a direct bond,

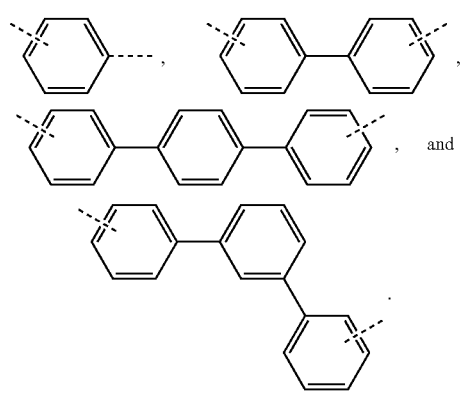

and

According to an embodiment, the compound having the formula (I) is selected from the group consisting of

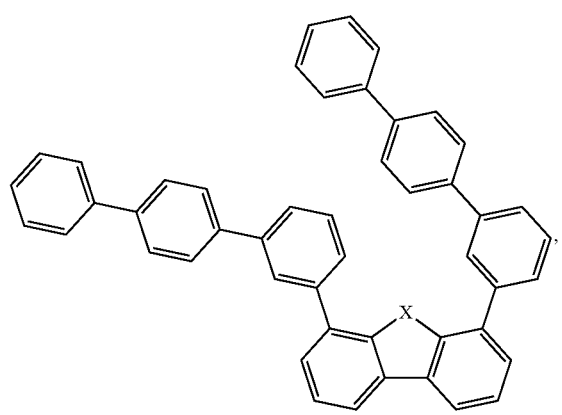

Compound 1, wherein X=O,
Compound 2, wherein X=S,
Compound 3, wherein X=Se,

-continued

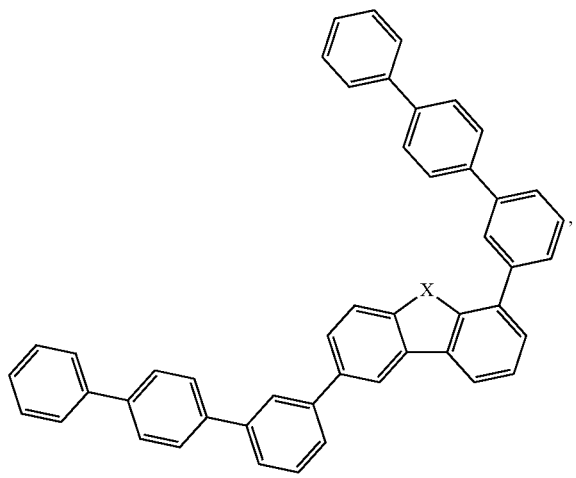

Compound 4, wherein X=O,
Compound 5, wherein X=S,
Compound 6, wherein X=Se,

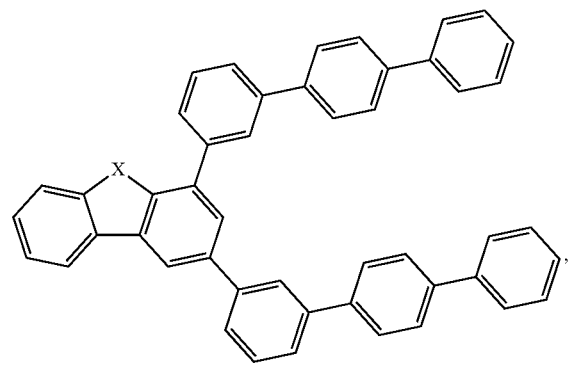

Compound 7, wherein X=O,
Compound 8, wherein X=S,
Compound 9, wherein X=Se,

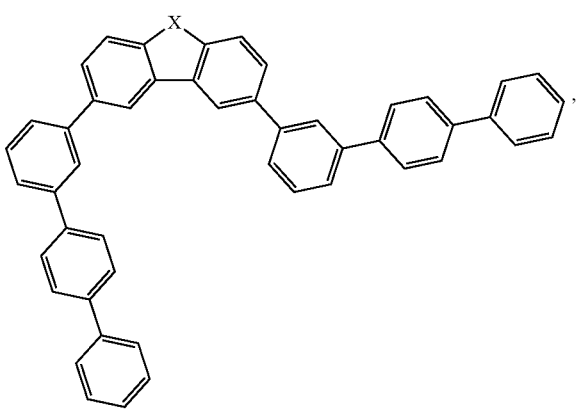

Compound 10, wherein X=O,
Compound 11, wherein X=S,
Compound 12, wherein X=Se,

-continued

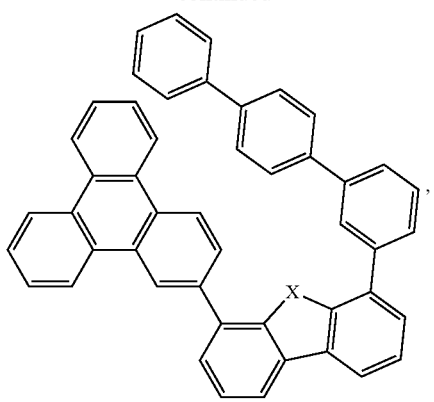

Compound 13, wherein X=O,
Compound 14, wherein X=S,
Compound 15, wherein X=Se,

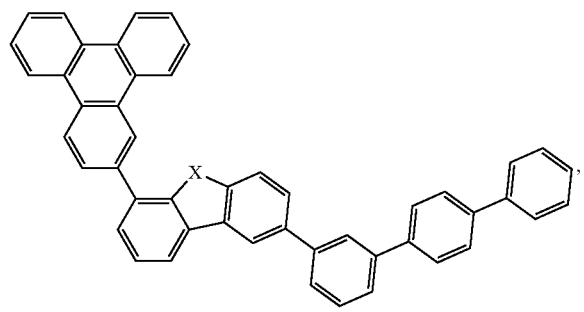

Compound 16, wherein X=O,
Compound 17, wherein X=S,
Compound 18, wherein X=Se,

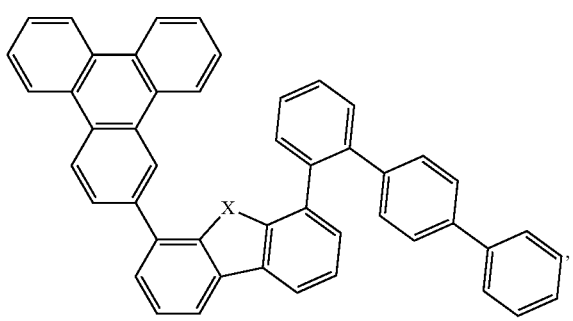

Compound 19, wherein X=O,
Compound 20, wherein X=S,
Compound 21, wherein X=Se,

-continued

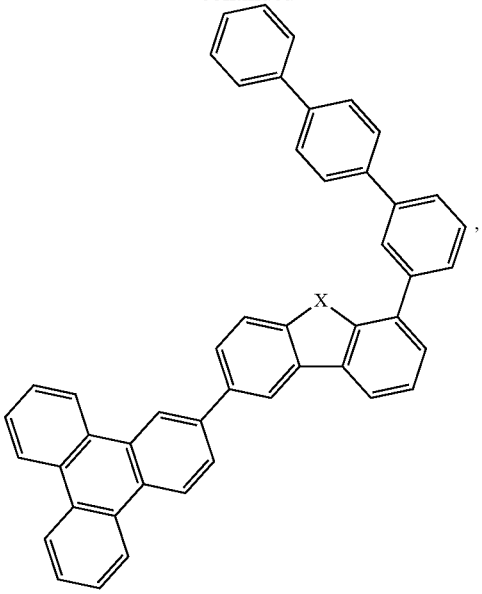

Compound 22, wherein X=O,
Compound 23, wherein X=S,
Compound 24, wherein X=Se,

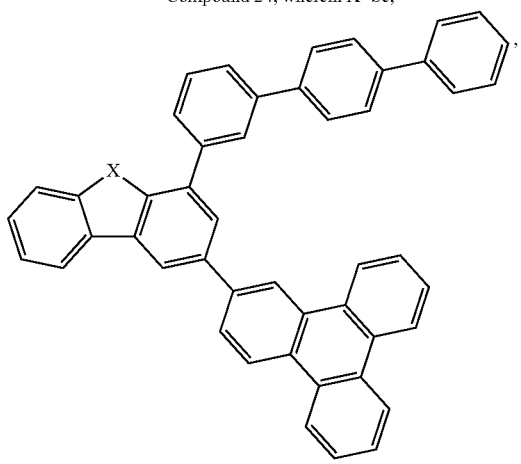

Compound 25, wherein X=O,
Compound 26, wherein X=S,
Compound 27, wherein X=Se,

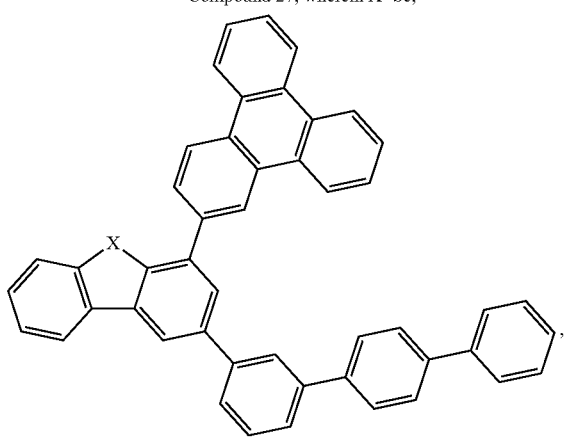

Compound 28, wherein X=O,
Compound 29, wherein X=S,
Compound 30, wherein X=Se,

-continued

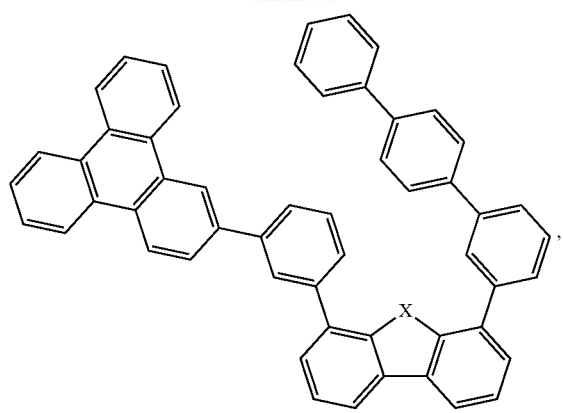

Compound 31, wherein X=O,
Compound 32, wherein X=S,
Compound 33, wherein X=Se,

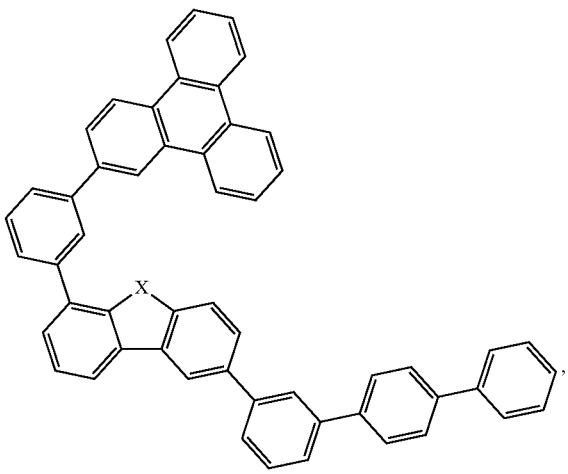

Compound 34, wherein X=O,
Compound 35, wherein X=S,
Compound 36, wherein X=Se,

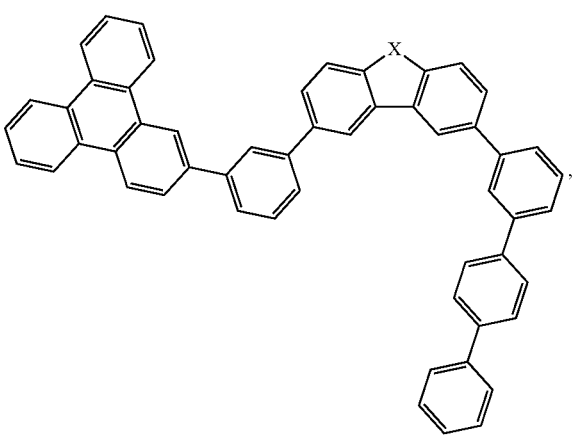

Compound 37, wherein X=O,
Compound 38, wherein X=S,
Compound 39, wherein X=Se,

-continued

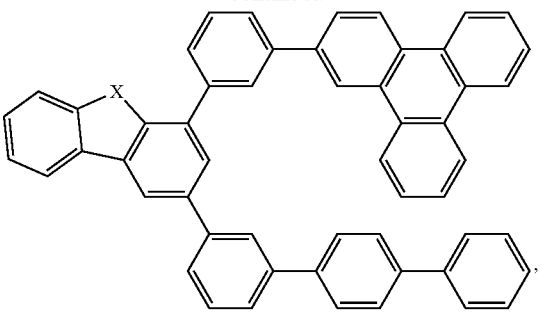

Compound 40, wherein X=O,
Compound 41, wherein X=S,
Compound 42, wherein X=Se,

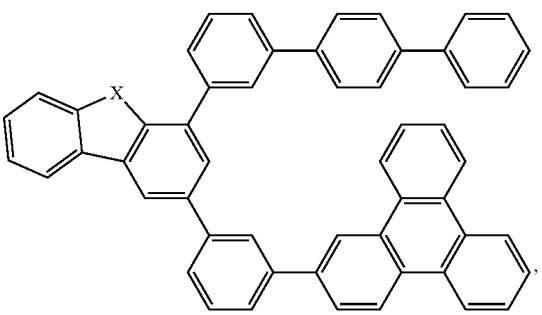

Compound 43, wherein X=O,
Compound 44, wherein X=S,
Compound 45, wherein X=Se,

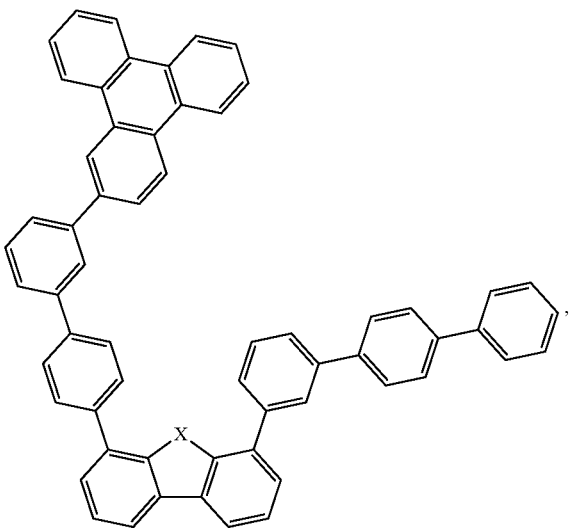

Compound 46, wherein X=O,
Compound 47, wherein X=S,
Compound 48, wherein X=Se,

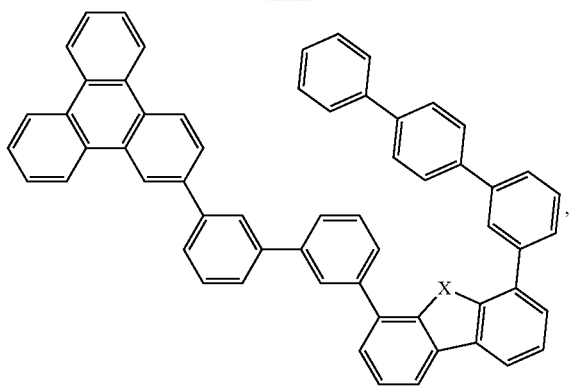

Compound 49, wherein X=O,
Compound 50, wherein X=S,
Compound 51, wherein X=Se,

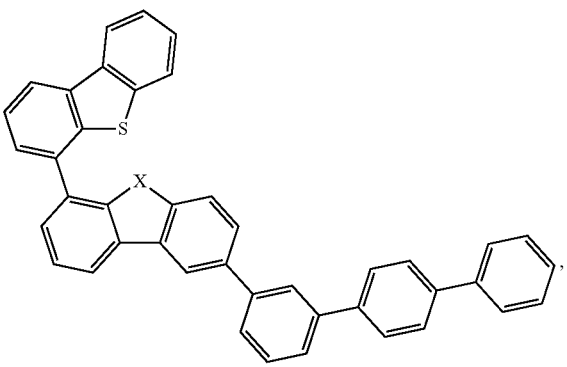

Compound 58, wherein X=O,
Compound 59, wherein X=S,
Compound 60, wherein X=Se,

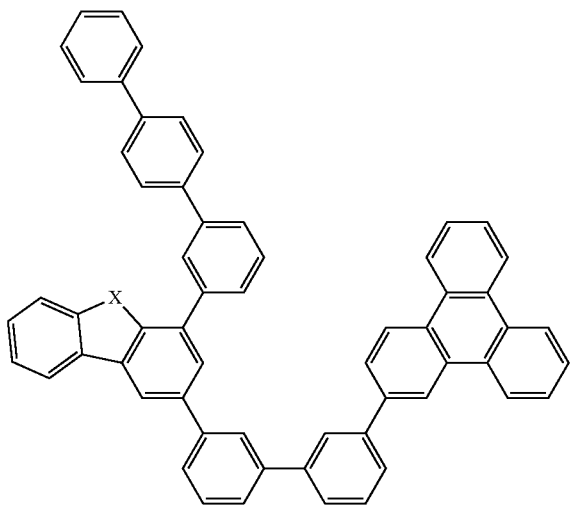

Compound 52, wherein X=O,
Compound 53, wherein X=S,
Compound 54, wherein X=Se,

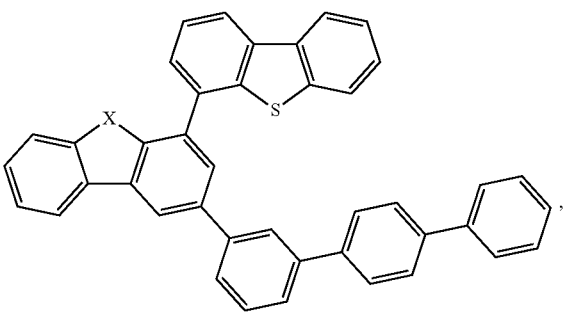

Compound 61, wherein X=O,
Compound 62, wherein X=S,
Compound 63, wherein X=Se,

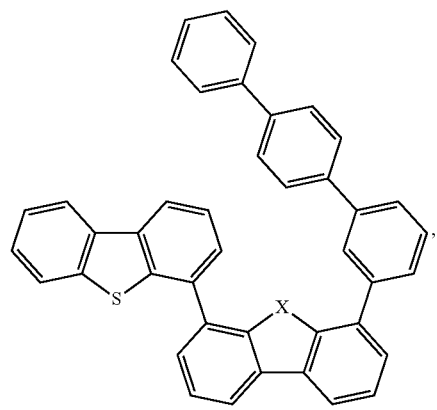

Compound 55, wherein X=O,
Compound 56, wherein X=S,
Compound 57, wherein X=Se,

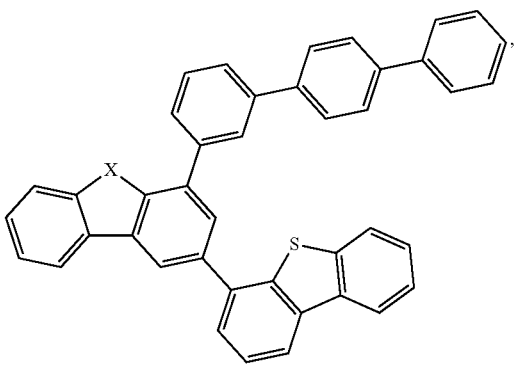

Compound 64, wherein X=O,
Compound 65, wherein X=S,
Compound 66, wherein X=Se,

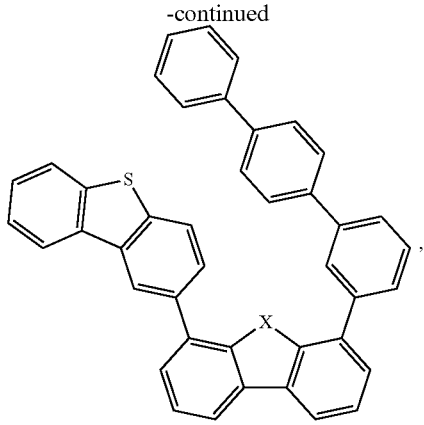

Compound 67, wherein X=O,
Compound 68, wherein X=S,
Compound 69, wherein X=Se,

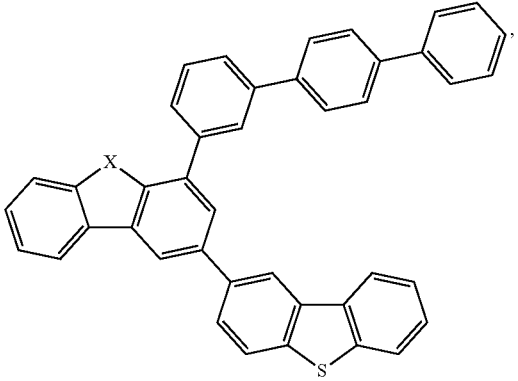

Compound 76, wherein X=O,
Compound 77, wherein X=S,
Compound 78, wherein X=Se,

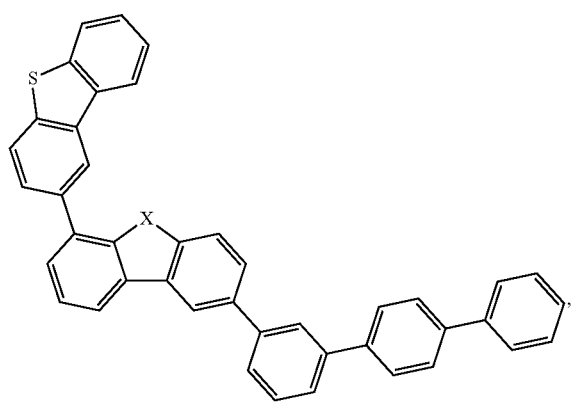

Compound 70, wherein X=O,
Compound 71, wherein X=S,
Compound 72, wherein X=Se,

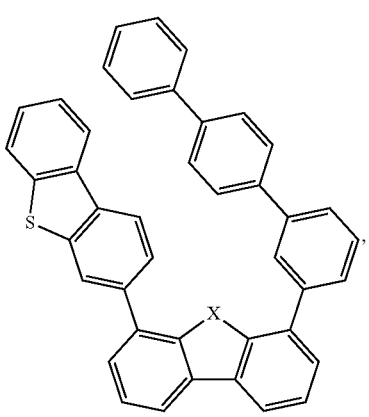

Compound 79, wherein X=O,
Compound 80, wherein X=S,
Compound 81, wherein X=Se,

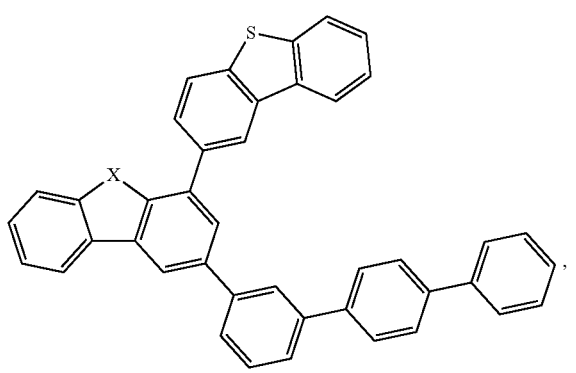

Compound 73, wherein X=O,
Compound 74, wherein X=S,
Compound 75, wherein X=Se,

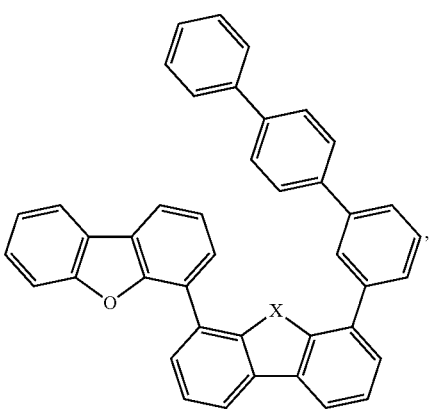

Compound 82, wherein X=O,
Compound 83, wherein X=S,
Compound 84, wherein X=Se,

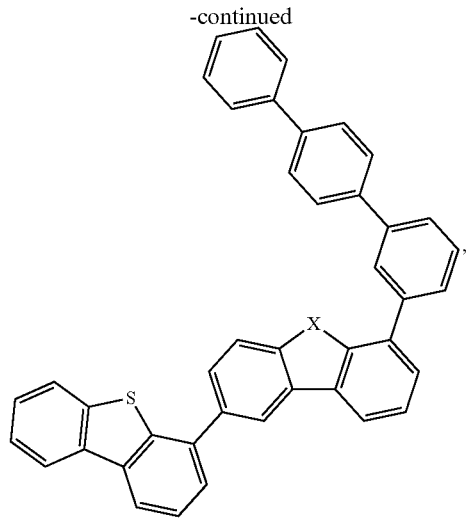

Compound 85, wherein X=O,
Compound 86, wherein X=S,
Compound 87, wherein X=Se,

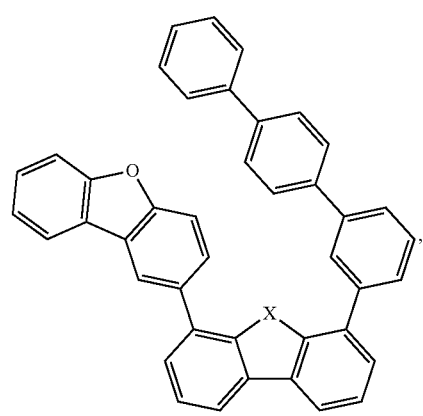

Compound 88, wherein X=O,
Compound 89, wherein X=S,
Compound 90, wherein X=Se,

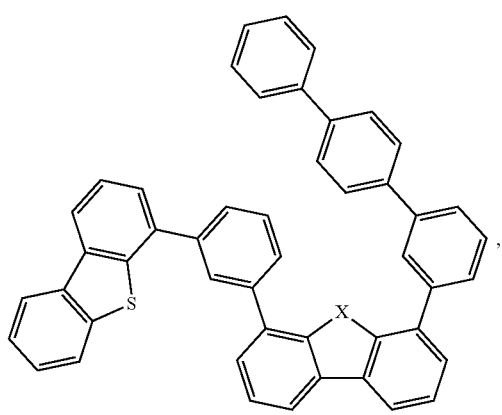

Compound 91, wherein X=O,
Compound 92, wherein X=S,
Compound 93, wherein X=Se,

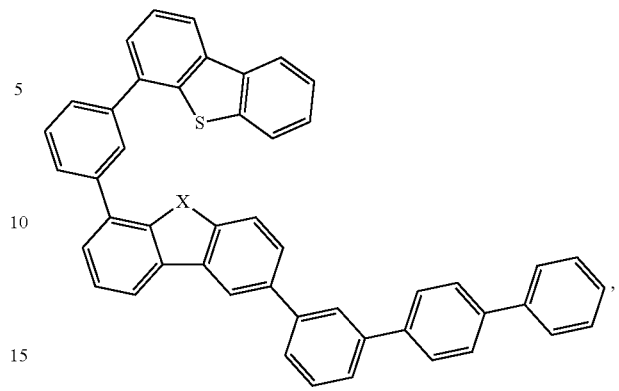

Compound 94, wherein X=O,
Compound 95, wherein X=S,
Compound 96, wherein X=Se,

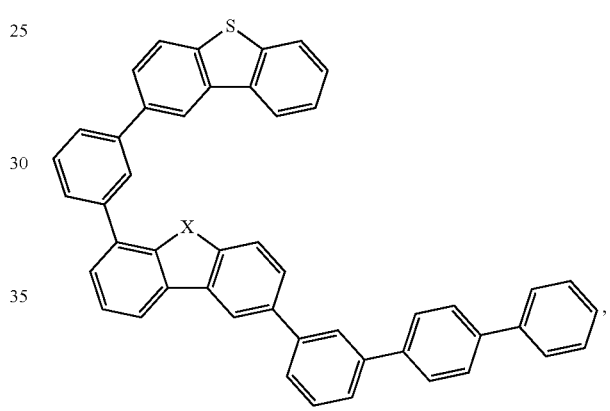

Compound 97, wherein X=O,
Compound 98, wherein X=S,
Compound 99, wherein X=Se,

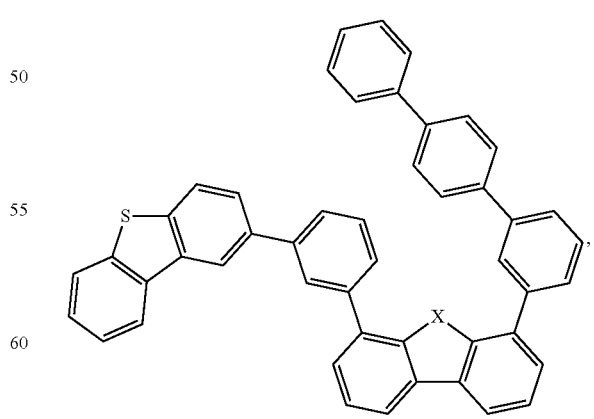

Compound 100, wherein X=O,
Compound 101, wherein X=S,
Compound 102, wherein X=Se,

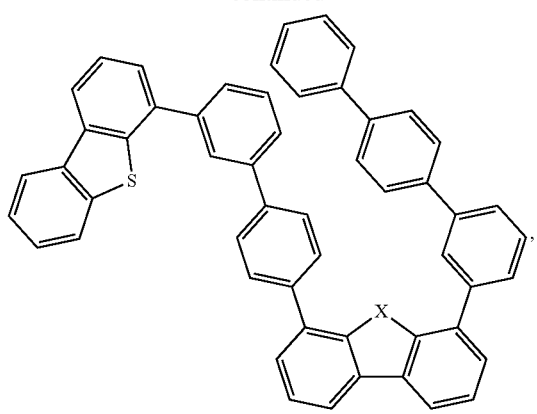

Compound 103, wherein X=O,
Compound 104, wherein X=S,
Compound 105, wherein X=Se,

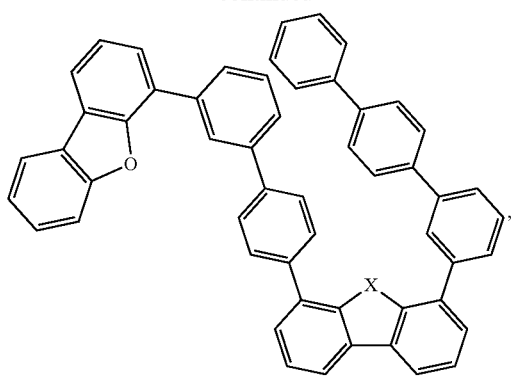

Compound 112, wherein X=O,
Compound 113, wherein X=S,
Compound 114, wherein X=Se, Compound 106, wherein X=O,
Compound 107, wherein X=S,
Compound 108, wherein X=Se, Compound 115, wherein X=O,
Compound 116, wherein X=S,
Compound 117, wherein X=Se, Compound 109, wherein X=O,
Compound 110, wherein X=S,
Compound 111, wherein X=Se, Compound 118, wherein X=O,
Compound 119, wherein X=S,
Compound 120, wherein X=Se,

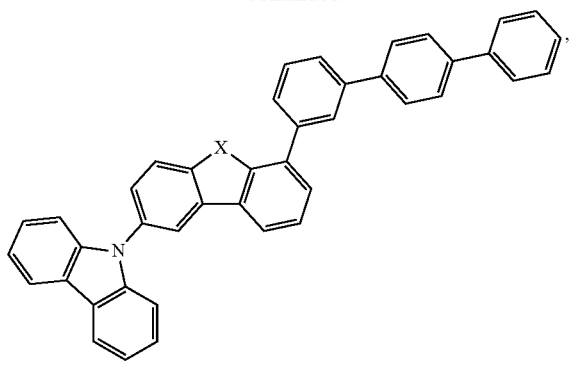

Compound 121, wherein X=O,
Compound 122, wherein X=S,
Compound 123, wherein X=Se,

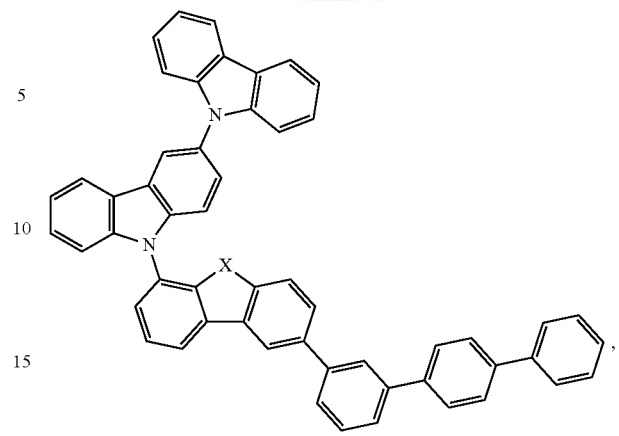

Compound 130, wherein X=O,
Compound 131, wherein X=S,
Compound 132, wherein X=Se,

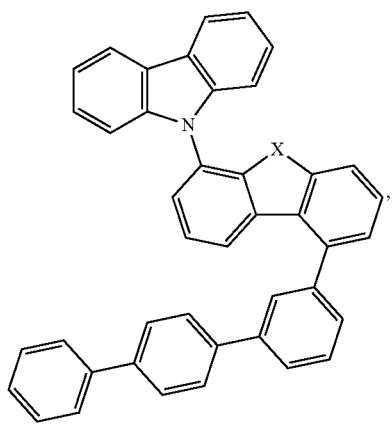

Compound 124, wherein X=O,
Compound 125, wherein X=S,
Compound 126, wherein X=Se,

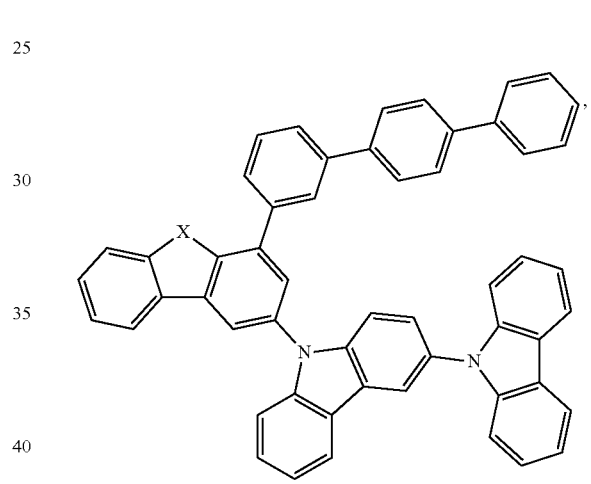

Compound 133, wherein X=O,
Compound 134, wherein X=S,
Compound 135, wherein X=Se,

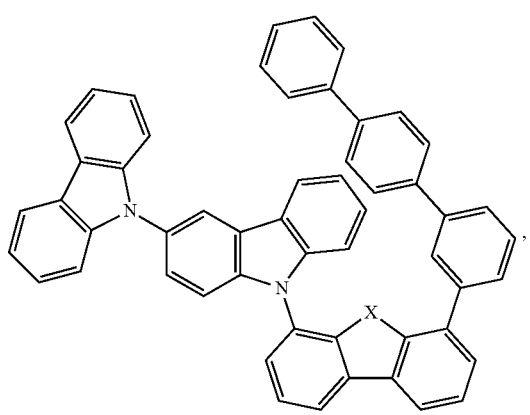

Compound 127, wherein X=O,
Compound 128, wherein X=S,
Compound 129, wherein X=Se,

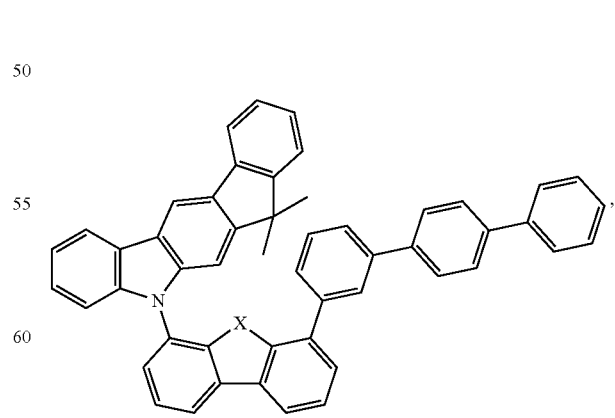

Compound 136, wherein X=O,
Compound 137, wherein X=S,
Compound 138, wherein X=Se,

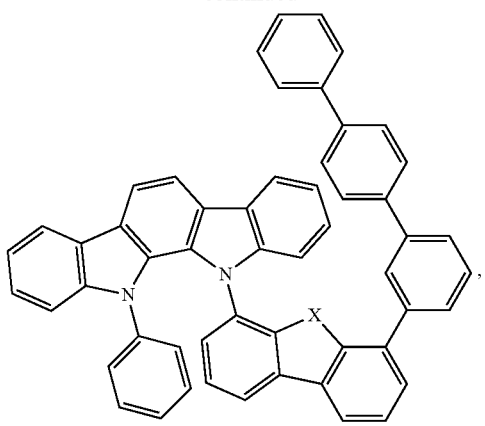

Compound 139, wherein X=O,
Compound 140, wherein X=S,
Compound 141, wherein X=Se,

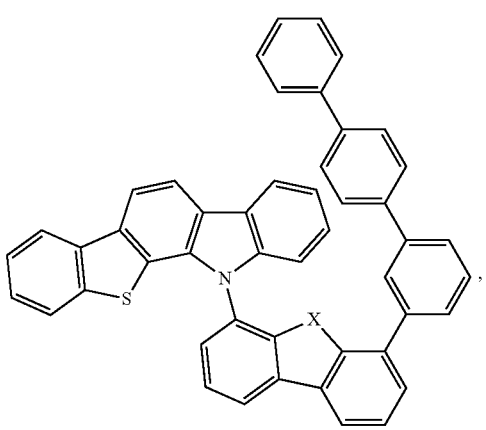

Compound 142, wherein X=O,
Compound 143, wherein X=S,
Compound 144, wherein X=Se,

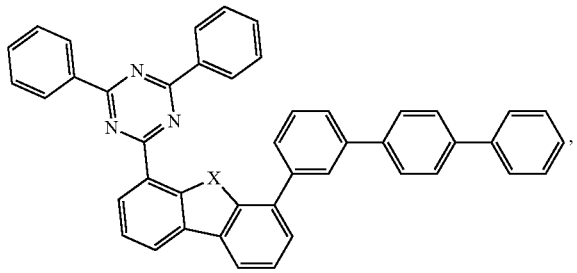

Compound 145, wherein X=O,
Compound 146, wherein X=S,
Compound 147, wherein X=Se,

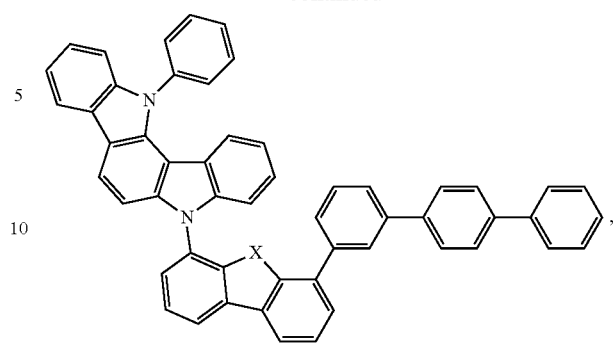

Compound 148, wherein X=O,
Compound 149, wherein X=S,
Compound 150, wherein X=Se,

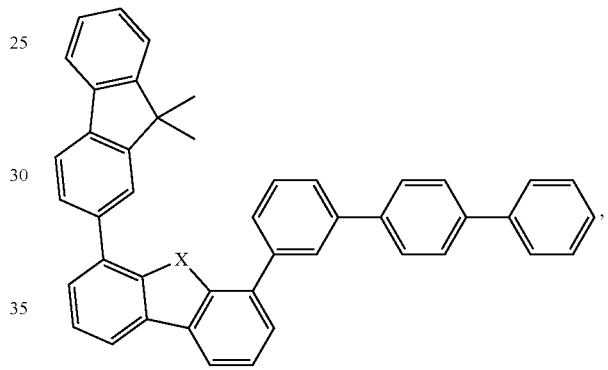

Compound 151, wherein X=O,
Compound 152, wherein X=S,
Compound 153, wherein X=Se,

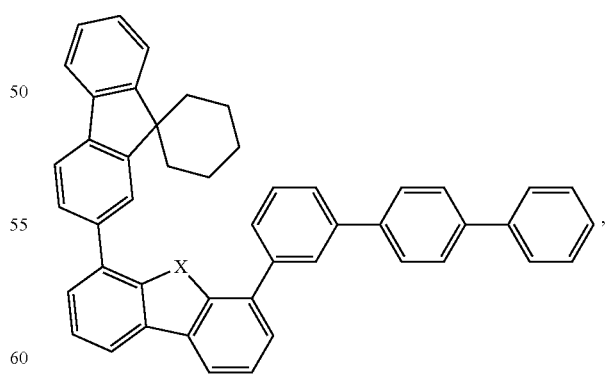

Compound 154, wherein X=O,
Compound 155, wherein X=S,
Compound 156, wherein X=Se, and -continued

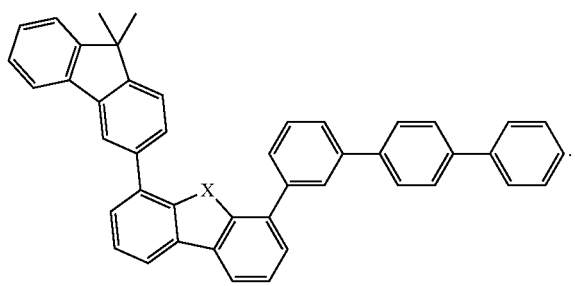

Compound 157, wherein X=O,
Compound 158, wherein X=S,
Compound 159, wherein X=Se, According to another aspect of the present disclosure, a first device comprising a phosphorescent organic light-emitting device is disclosed. The phosphorescent organic light-emitting device comprises: an anode; a cathode; and an organic layer, disposed between the anode and the cathode, comprising a compound having a formula (I)

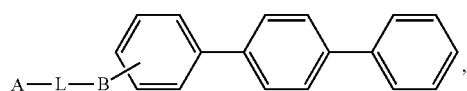

(I)

wherein A is selected from a group consisting of triphenylene, phenanthrene, anthracene, biphenyl, terphenyl, carbazole, dibenzothiophene, dibenzofuran, dibenzoselenophene, fluorene, azatriphenylene, azacarbazole, azadibenzothiophene, azadibenzofuran, azadibenzoselenophene, triazine, or combinations thereof, wherein L is selected from a group consisting of a direct bond, benzene, biphenyl and terphenyl, pyridine, or combinations thereof, and wherein L is optionally further substituted with alkyl, halogen, hydrogen, deuterium, nitrile or aryl; wherein B is selected from a group consisting of dibenzothiophene, dibenzofuran and dibenzoselenophene; and wherein A and B are independently optionally further substituted with one or more substituents selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, and for each of A and B, two adjacent substituents are optionally joined to form a fused ring.

In one embodiment of the first device, the compound is of formula (II)

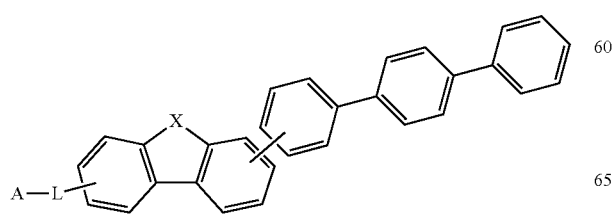

(II) or formula (III)

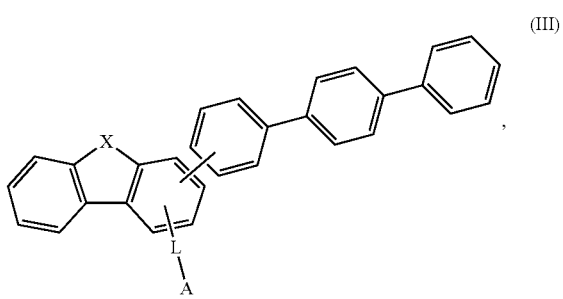

(III)

wherein X is selected from a group consisting of O, S and Se.

In another embodiment of the first device, A is selected from the group consisting of

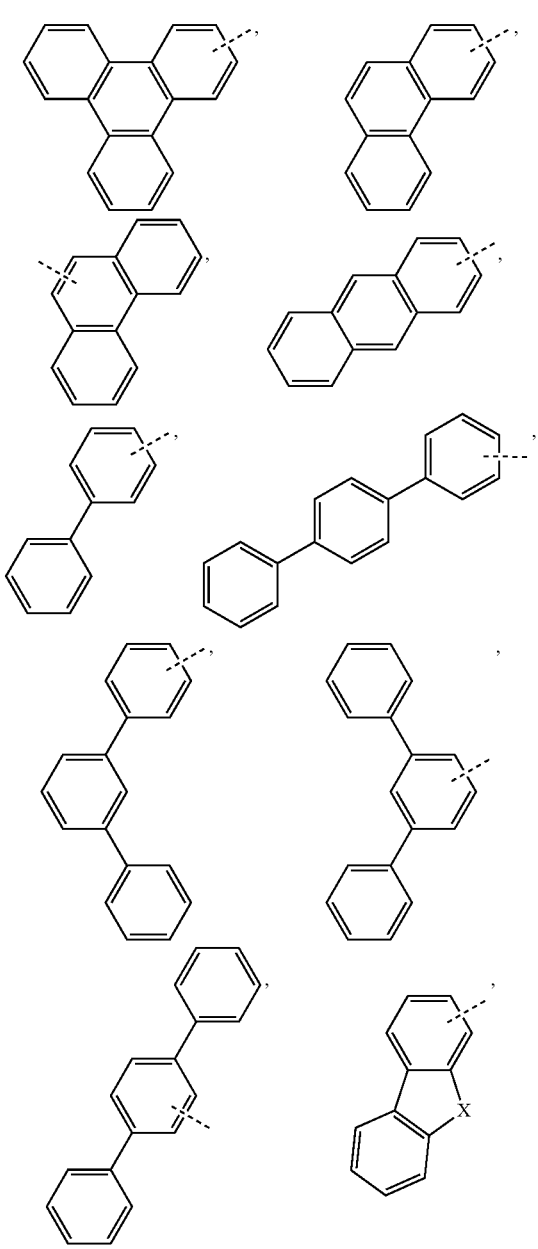

-continued
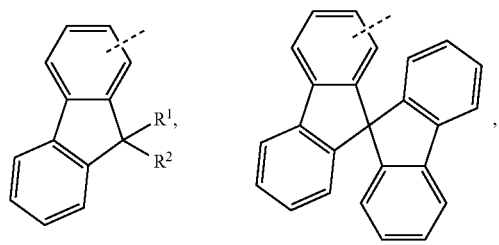
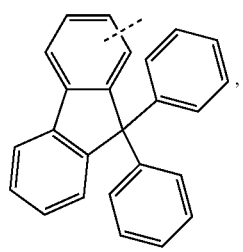
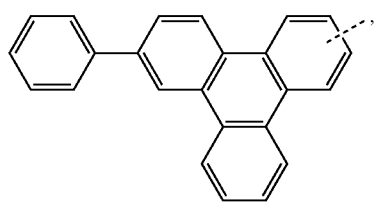
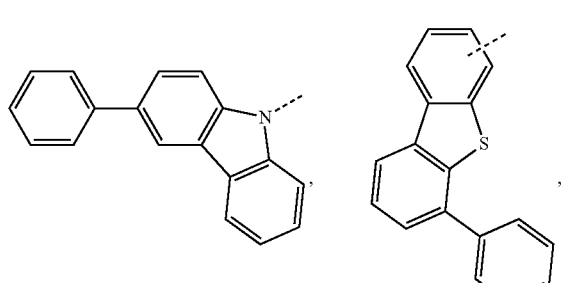
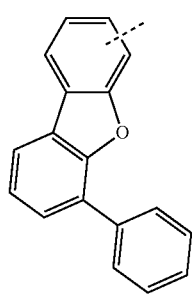, 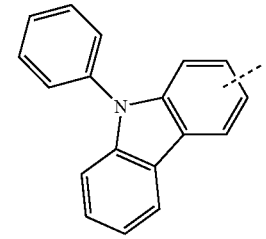
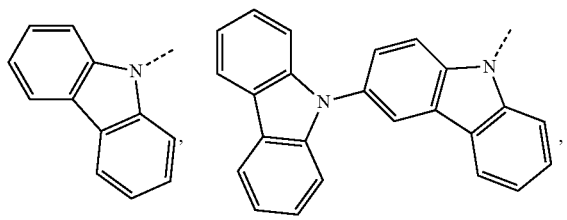
-continued
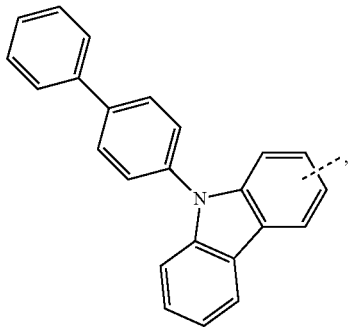
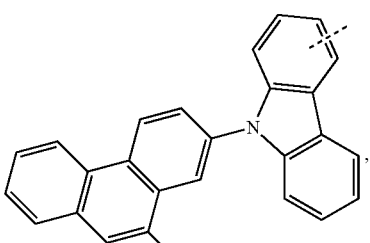
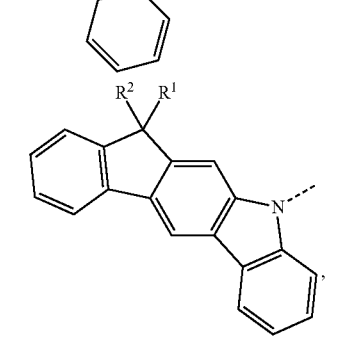
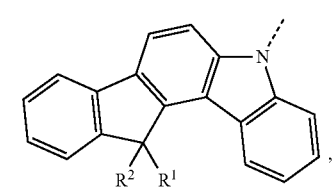
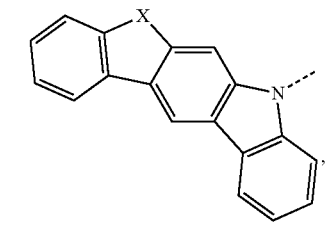
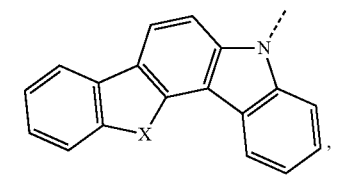
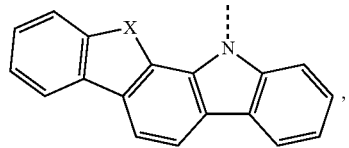

-continued

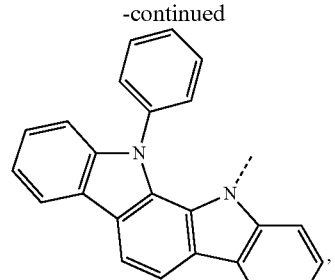

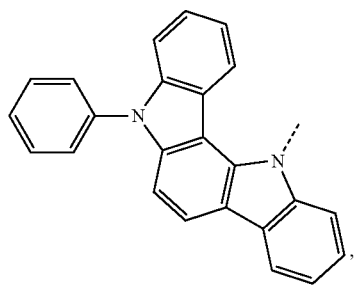

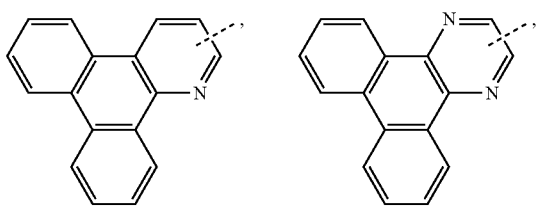

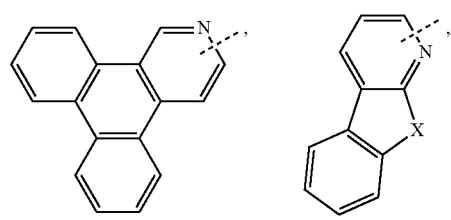

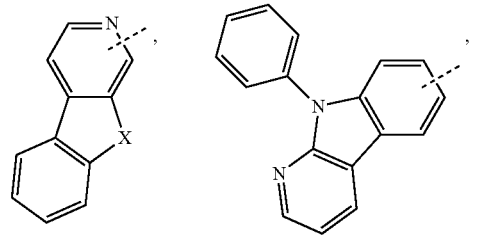

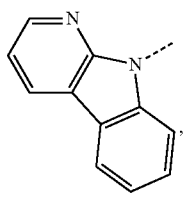

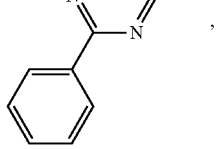 and wherein X is S, O or Se; and $R^1$ and $R^2$ are, independently, linear or branched alkyl with 1 to 12 carbon atoms, and $R^1$ and $R^2$ are optionally jointed to form a ring.

In another embodiment of the first device, B is selected from the group consisting of

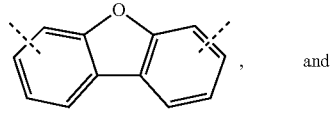 and

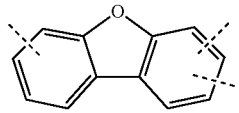

In another embodiment of the first device, L is selected from the group consisting of a direct bond,

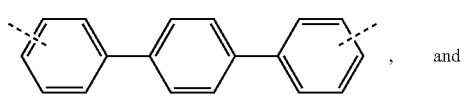 and

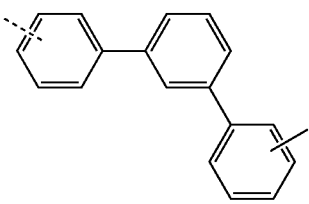

In another embodiment of the first device, the compound having the formula (I) is selected from the group consisting of

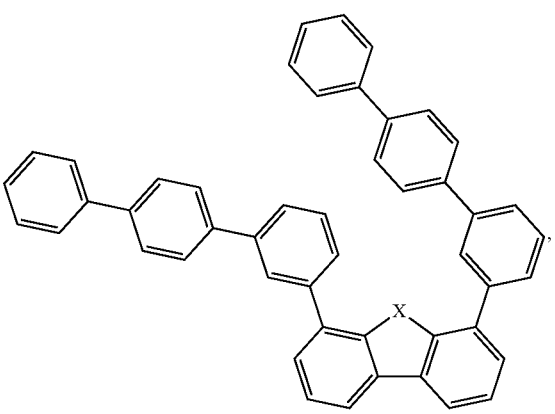

Compound 1, wherein X=O,
Compound 2, wherein X=S,
Compound 3, wherein X=Se,

-continued

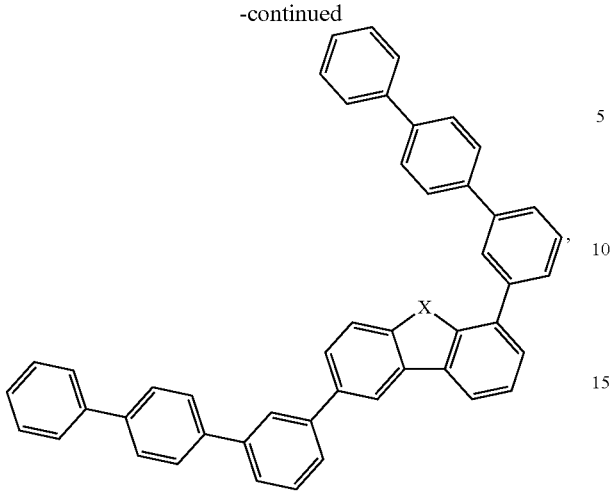

Compound 4, wherein X=O,
Compound 5, wherein X=S,
Compound 6, wherein X=Se,

Compound 7, wherein X=O,
Compound 8, wherein X=S,
Compound 9, wherein X=Se,

Compound 10, wherein X=O,
Compound 11, wherein X=S,
Compound 12, wherein X=Se,

-continued

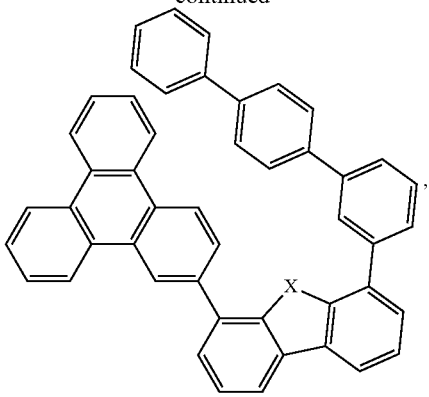

Compound 13, wherein X=O,
Compound 14, wherein X=S,
Compound 15, wherein X=Se,

Compound 16, wherein X=O,
Compound 17, wherein X=S,
Compound 18, wherein X=Se,

Compound 19, wherein X=O,
Compound 20, wherein X=S,
Compound 21, wherein X=Se,

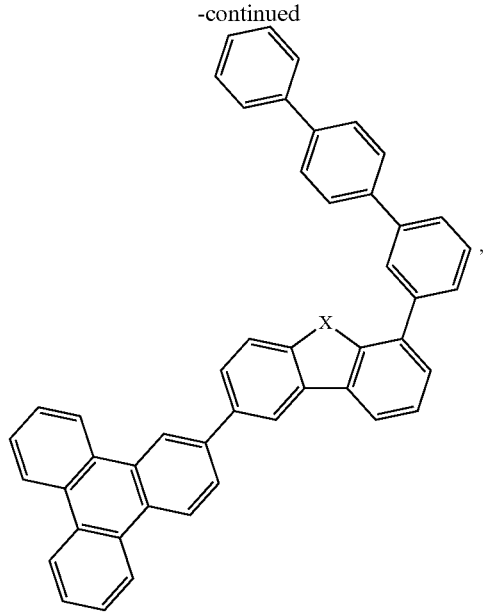

Compound 22, wherein X=O,
Compound 23, wherein X=S,
Compound 24, wherein X=Se,

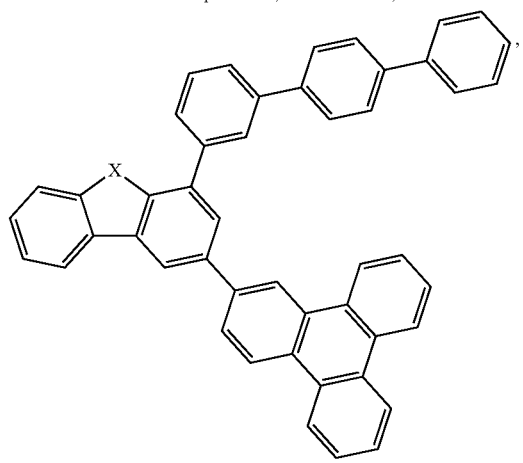

Compound 25, wherein X=O,
Compound 26, wherein X=S,
Compound 27, wherein X=Se,

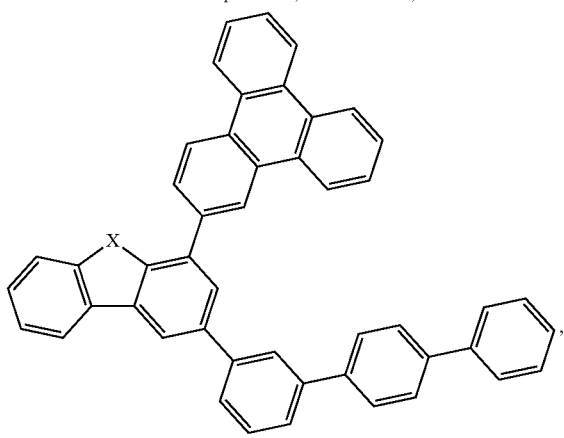

Compound 28, wherein X=O,
Compound 29, wherein X=S,
Compound 30, wherein X=Se,

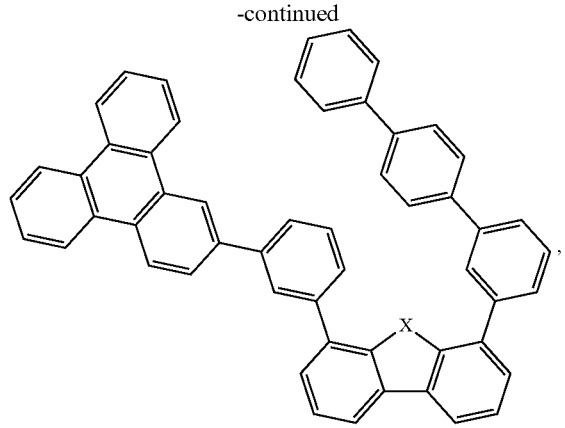

Compound 31, wherein X=O,
Compound 32, wherein X=S,
Compound 33, wherein X=Se,

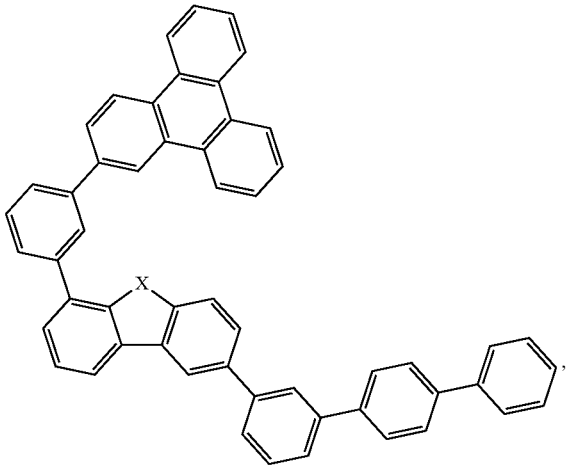

Compound 34, wherein X=O,
Compound 35, wherein X=S,
Compound 36, wherein X=Se,

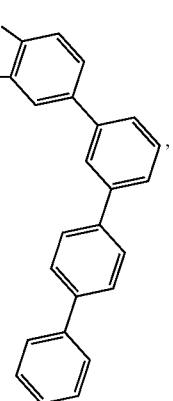

Compound 37, wherein X=O,
Compound 38, wherein X=S,
Compound 39, wherein X=Se,

-continued

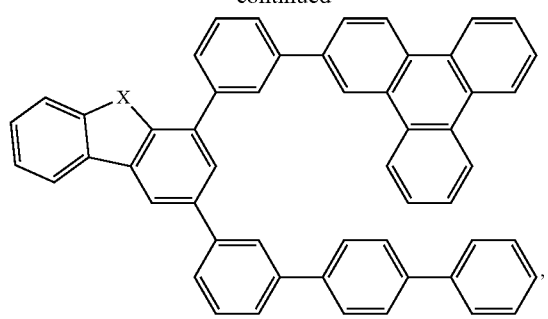

Compound 40, wherein X=O,
Compound 41, wherein X=S,
Compound 42, wherein X=Se,

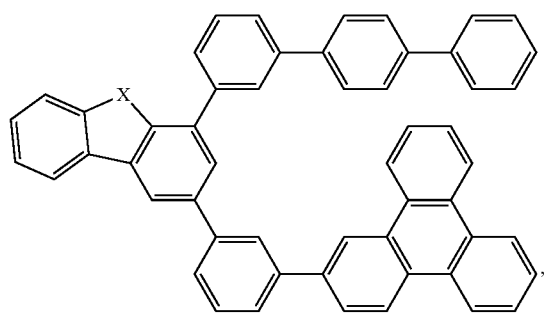

Compound 43, wherein X=O,
Compound 44, wherein X=S,
Compound 45, wherein X=Se,

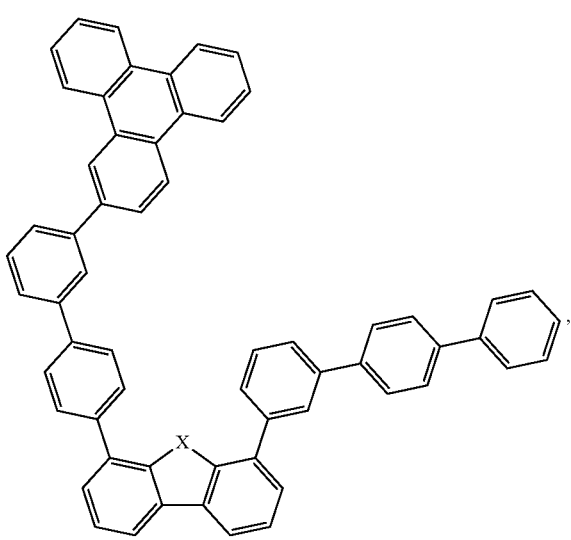

Compound 46, wherein X=O,
Compound 47, wherein X=S,
Compound 48, wherein X=Se,

-continued

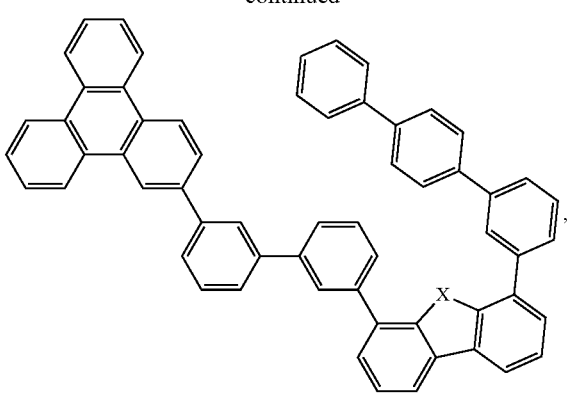

Compound 49, wherein X=O,
Compound 50, wherein X=S,
Compound 51, wherein X=Se,

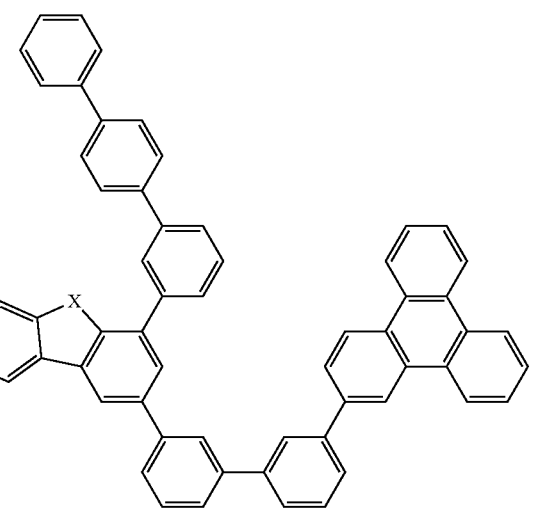

Compound 52, wherein X=O,
Compound 53, wherein X=S,
Compound 54, wherein X=Se,

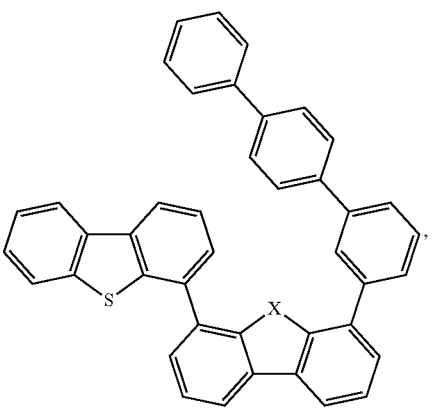

Compound 55, wherein X=O,
Compound 56, wherein X=S,
Compound 57, wherein X=Se,

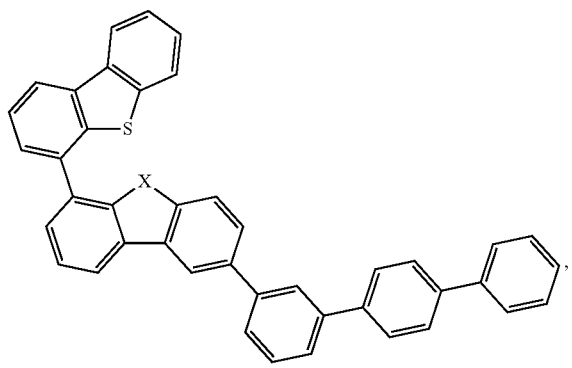

Compound 58, wherein X=O,
Compound 59, wherein X=S,
Compound 60, wherein X=Se,

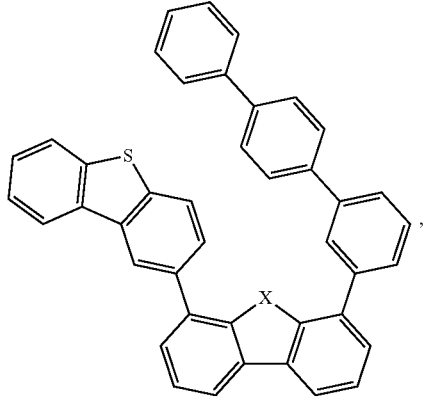

Compound 67, wherein X=O,
Compound 68, wherein X=S,
Compound 69, wherein X=Se,

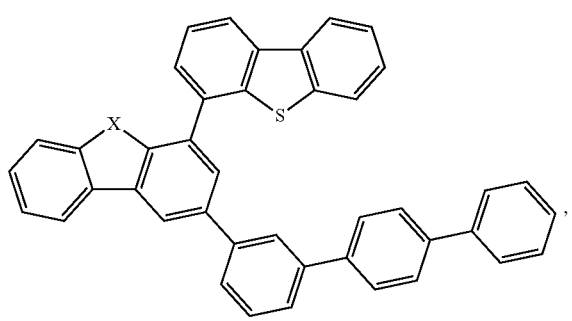

Compound 61, wherein X=O,
Compound 62, wherein X=S,
Compound 63, wherein X=Se,

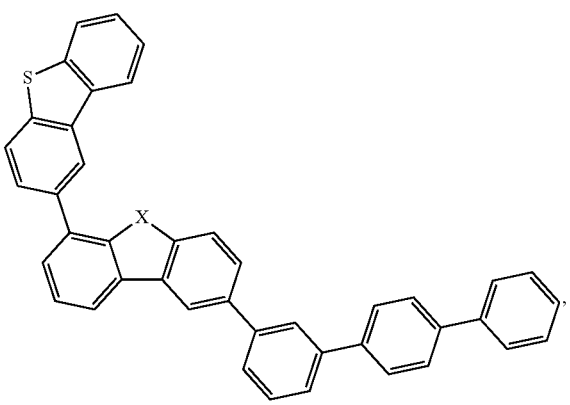

Compound 70, wherein X=O,
Compound 71, wherein X=S,
Compound 72, wherein X=Se,

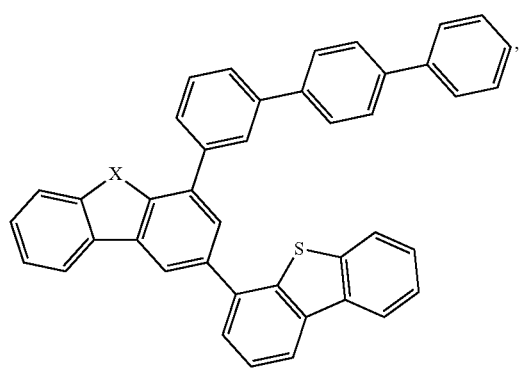

Compound 64, wherein X=O,
Compound 65, wherein X=S,
Compound 66, wherein X=Se,

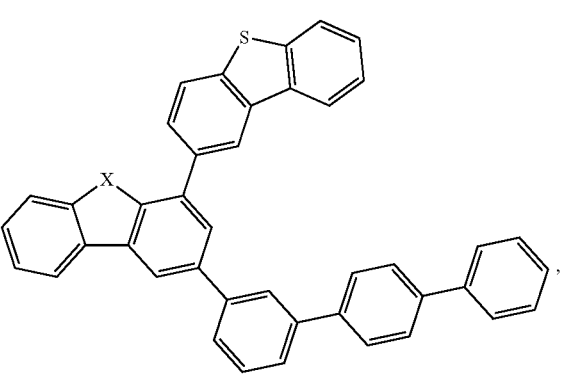

Compound 73, wherein X=O,
Compound 74, wherein X=S,
Compound 75, wherein X=Se,

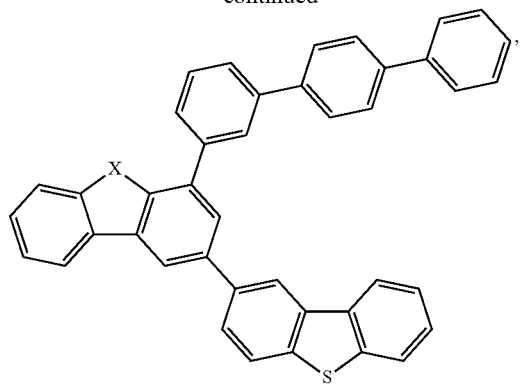

Compound 76, wherein X=O,
Compound 77, wherein X=S,
Compound 78, wherein X=Se,

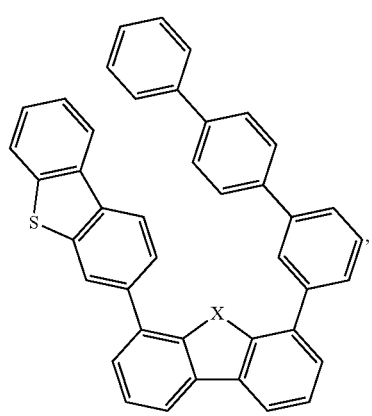

Compound 79, wherein X=O,
Compound 80, wherein X=S,
Compound 81, wherein X=Se,

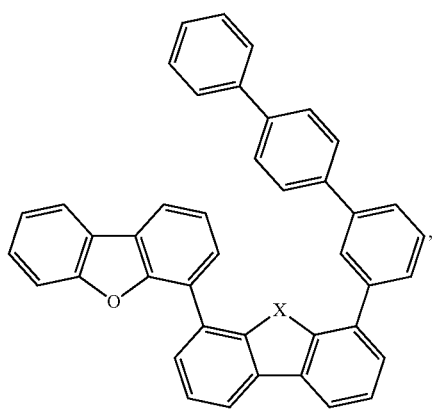

Compound 82, wherein X=O,
Compound 83, wherein X=S,
Compound 84, wherein X=Se,

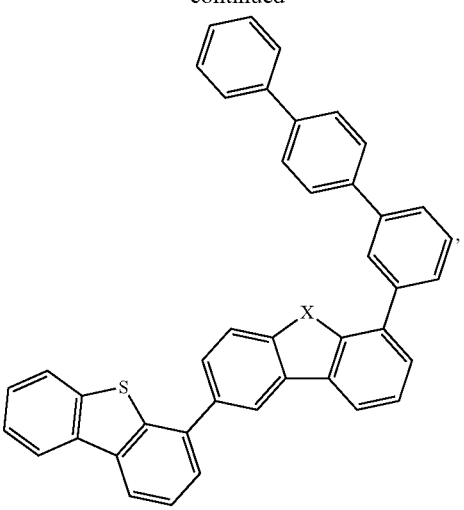

Compound 85, wherein X=O,
Compound 86, wherein X=S,
Compound 87, wherein X=Se,

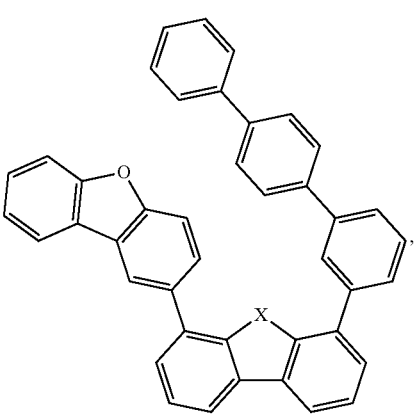

Compound 88, wherein X=O,
Compound 89, wherein X=S,
Compound 90, wherein X=Se,

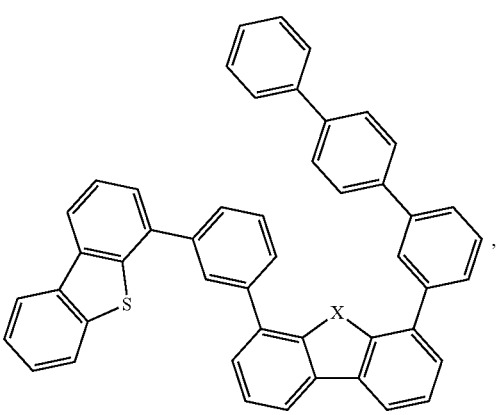

Compound 91, wherein X=O,
Compound 92, wherein X=S,
Compound 93, wherein X=Se,

-continued

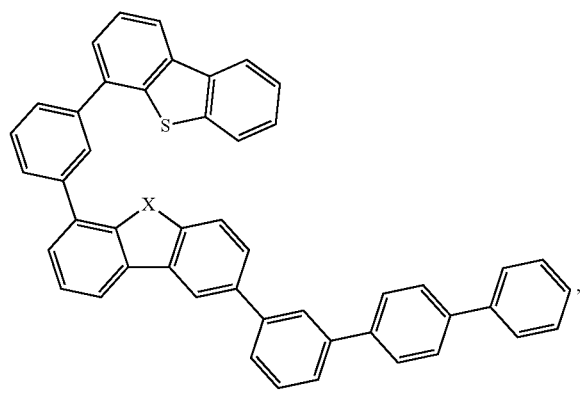

Compound 94, wherein X=O,
Compound 95, wherein X=S,
Compound 96, wherein X=Se,

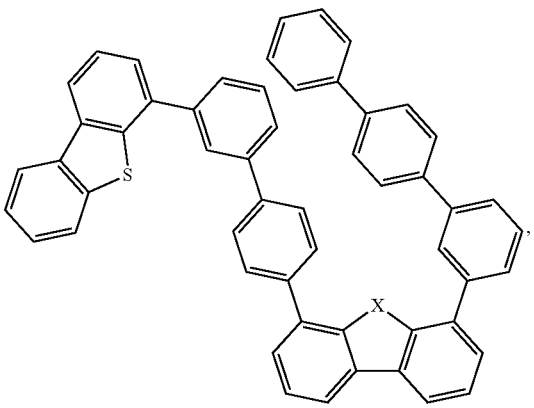

Compound 103, wherein X=O,
Compound 104, wherein X=S,
Compound 105, wherein X=Se,

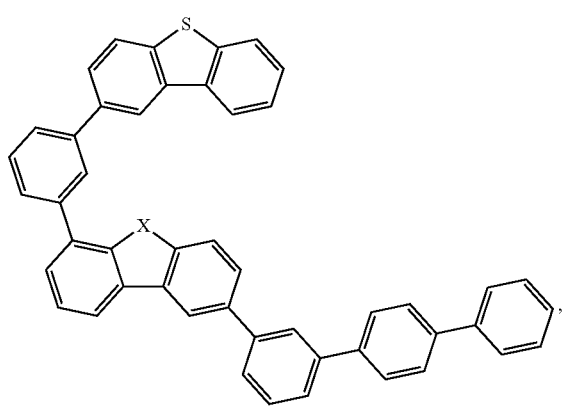

Compound 97, wherein X=O,
Compound 98, wherein X=S,
Compound 99, wherein X=Se,

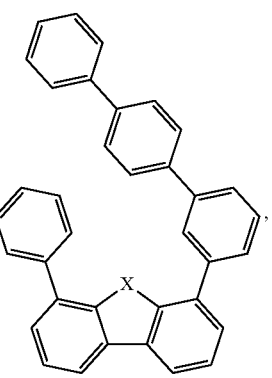

Compound 106, wherein X=O,
Compound 107, wherein X=S,
Compound 108, wherein X=Se,

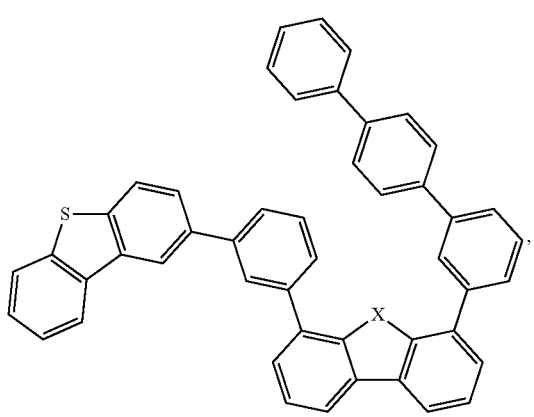

Compound 100, wherein X=O,
Compound 101, wherein X=S,
Compound 102, wherein X=Se,

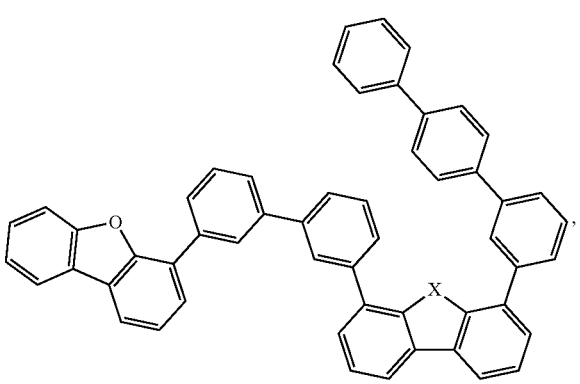

Compound 109, wherein X=O,
Compound 110, wherein X=S,
Compound 111, wherein X=Se, -continued

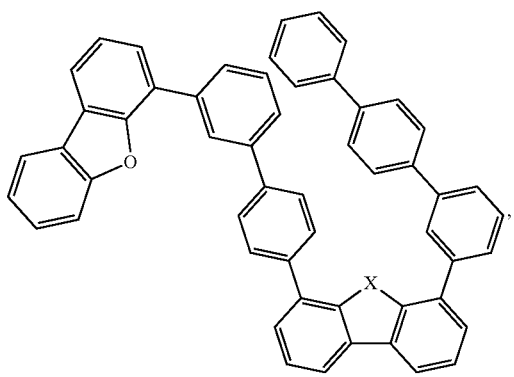

Compound 112, wherein X=O,
Compound 113, wherein X=S,
Compound 114, wherein X=Se,

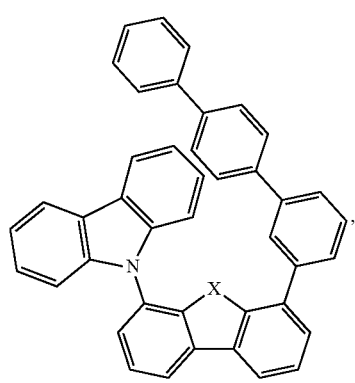

Compound 115, wherein X=O,
Compound 116, wherein X=S,
Compound 117, wherein X=Se,

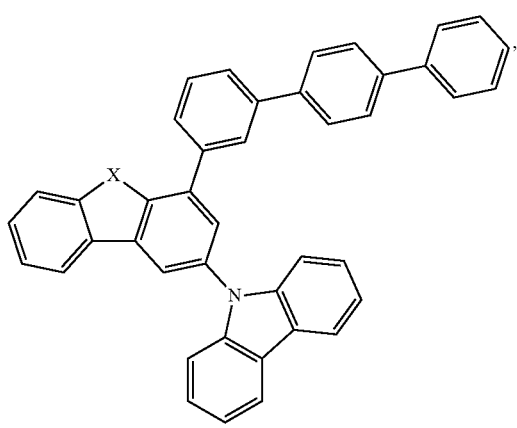

Compound 118, wherein X=O,
Compound 119, wherein X=S,
Compound 120, wherein X=Se, -continued

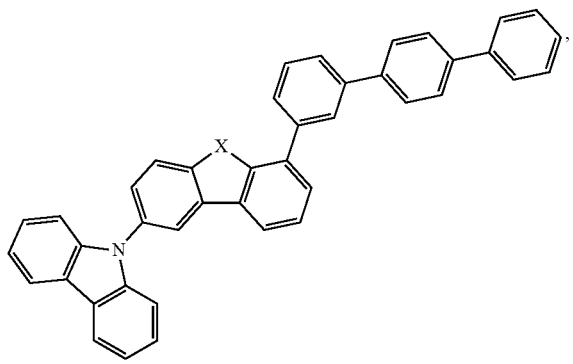

Compound 121, wherein X=O,
Compound 122, wherein X=S,
Compound 123, wherein X=Se,

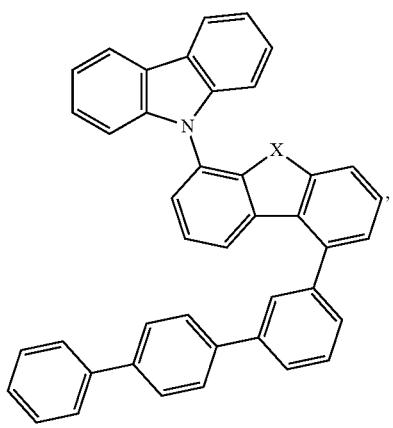

Compound 124, wherein X=O,
Compound 125, wherein X=S,
Compound 126, wherein X=Se,

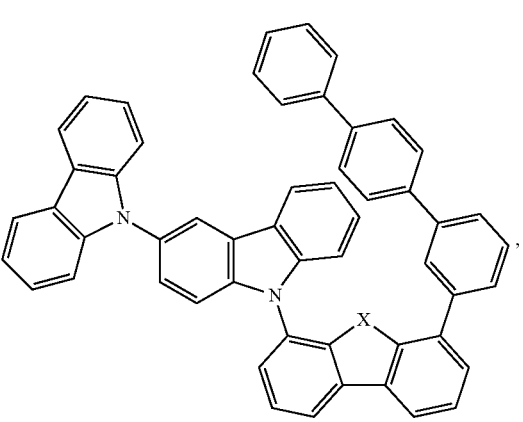

Compound 127, wherein X=O,
Compound 128, wherein X=S,
Compound 129, wherein X=Se,

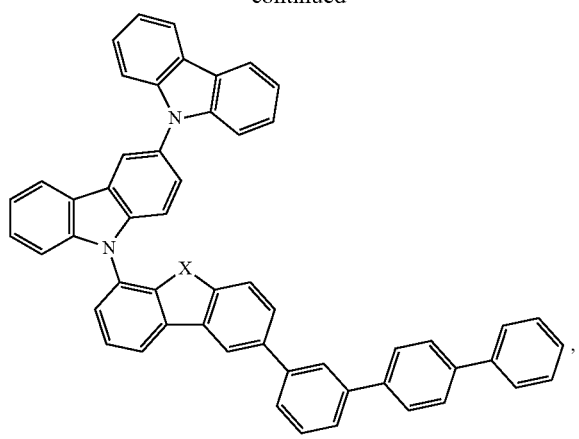

Compound 130, wherein X=O,
Compound 131, wherein X=S,
Compound 132, wherein X=Se,

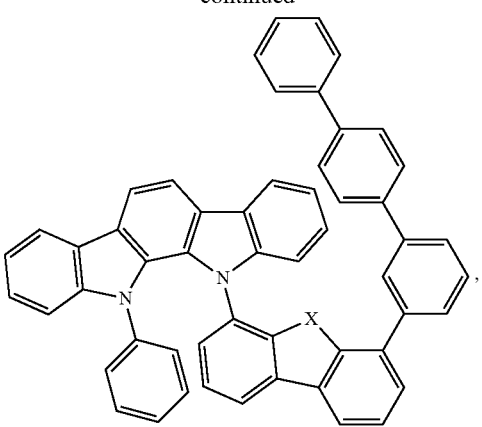

Compound 139, wherein X=O,
Compound 140, wherein X=S,
Compound 141, wherein X=Se,

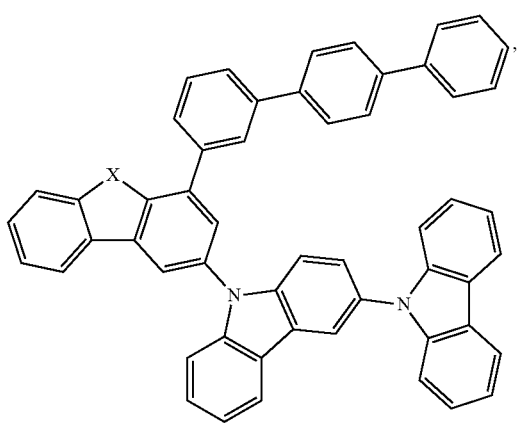

Compound 133, wherein X=O,
Compound 134, wherein X=S,
Compound 135, wherein X=Se,

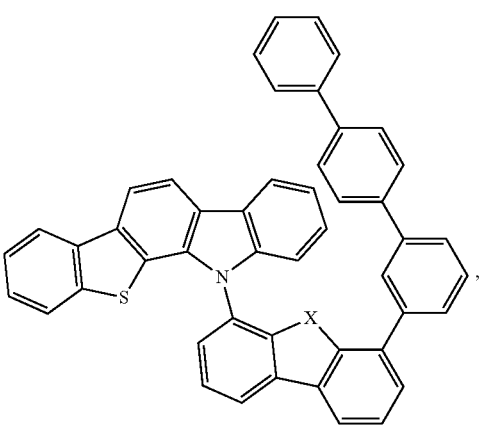

Compound 142, wherein X=O,
Compound 143, wherein X=S,
Compound 144, wherein X=Se,

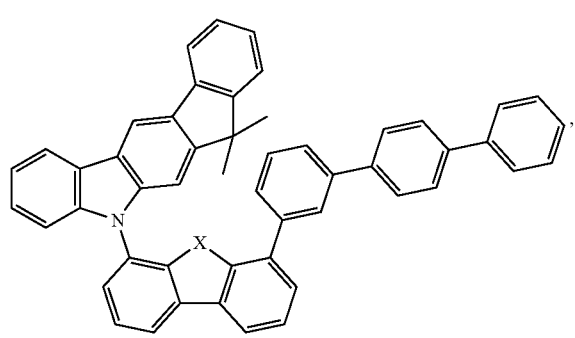

Compound 136, wherein X=O,
Compound 137, wherein X=S,
Compound 138, wherein X=Se,

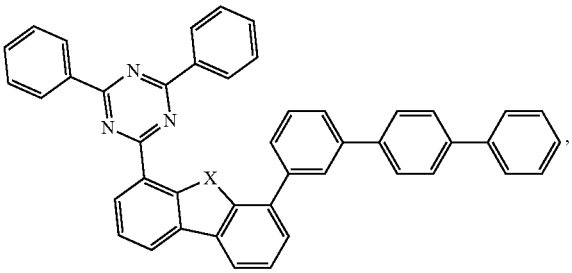

Compound 145, wherein X=O,
Compound 146, wherein X=S,
Compound 147, wherein X=Se, -continued

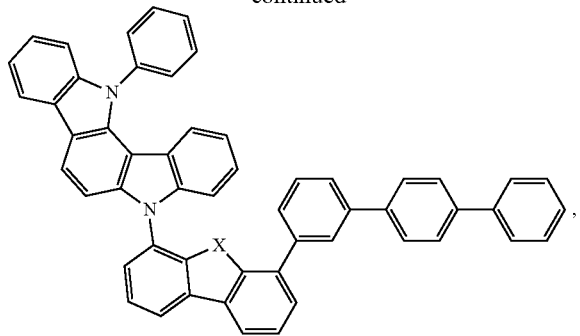

Compound 148, wherein X=O,
Compound 149, wherein X=S,
Compound 150, wherein X=Se,

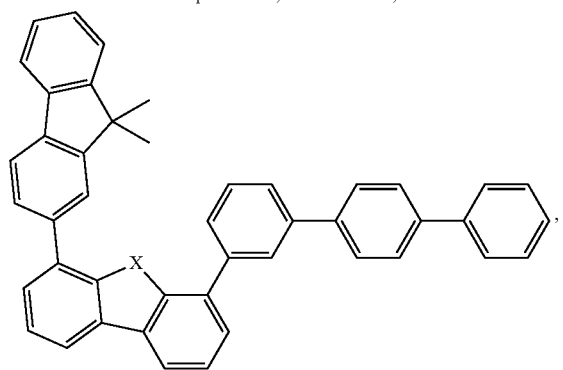

Compound 151, wherein X=O,
Compound 152, wherein X=S,
Compound 153, wherein X=Se,

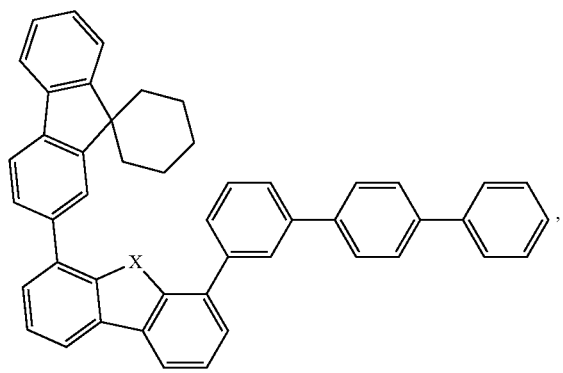

Compound 154, wherein X=O,
Compound 155, wherein X=S,
Compound 156, wherein X=Se,
and

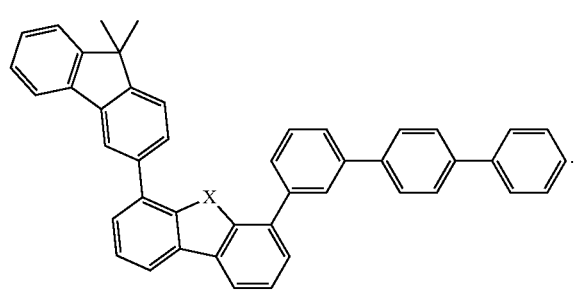

Compound 157, wherein X=O,
Compound 158, wherein X=S,
Compound 159, wherein X=Se, In one embodiment of the first device, the organic layer is an emissive layer and the compound of the formula (I) is a host. The organic layer can further comprise a phosphorescent emissive dopant.

In one embodiment of the first device, the phosphorescent emissive dopant is a transition metal complex having at least one ligand selected from the group consisting of:

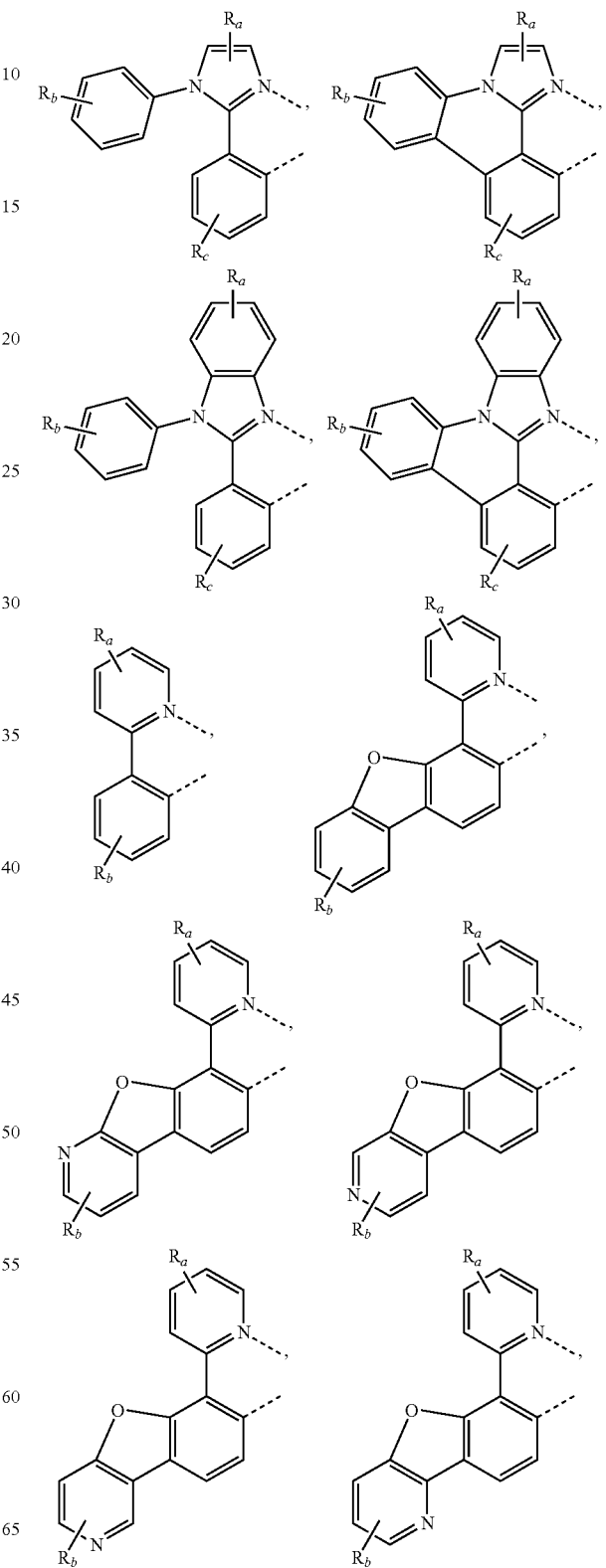

-continued

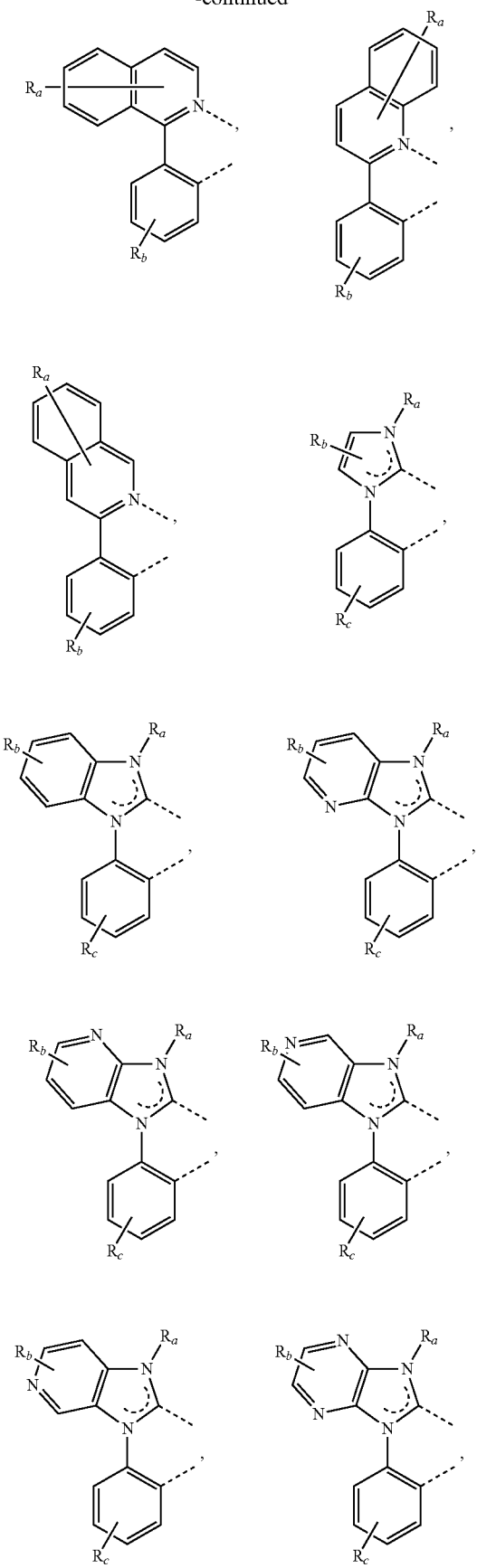

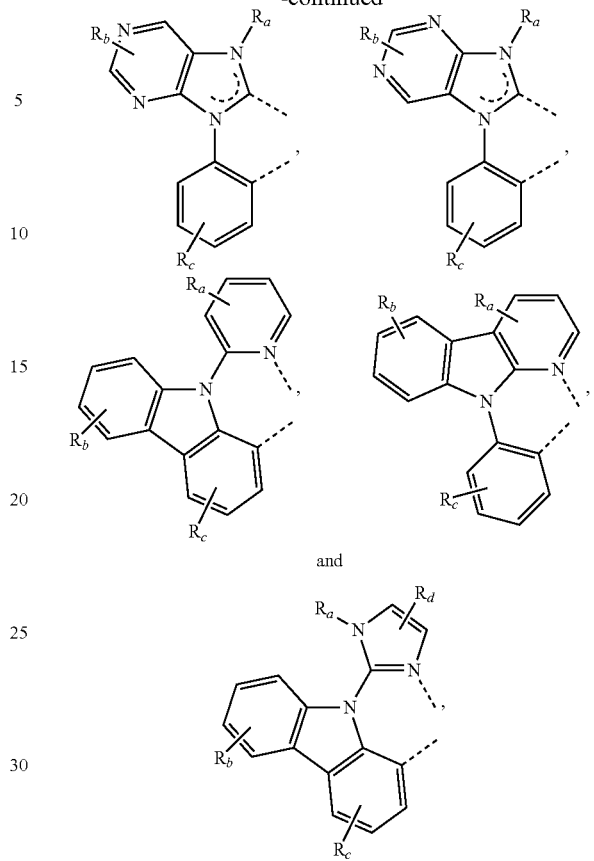

and wherein $R_a$, $R_b$, $R_c$, and $R_d$ may represent mono, di, tri, or tetra substitution, or no substitution; wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In one embodiment of the first device, the organic layer is a blocking layer and the compound of the formula (I) is a blocking material in the organic layer. In another embodiment, the organic layer is an electron transporting layer and the compound of the formula (I) is an electron transporting material in the organic layer.

In one embodiment of the first device, the first device is a consumer product. In another embodiment, the first device is an organic light-emitting device. In another embodiment, the first device can comprise a lighting panel.

According to another aspect, a formulation comprising the compound having the structure according to the formula (I) as defined herein is also disclosed.

SYNTHESIS OF THE NOVEL COMPOUNDS

Chemical abbreviations used throughout this document are as follows: "SPhos" is dicyclohexyl(2',6'-dimethoxy-[1,1'-biphenyl]-2-yl)phosphine; "Pd$_2$(dba)$_3$" is tri(dibenzylideneacetone) dipalladium(0); "tert-BuONa" is sodium tert-butoxide; "DCM" is dichloromethane; "EtOAc" is ethylacetate; and "DME" is dimethoxyethane.

Synthesis of Compound 2

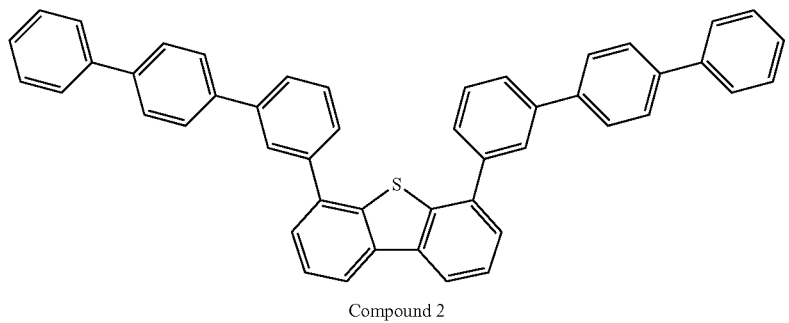

Compound 2

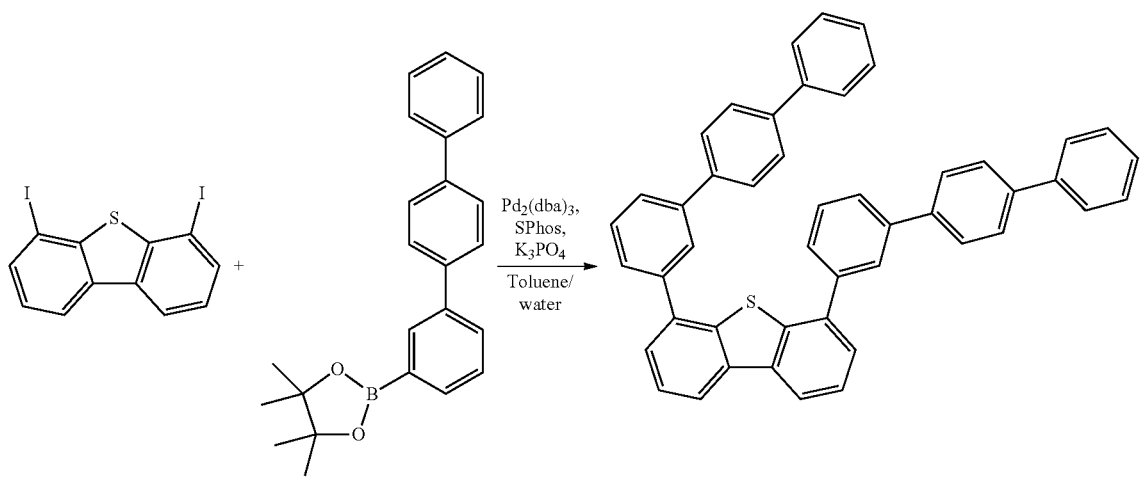

(1) A solution of 4,6-diiododibenzo[b,d]thiophene (3.1 g, 7.11 mmol), 2-([1,1':4',1''-terphenyl]-3-yl)-4,4,5,5-tetramethyl-1,3,2-dioxaborolane (5.32 g, 14.93 mmol), $Pd_2(dba)_3$ (0.260 g, 0.284 mmol), SPhos (0.233 g, 0.569 mmol) and $K_3PO_4$ (9.05 g, 42.7 mmol) in toluene (200 ml) and water (40 ml) was refluxed under nitrogen for 2 days. After cooling to room temperature, the precipitation was collected by filtration, dissolved in hot DCM and dried over $Na_2SO_4$. After evaporation off the solvent, the solid was dissolved in boiling toluene, filtered through a short plug of silica gel, and triturated with EtOAc to yield Compound 2 (3.55 g, 77%) as a white solid.

Synthesis of Compound 14

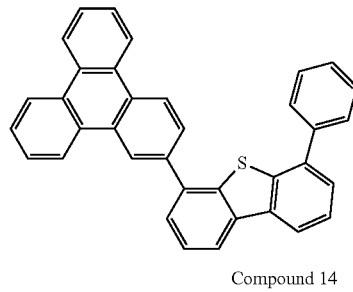

Compound 14

-continued

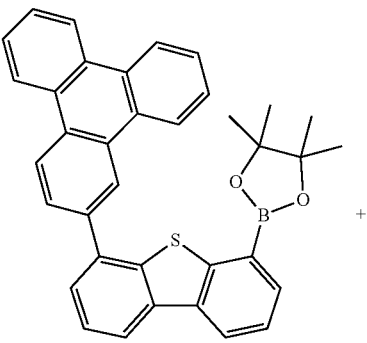

(1)

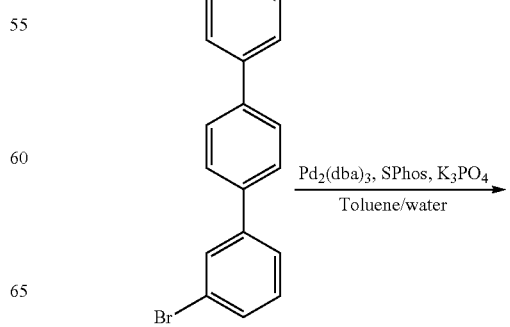

-continued

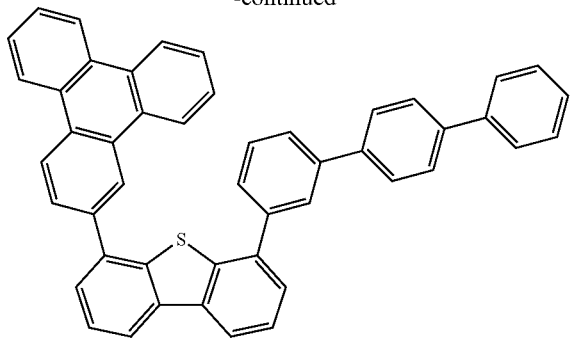

(1) A solution of 4,4,5,5-tetramethyl-2-(6-(triphenylen-2-yl)dibenzo[b,d]thiophen-4-yl)-1,3,2-dioxaborolane (2.81 g, 5.24 mmol), 3-bromo-1,1':4',1''-terphenyl (1.620 g, 5.24 mmol), Pd$_2$(dba)$_3$ (0.096 g, 0.105 mmol), SPhos (0.172 g, 0.419 mmol) and K$_3$PO$_4$ (2.224 g, 10.48 mmol) in toluene (50 ml) and water (5 ml) was refluxed under nitrogen overnight. After cooling to room temperature, the solid precipitation was collected by filtration and washed with water and heptane. The solid was dissolved in boiling toluene and filtered through a short plug of silica gel. Upon evaporation off the solvent, the crude product was recrystallized from toluene to yield Compound 14 (2.0 g, 60%) as a white solid.

Synthesis of Compound 32

(1) A solution of 4-bromodibenzo[bd]thiophene (5.00 g, 19.00 mmol), 2-([1,1':4',1''-terphenyl]-3-yl)-4,4,5,5-tetramethyl-1,3,2-dioxaborolane (6.77 g, 19.00 mmol), Pd(PPh$_3$)$_4$ (0.659 g, 0.570 mmol) and K$_2$CO$_3$ (7.88 g, 57.0 mmol) in DME (150 ml) and water (30 ml) was refluxed under nitrogen overnight. After cooling to room temperature, the solid was collected by filtration and the filtrate was extracted with DCM, washed with water and evaporated. The combined solid was purified by column chromatography on silica gel with heptane/DCM (9/1, v/v) as eluent to yield 4-([1,1':4',1''-terphenyl]-3-yl)dibenzo[b,d]thiophene (6.8 g, 87%) as a white solid.

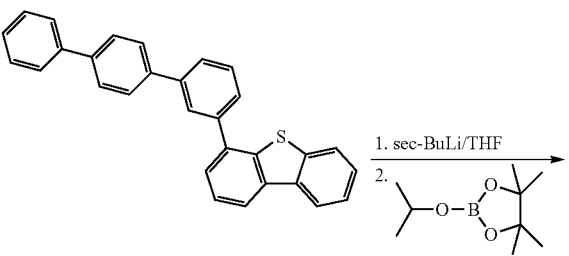

(2)

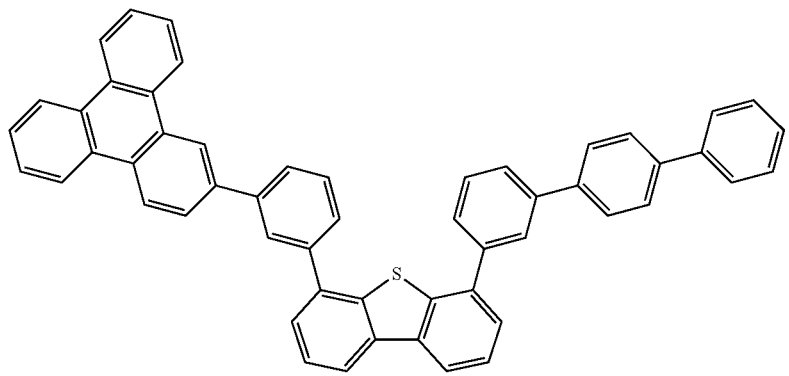

Compound 32

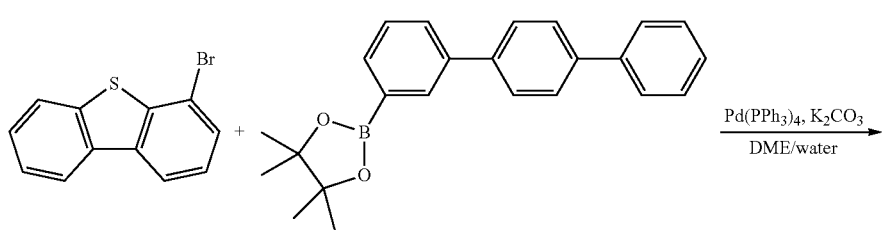

(1)

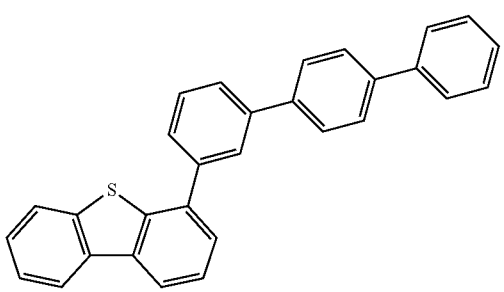

-continued

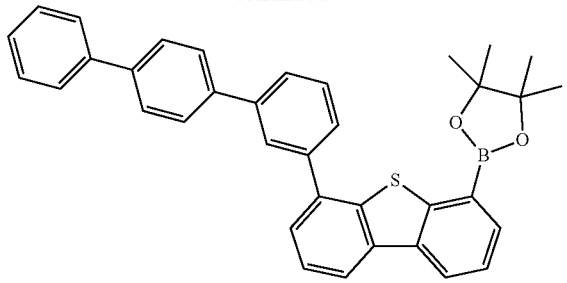

(2) Into a solution of 4-([1,1':4',1"-terphenyl]-3-yl)dibenzo[b,d]thiophene (6.8 g, 16.48 mmol) in THF (200 ml) was added dropwise a solution of sec-butyllithium in cyclohexane (15.31 ml, 1.4 M, 21.43 mmol) over 5 min at −78° C. The solution turned deep blue immediately. The solution was stirred at this temperature for 2 hours before quenching with 2-isopropoxy-4,4,5,5-tetramethyl-1,3,2-dioxaborolane (5.04 ml, 24.72 mmol) introduced in one portion. The solution was allowed to warm slowly to room temperature and stirred overnight before quenching with water. The reaction mixture was extracted with ether, washed with brine, dried over Na$_2$SO$_4$ and evaporated. The residue was purified by column chromatography on silica gel with heptane/DCM (9/1 to 7/3, v/v) as eluent and precipitation in heptane to yield 2-(6-([1,1':4',1"-terphenyl]-3-1)dibenzo[b,d]thiophen-4-yl)-4,4,5,5-tetramethyl-1,3,2-dioxaborolane (5.4 g, 61%) as a white solid.

(3) A solution of 2-(6-([1,1':4',1"-terphenyl]-3-yl)dibenzo[b,d]thiophen-4-yl)-4,4,5,5-tetramethyl-1,3,2-dioxaborolane (2.70 g, 5.01 mmol), 2-(3-bromophenyl)triphenylene (1.92 g, 5.01 mmol), Pd$_2$(dba)$_3$ (0.09 g, 0.10 mmol), SPhos (0.082 g, 0.201 mmol) and K$_3$PO$_4$ (3.19 g, 15.04 mmol) in toluene (50 ml) and water (10 ml) was refluxed under nitrogen for 2 hours. After cooling to room temperature, the solid was collected by filtration, washed with toluene, redissolved in boiling toluene and filtered through a short plug of silica gel. Upon evaporation off the solvent, the crude product was further purified by recrystallization from toluene to yield Compound 32 (2.2 g, 61%) as a white solid.

Synthesis of Compound 92

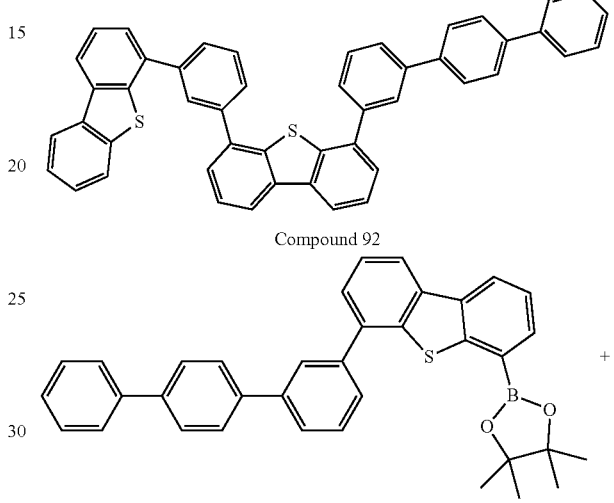

Compound 92

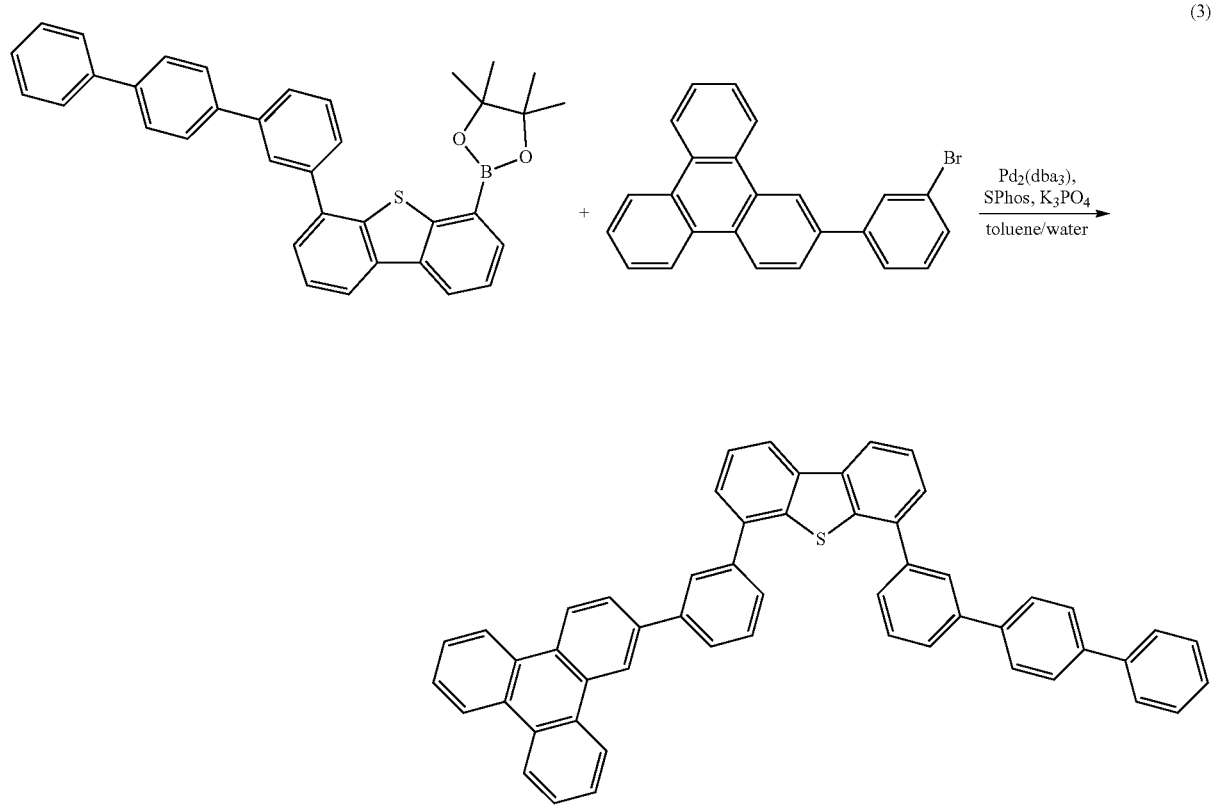 [SMILES: CC1(C)OB(c2cccc3c2sc2c(-c4cccc(-c5ccc(-c6ccccc6)cc5)c4)cccc23)OC1(C)C ; Brc1cccc(-c2ccc3c4ccccc4c4ccccc4c3c2)c1 ; c1ccc(-c2ccc(-c3cccc(-c4cccc5c4sc4c(-c6cccc(-c7ccc8c9ccccc9c9ccccc9c8c7)c6)cccc45)c3)cc2)cc1]

(3)

-continued

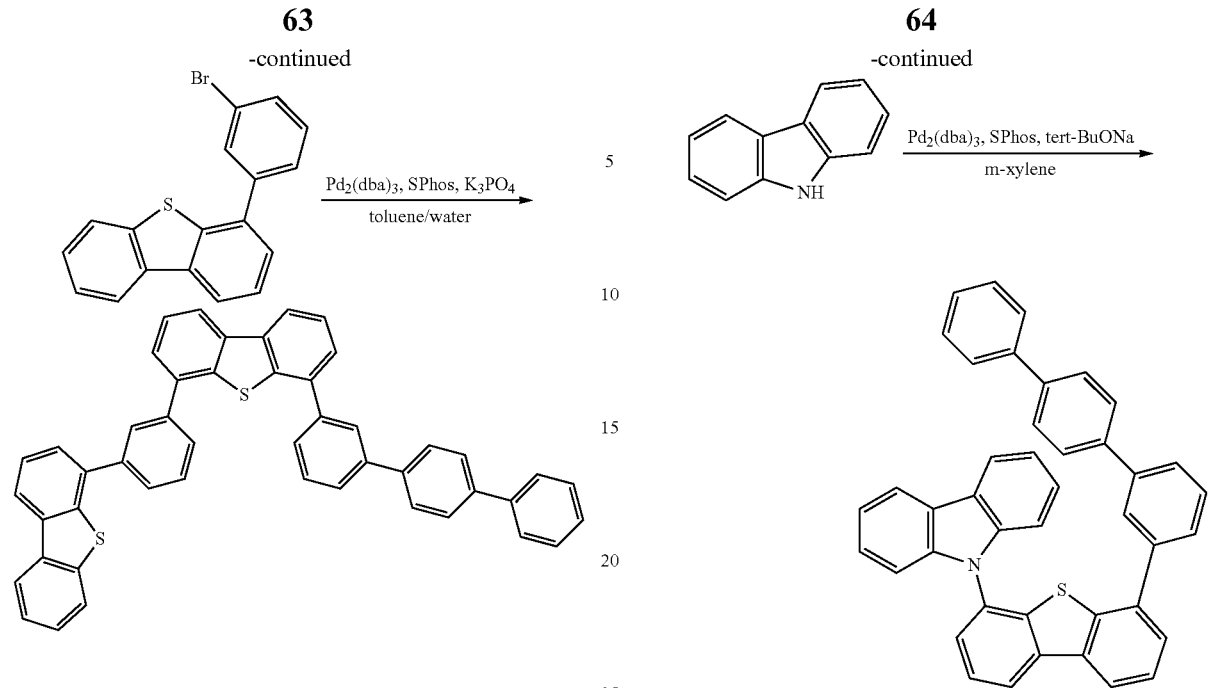

A solution of 2-(6-([1,1':4',1''-terphenyl]-3-yl)dibenzo[b,d]thiophen-4-yl)-4,4,5,5-tetramethyl-1,3,2-dioxaborolane (2.70 g, 5.01 mmol), 4-(3-bromophenyl)dibenzo[bd]thiophene (2.04 g, 6.02 mmol), Pd$_2$(dba)$_3$ (0.09 g, 0.10 mmol), SPhos (0.08 g, 0.20 mmol) and K$_3$PO$_4$ (3.19 g, 15.04 mmol) in toluene (50 ml) and water (10 ml) was refluxed under nitrogen for 2 hours. After cooling to room temperature, the solution was diluted with water, extracted with DCM, dried over Na$_2$SO$_4$ and the solvent was evaporated. The residue was purified by column chromatography on silica gel with heptane/DCM (9/1 to 4/1, v/v) as eluent to yield Compound 92 (2.50 g, 74%) as a white solid.

Synthesis of Compound 116

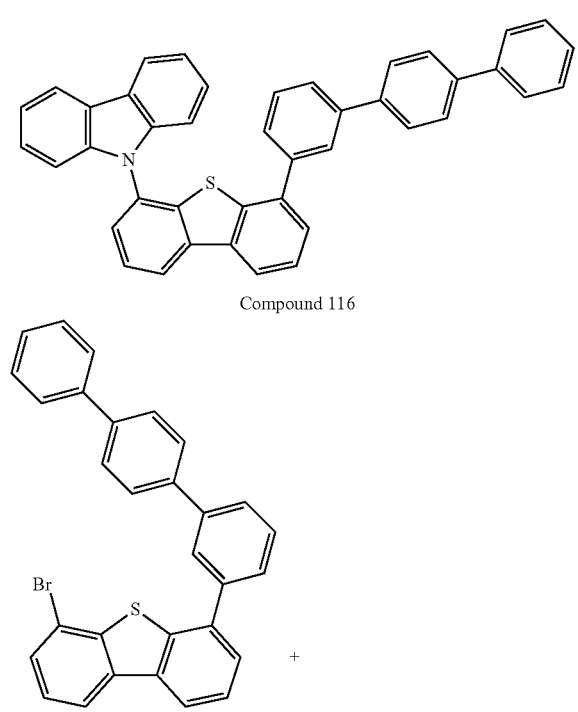

A solution of 4-([1,1':4',1''-terphenyl]-3-yl)-6-bromodibenzo[b,d]thiophene (3.50 g, 7.12 mmol), 9H-carbazole (1.43 g, 8.55 mmol), Pd$_2$(dba)$_3$ (0.13 g, 0.14 mmol), SPhos (0.23 g, 0.57 mmol) and tert-BuONa (1.37 g, 14.24 mmol) in m-xylene (30 ml) was refluxed under nitrogen for 36 hours. The solid was collected by filtration, dissolved in boiling toluene and filtered through a short plug of silica gel. Upon evaporation off the solvent, Compound 116 (2.57 g, 63%) recrystallized from toluene as a white solid.

EXPERIMENTAL DATA

All devices were fabricated by high vacuum (~10$^{-7}$ Torr) thermal evaporation. The anode electrode was 120 nm of indium tin oxide (ITO). The cathode electrode consisted of 1 nm of LiF followed by 100 nm of Al. All devices were encapsulated with a glass lid sealed with an epoxy resin in a nitrogen glove box (<1 ppm of H$_2$O and O$_2$) immediately after fabrication, and a moisture getter was incorporated inside the package.

Device Example 1—A first set of device examples have organic stacks consisting of, sequentially, from the ITO surface, 10 nm of Compound A as the hole injection layer (HIL), 30 nm of 4,4'-bis[N-(1-naphthyl)-N-phenylaminolbiphenyl (NPD) as the hole-transport layer (HTL), and 25 nm of inventive hosts (Compound 14) or comparative hosts (CC-1) with 30 wt % of compound COHost and 12 wt % of Compound A as the emissive layer (EML). On top of the EML, 100 nm of COHost was deposited as the hole blocking layer (HBL), followed by 45 nm of tris(8-hydroxyquinolinato)aluminum (Alq$_3$) as the electron-transport layer (ETL). The structures of the compounds used are shown below.

Compound A

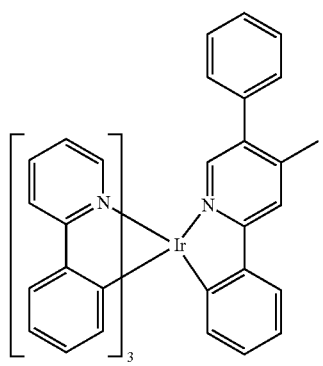

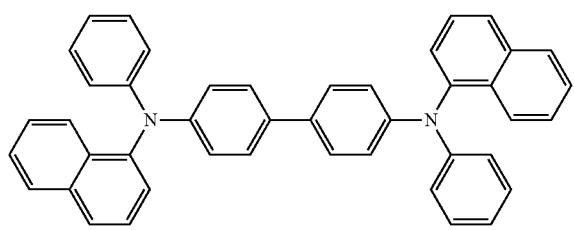

NPD

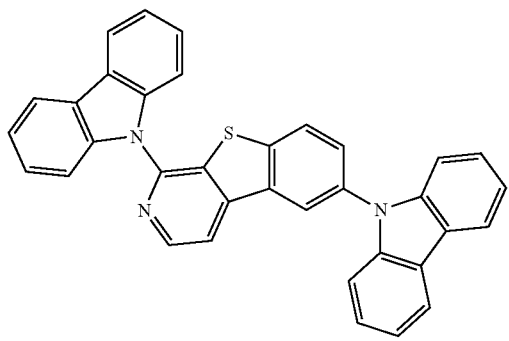

COHost

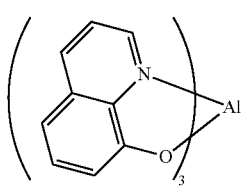

Alq₃

Compound 14

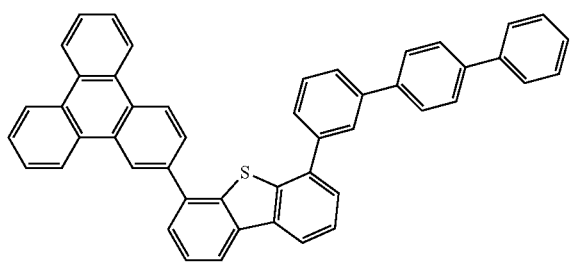

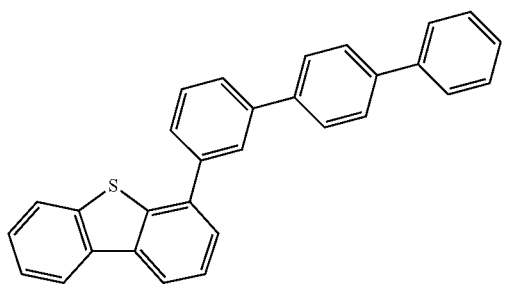

CC-1

Table 1 below is a summary of the relative device data for the Device Example 1, where emission color was recorded at 1000 nits, while the lifetime (LT$_{95}$%) defined as the time required for the device to decay to 95% of its initial luminance was measured at a constant current density of 40 mA/cm$^2$. The device data for Device 1 was normalized on the data for Comparative Device C-1.

TABLE 1

| Device | Host | Color | Relative LT$_{95\%}$ |
|---|---|---|---|
| Comparative Device C-1 | CC-1 | green | 100 |
| Device 1 | Compound 14 | green | 193 |

The data show that Device 1 with inventive Compound 14 as the host material is nearly twice as stable as Comparative Device C-1 with comparative compound CC-1 as the host material.

Device Example 2—A second set of device examples have organic stacks consisting of sequentially, from the ITO surface, 10 nm of LG101 (from LG Chem) as the hole injection layer (HIL), 30 nm of 4,4'-bis[N-(1-naphthyl)-N-phenylaminolbiphenyl (NPD) as the hole-transport layer (HTL), and 25 nm of inventive hosts (Compound 14 and Compound 32) or comparative hosts (CC-2 and CC-3) doped with 10 wt % of Compound A as the emissive layer (EML). On top of the EML, 50 nm of Compound BL was deposited as the hole blocking layer (HBL), followed by 45 nm of tris(8-hydroxyquinolinato)aluminum (Alq$_3$) as the electron-transport layer (ETL). The example devices Device 2 and Device 3 have the inventive Compound 14 and Compound 32, respectively, as hosts. The comparative devices Comparative Device C-2 and Comparative Device C-3 have the comparative compounds CC-2 and CC-3, respectively, as hosts. The structures of the compounds used are shown below.

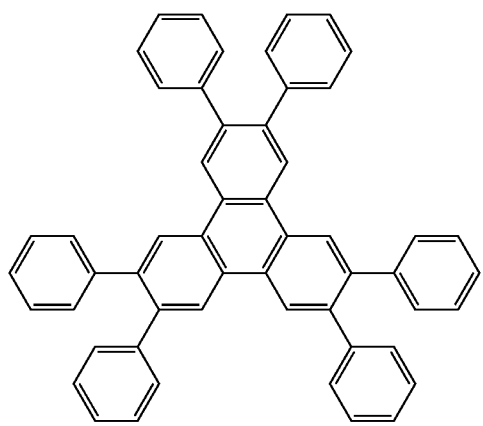
Compound BL
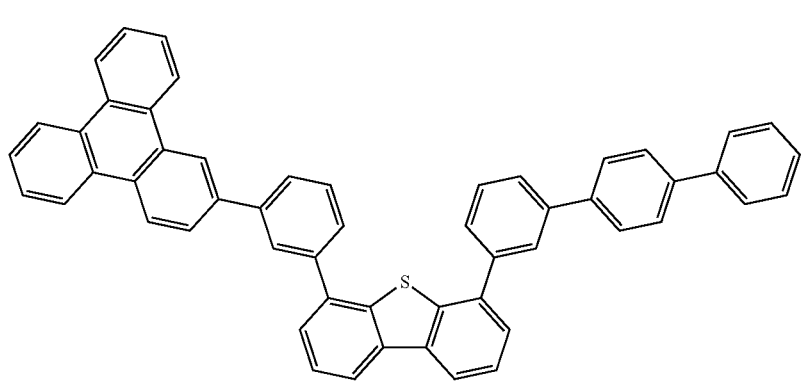
Compound 32
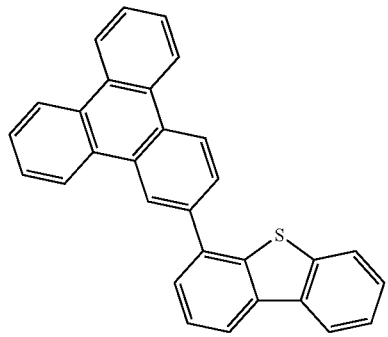
CC-2
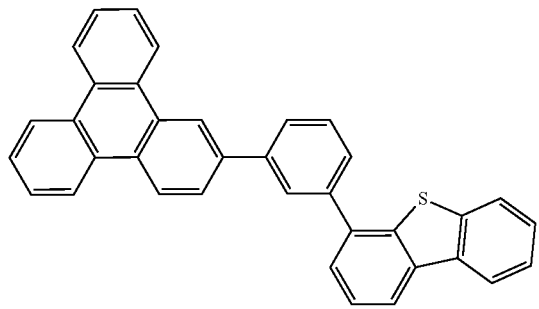
CC-3

Table 2 is a summary of the relative device data for the Device Example 2, where emission color was recorded at 1000 nits, while the lifetime ($LT_{80}\%$), defined as the time required for the device to decay to 80% of its initial luminance, was calculated from the value measured at a constant current density of 40 mA/cm² assuming an acceleration factor of 2. All device data were normalized on those of Comparative Device C-2.

TABLE 2

| Device | Host | Color | Relative $LT_{80\%}$ |
| --- | --- | --- | --- |
| Comparative Device C-2 | CC-2 | green | 100 |
| Device 2 | Compound 14 | green | 106 |
| Comparative Device C-3 | CC-3 | green | 111 |
| Device 3 | Compound 32 | green | 119 |

The data show that the example devices Device 2 and Device 3 with inventive Compounds 14 and 32, respectively, as the host materials are more stable than their corresponding comparative devices Comparative Device C-2 and Comparative Device C-3 with the comparative compounds CC-2 and CC-3, respectively, as the host materials.

Device Example 3: A third set of device examples have the same device structure as those in Device Example 2 except that Compound 32 or CC-4 doped with 15 wt % of Compound A as the emissive layer. The structure of CC-4 is shown below.

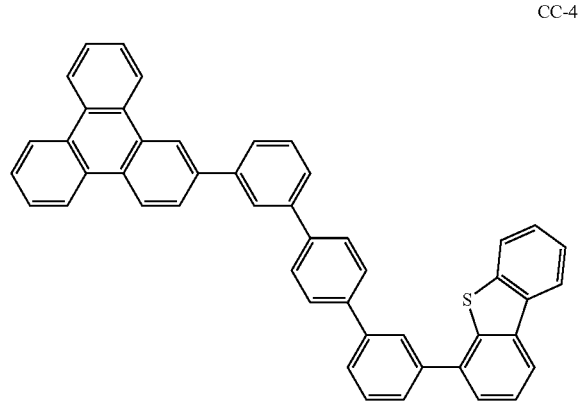 [SMILES: c1cc(-c2ccc(-c3cccc(-c4cccc5c4sc4ccccc45)c3)cc2)cc(-c2ccc3c4ccccc4c4ccccc4c3c2)c1]

CC-4

Table 3 is a summary of the relative device data for the Device Example 3, where emission color was recorded at 1000 nits, while the lifetime ($LT_{80}\%$), defined as the time required for the device to decay to 80% of its initial luminance, was calculated from the value measured at a constant current density of 40 mA/cm² assuming an acceleration factor of 2. The lifetime data ($LT_{80}\%$) were normalized on those of Comparative Device C-4.

TABLE 3

| Device | Host | Color | Relative $LT_{80\%}$ |
| --- | --- | --- | --- |
| Comparative Device C-4 | CC-4 | green | 100 |
| Device 4 | Compound 32 | green | 172 |

The data show that the example device Device 4 using inventive Compound 32 as the host is more stable than Comparative Device C-4 which uses comparative compound CC-4 as the host.

The above device data show that inventive compounds can provide better operation lifetime for OLED devices than the reference compounds reported in the literature. The enhanced device stability might be attributable to improved electron/hole transport balances due to the unique chemical structures of inventive compounds.

COMBINATION WITH OTHER MATERIALS

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

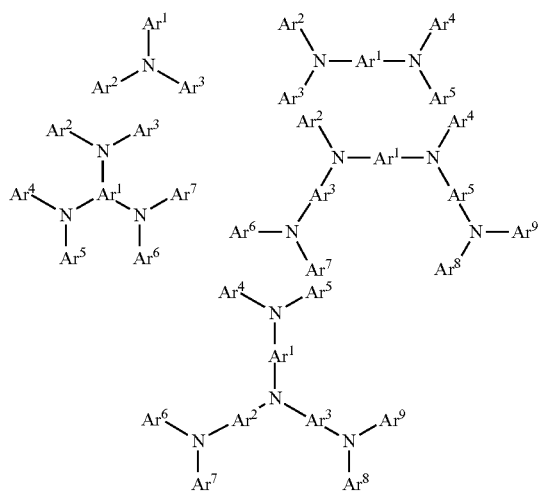

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

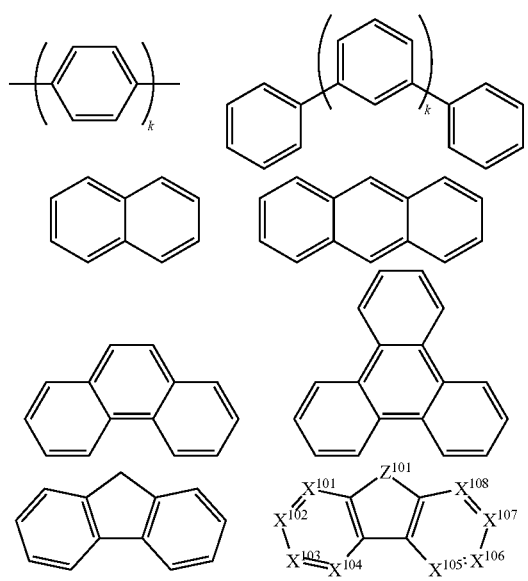

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

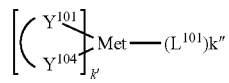

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

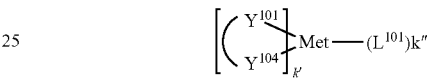

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

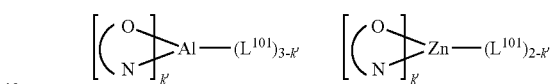

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof.

In one aspect, host compound contains at least one of the following groups in the molecule:

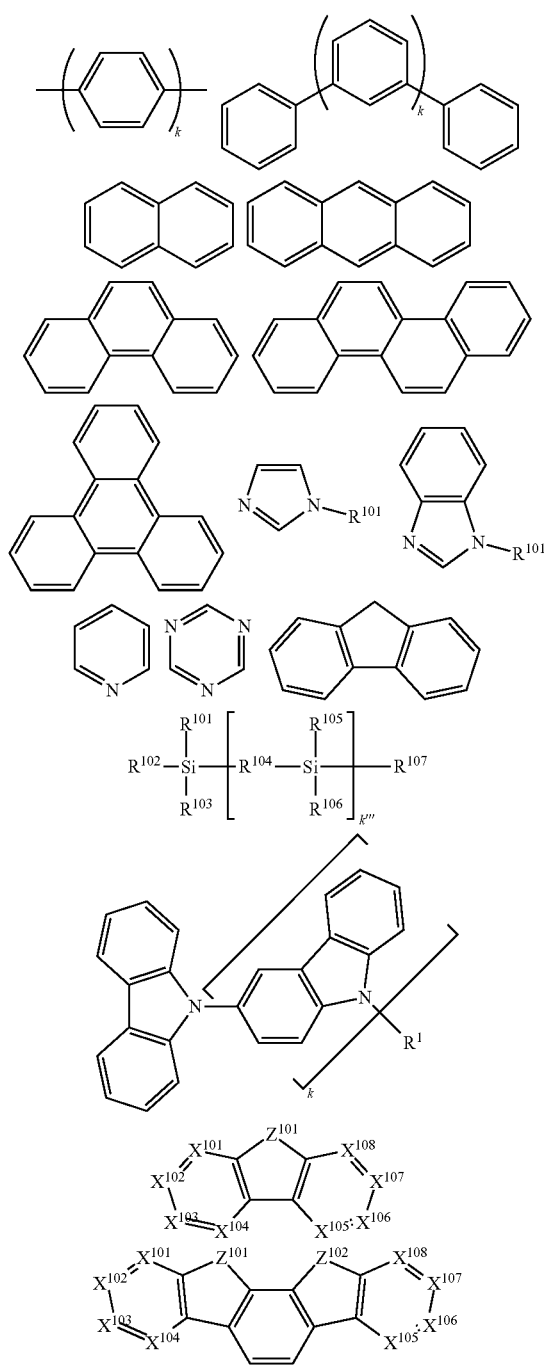

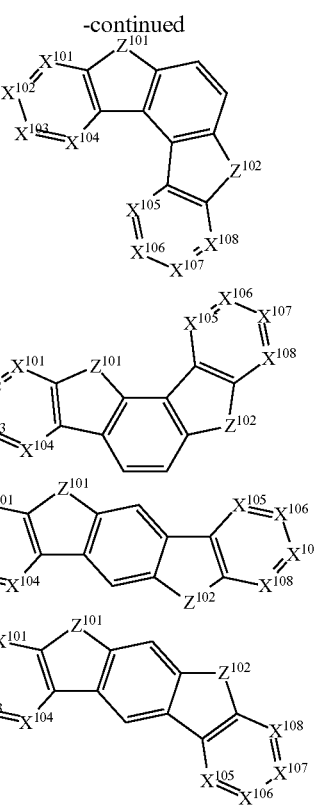

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

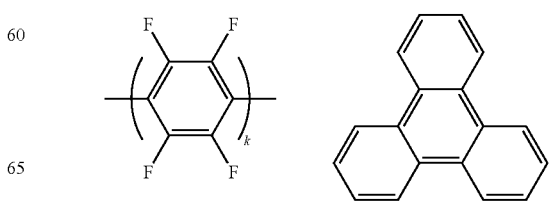

-continued

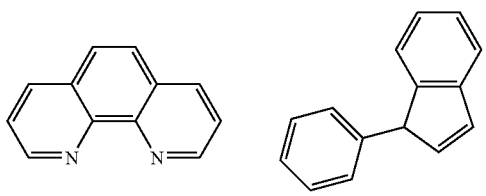

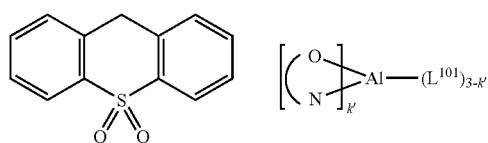

-continued

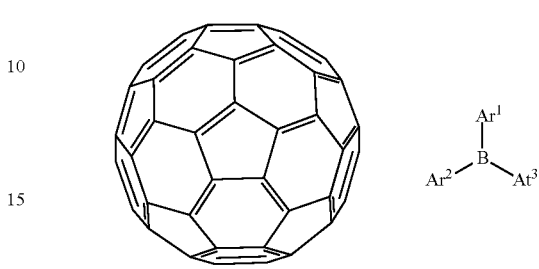

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

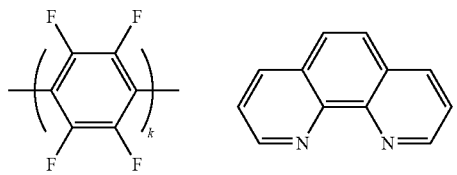

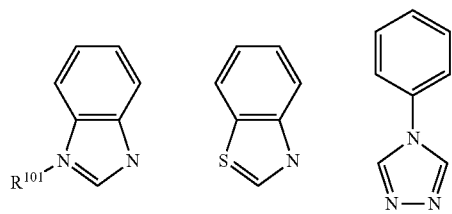

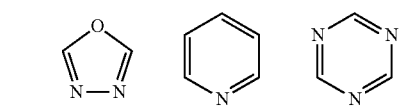

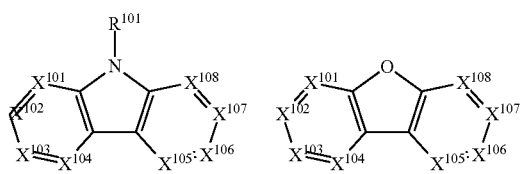

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrite, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula

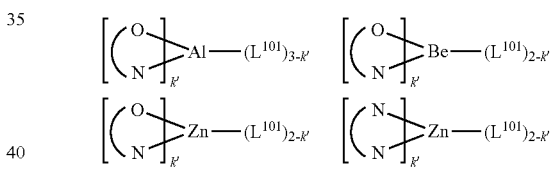

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4
| MATERIAL | EXAMPLES OF MATERIAL | PUBLICATIONS |
|---|---|---|
| Phthalocyanine and porphyrin compounds | 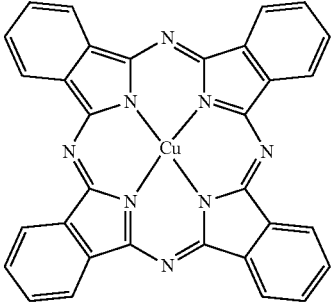 | Appl. Phys. Lett. 69, 2160 (1996) |
| Starburst triarylamines | 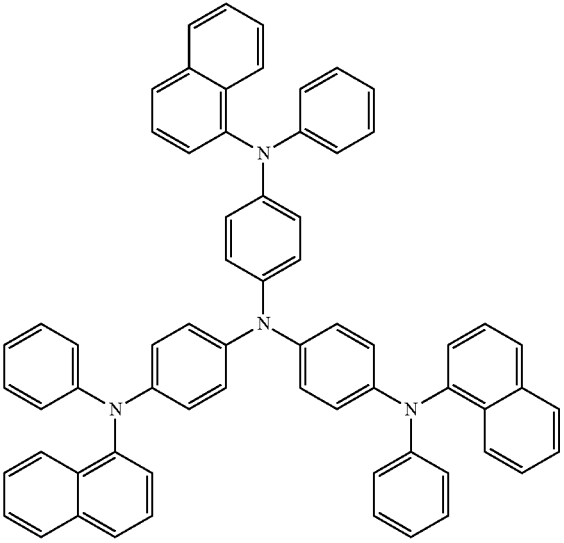 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-\!\!+\!\!CH_xF_y\!\!+\!\!_n$ | Appl. Phys. Lett. 78, 673 (2001) |
| Conducting polymers (e.g., PEDOT:PSS, polyaniline, polythiophene) | 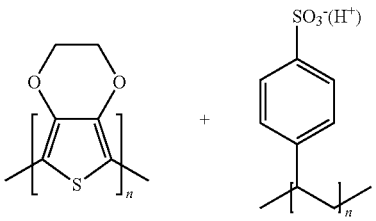 | Synth. Met. 87, 171 (1997) WO2007002683 |
| Phosphonic acid and silane SAMs | 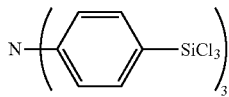 | US20030162053 |

TABLE 4-continued
Hole injection materials
| MATERIAL | EXAMPLES OF MATERIAL | PUBLICATIONS |
| --- | --- | --- |
| Triarylamine or polythiophene polymers with conductivity dopants | 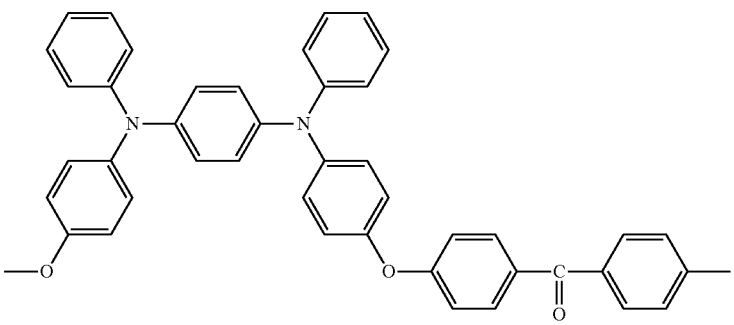 and 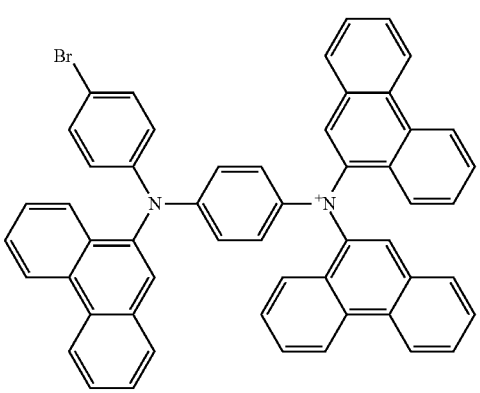 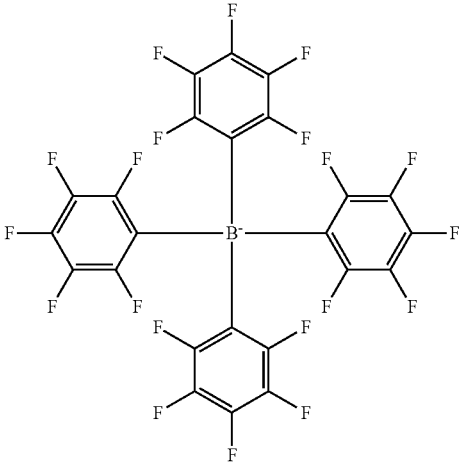 | EP1725079A1 |
| Organic compounds with conductive inorganic compounds, such as molybdenum and tungsten oxides | 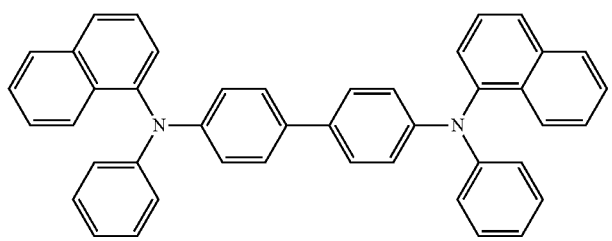 + MoO$_x$ | US20050123751 SID Symposium Digest, 37, 923 (2006) WO2009018009 |

TABLE 4-continued

Hole injection materials

| MATERIAL | EXAMPLES OF MATERIAL | PUBLICATIONS |
| --- | --- | --- |
| n-type semiconducting organic complexes | | US20020158242 |
| Metal organometallic complexes | | US20060240279 |
| Cross-linkable compounds | | US20080220265 |
| Polythiophene based polymers and copolymers | | WO 2011075644<br>EP2350216 |

TABLE 4-continued
Hole injection materials
| MATERIAL | EXAMPLES OF MATERIAL | PUBLICATIONS |
|---|---|---|
| Hole transporting materials | | |
| Triarylamines (e.g., TPD, α-NPD) | 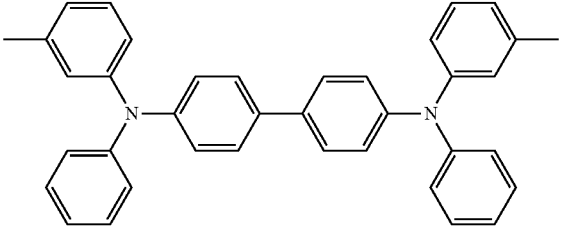 | Appl. Phys. Lett. 51, 913 (1987) |
| | 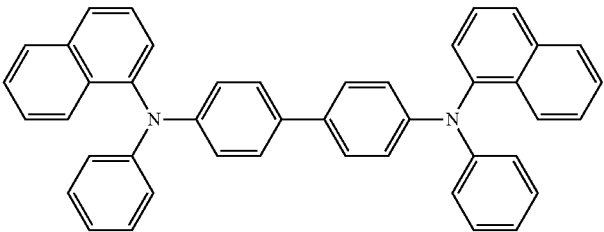 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 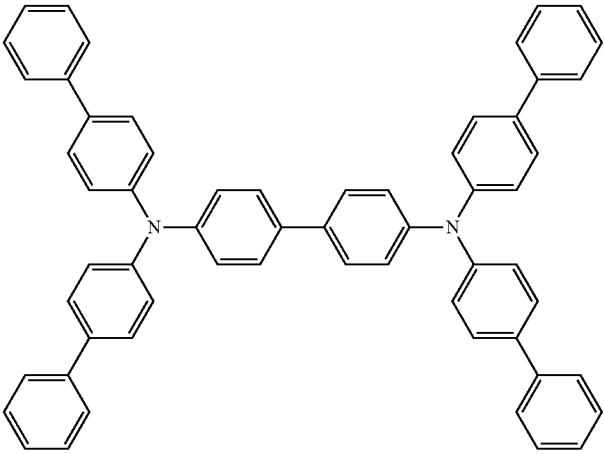 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 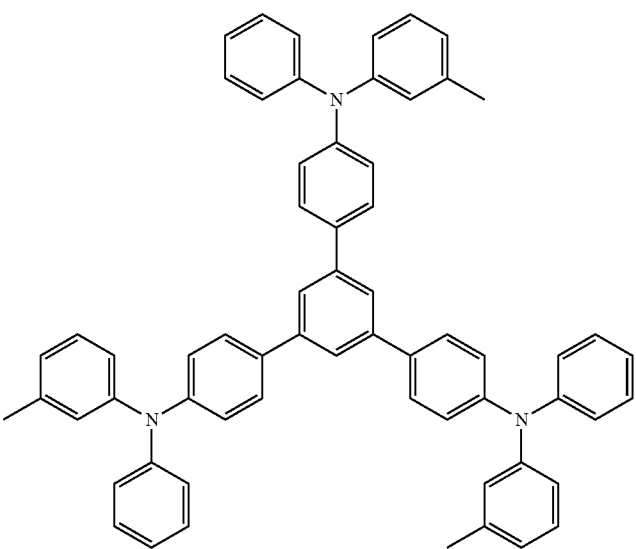 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 4-continued

Hole injection materials

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triarylamine on spirofluorene core | | Synth. Met. 91, 209 (1997) |

TABLE 4-continued
Hole injection materials
| MATERIAL | EXAMPLES OF MATERIAL | PUBLICATIONS |
| --- | --- | --- |
| Arylamine carbazole compounds | 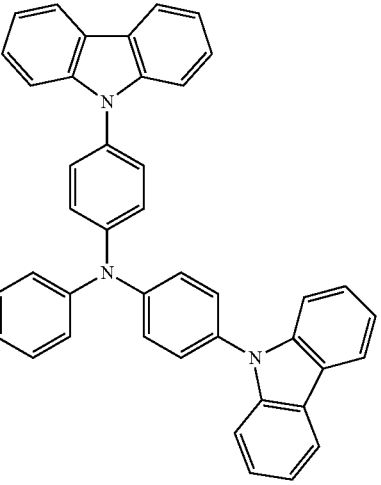 | Adv. Mater. 6, 677 (1994), US20080124572 |
| Triarylamine with (di)benzothiophene/ (di)benzofuran | 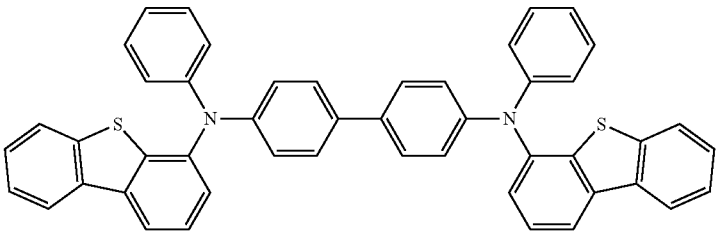 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 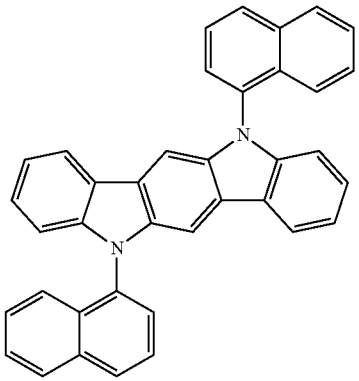 [SMILES: c1ccc2c(-n3c4ccccc4c4cc5c(cc43)c3ccccc3n5-c3cccc4ccccc34)cccc2c1] | Synth. Met. 111, 421 (2000) |

TABLE 4-continued

Hole injection materials

| MATERIAL | EXAMPLES OF MATERIAL | PUBLICATIONS |
| --- | --- | --- |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |

TABLE 4-continued
Hole injection materials
| MATERIAL | EXAMPLES OF MATERIAL | PUBLICATIONS |
|---|---|---|
| | 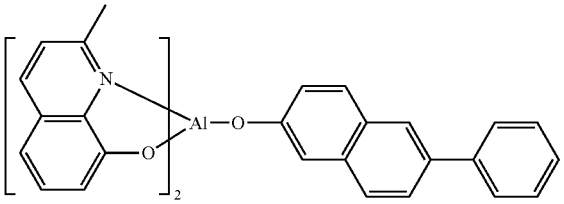 | WO2005014551 |
| | 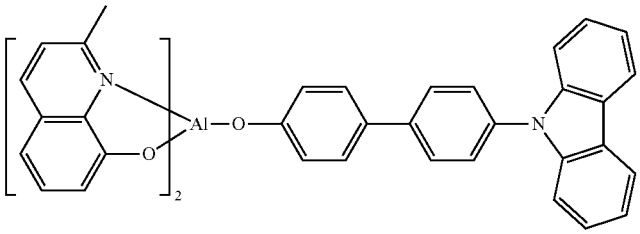 | WO2006072002 |
| Metal phenoxybenzothiazole compounds | 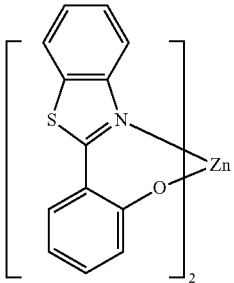 | Appl. Phys. Lett. 90, 123509 (2007) |
| Conjugated oligomers and polymers (e.g., polyfluorene) | 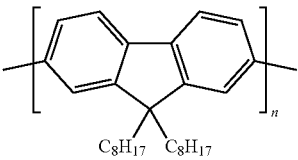 | Org. Electron. 1, 15 (2000) |
| Aromatic fused rings | 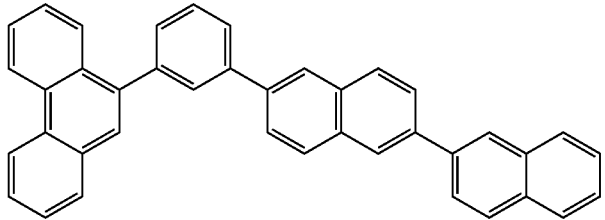 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 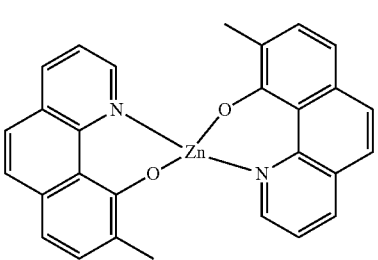 | WO2010056066 |

TABLE 4-continued

Hole injection materials

| MATERIAL | EXAMPLES OF MATERIAL | PUBLICATIONS |
|---|---|---|
| Chrysene based compounds | | WO2011086863 |

Green hosts

| | | |
|---|---|---|
| Arylcarbazoles | | Appl. Phys. Lett. 78, 1622 (2001) |
| | | US20030175553 |
| | | WO2001039234 |
| Aryltriphenylene compounds | | US20060280965 |

TABLE 4-continued
Hole injection materials
| MATERIAL | EXAMPLES OF MATERIAL | PUBLICATIONS |
| --- | --- | --- |
| | 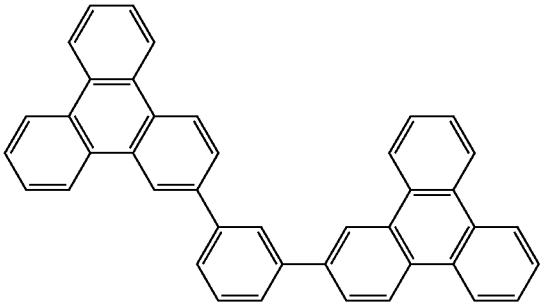 [SMILES: c1cc(-c2ccc3c4ccccc4c4ccccc4c3c2)cc(-c2ccc3c4ccccc4c4ccccc4c3c2)c1] | US20060280965 |
| | 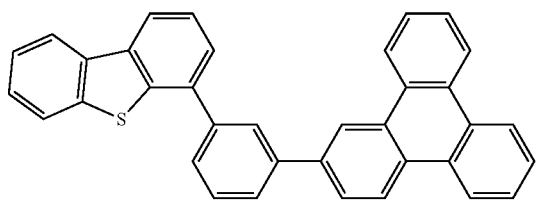 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 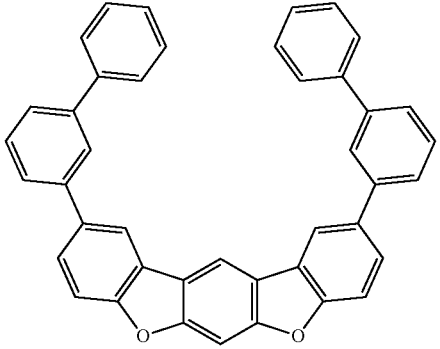 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 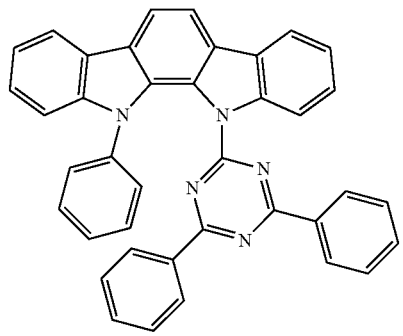 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 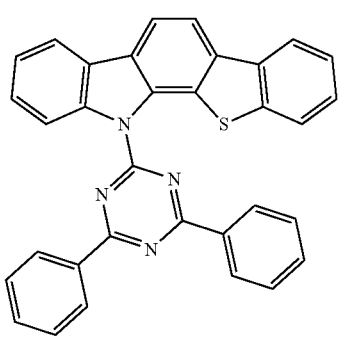 [SMILES: c1ccc(-c2nc(-c3ccccc3)nc(-n3c4ccccc4c4ccc5c6ccccc6sc5c43)n2)cc1] | WO2010107244 |

TABLE 4-continued

| | Hole injection materials | |
|---|---|---|
| MATERIAL | EXAMPLES OF MATERIAL | PUBLICATIONS |
| Aza-carbazole/DBT/ DBF | | JP2008074939 |
| | | US20100187984 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |

TABLE 4-continued

| | Hole injection materials | |
|---|---|---|
| MATERIAL | EXAMPLES OF MATERIAL | PUBLICATIONS |
| | | WO2006132173 |
| | | JP200511610 |
| Spirofluorene-carbazole compounds | | JP2007254297 |
| | | JP2007254297 |

TABLE 4-continued

| | Hole injection materials | |
|---|---|---|
| MATERIAL | EXAMPLES OF MATERIAL | PUBLICATIONS |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 4-continued

| Hole injection materials | | |
|---|---|---|
| MATERIAL | EXAMPLES OF MATERIAL | PUBLICATIONS |
| Metal phenoxypyridine compounds | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 4-continued
| | Hole injection materials | |
|---|---|---|
| MATERIAL | EXAMPLES OF MATERIAL | PUBLICATIONS |
| | 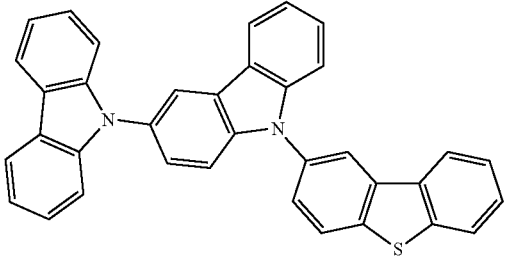 [SMILES: c1ccc2c(c1)sc1ccc(-n3c4ccccc4c4cc(-n5c6ccccc6c6ccccc65)ccc43)cc12] | WO2009086028 |
| | 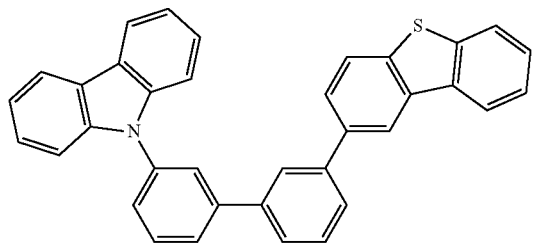 [SMILES: c1cc(-c2cccc(-n3c4ccccc4c4ccccc43)c2)cc(-c2ccc3sc4ccccc4c3c2)c1] | US20090030202, US20090017330 |
| | 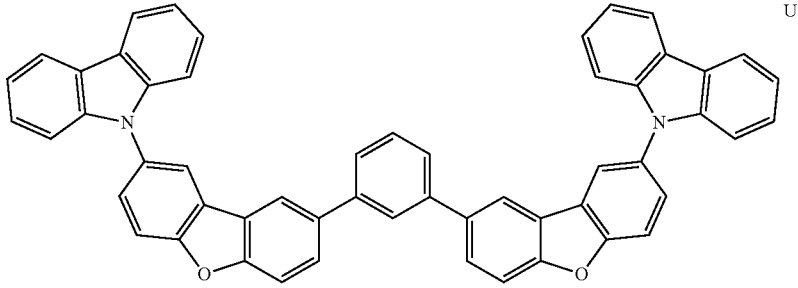 | US20100084966 |
| Silicon aryl compounds | 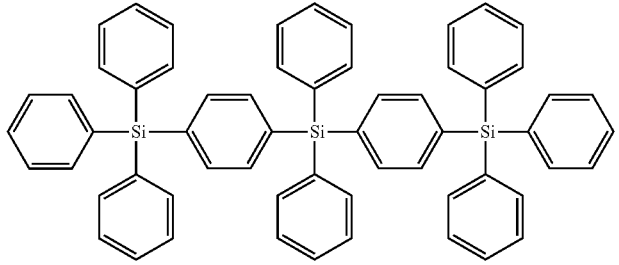 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 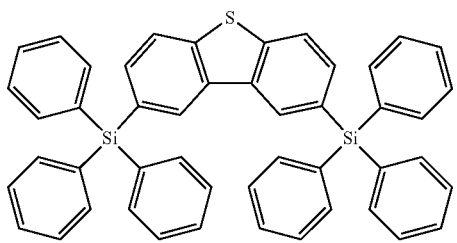 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 4-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

| | TABLE 4-continued | |
|---|---|---|
| | Hole injection materials | |
| MATERIAL | EXAMPLES OF MATERIAL | PUBLICATIONS |
| | Phosphorescent dopants | |
| | Red dopants | |
| Heavy metal porphyrins (e.g., PtOEP) | 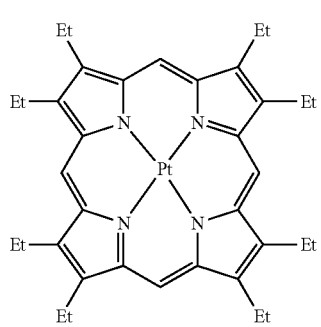 | Nature 395, 151 (1998) |
| Iridium(III) organometallic complexes | 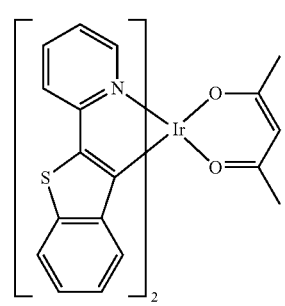 | Appl. Phys. Lett. 78, 1622 (2001) |
| | 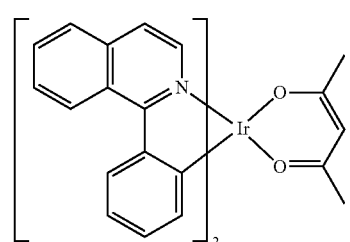 | US2006835469 |
| | 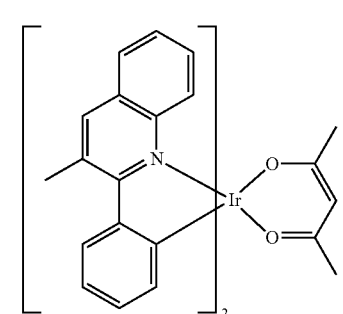 | US2006835469 |
| | 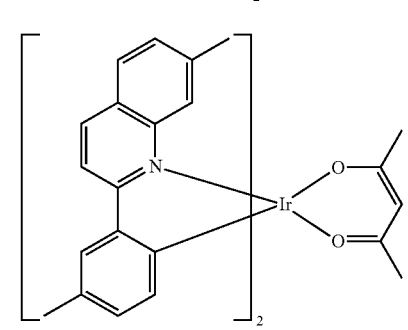 | US20060202194 |

TABLE 4-continued
Hole injection materials
| MATERIAL | EXAMPLES OF MATERIAL | PUBLICATIONS |
|---|---|---|
| | 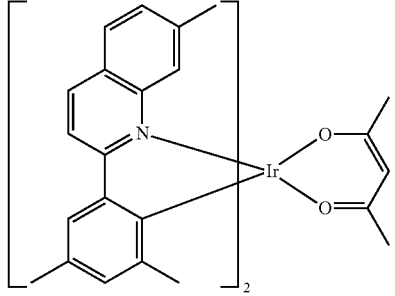 | US20060202194 |
| | 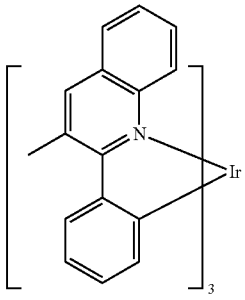 | US20070087321 |
| | 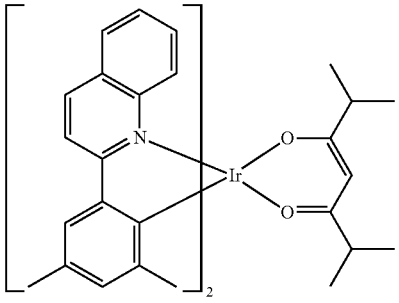 | US20080261076<br>US20100090591 |
| | 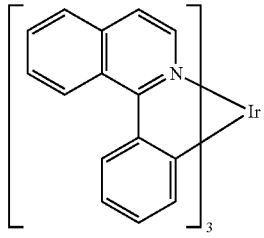 | US20070087321 |
| | 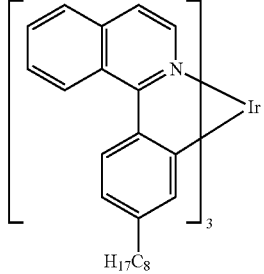 | Adv. Mater. 19, 739 (2007) |

TABLE 4-continued

Hole injection materials

| MATERIAL | EXAMPLES OF MATERIAL | PUBLICATIONS |
| --- | --- | --- |
| | | WO2009100991 |
| | | WO2008101842 |
| | | U.S. Pat. No. 7,232,618 |
| Platinum(II) organometallic complexes | | WO2003040257 |
| | | US20070103060 |

TABLE 4-continued

Hole injection materials

| MATERIAL | EXAMPLES OF MATERIAL | PUBLICATIONS |
| --- | --- | --- |
| Osminum(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |

Green dopants

| | | |
| --- | --- | --- |
| Iridium(III) organometallic complexes | and its derivatives | Inorg. Chem. 40, 1704 (2001) |
| | | US20020034656 |

TABLE 4-continued

Hole injection materials

| MATERIAL | EXAMPLES OF MATERIAL | PUBLICATIONS |
|---|---|---|
| | | U.S. Pat. No. 7,332,232 |
| | | US20090108737 |
| | | WO2010028151 |

TABLE 4-continued

| | Hole injection materials | |
|---|---|---|
| MATERIAL | EXAMPLES OF MATERIAL | PUBLICATIONS |
| | | EP1841834B |
| | | US20060127696 |
| | | US20090039776 |
| | | U.S. Pat. No. 6,921,915 |
| | | US20100244004 |

TABLE 4-continued

Hole injection materials

| MATERIAL | EXAMPLES OF MATERIAL | PUBLICATIONS |
| --- | --- | --- |
| | | U.S. Pat. No. 6,687,266 |
| | | Chem. Mater. 16, 2480 (2004) |
| | | US20070190359 |
| | | US 20060008670 JP2007123392 |
| | | WO2010086089, WO2011044988 |
| | | Adv. Mater. 16, 2003 (2004) |

TABLE 4-continued
Hole injection materials
| MATERIAL | EXAMPLES OF MATERIAL | PUBLICATIONS |
|---|---|---|
| | 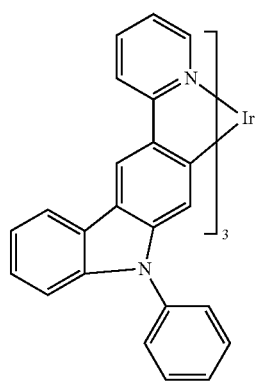 | Angew. Chem. Int. Ed. 2006, 45, 7800 |
| | 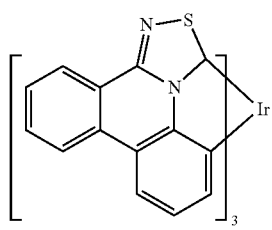 | WO2009050290 |
| | 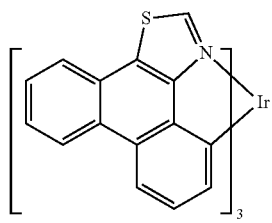 | US20090165846 |
| | 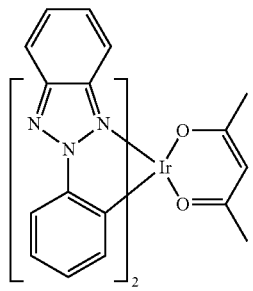 | US2008015355 |
| | 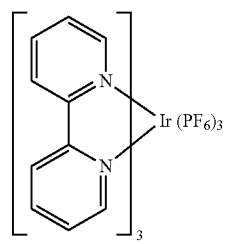 | US20010015432 |

TABLE 4-continued

Hole injection materials

| MATERIAL | EXAMPLES OF MATERIAL | PUBLICATIONS |
| --- | --- | --- |
| | | US20100295032 |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |

TABLE 4-continued

Hole injection materials

| MATERIAL | EXAMPLES OF MATERIAL | PUBLICATIONS |
|---|---|---|
| | | Chem. Lett. 34, 592 (2005) |
| | | WO2002015645 |
| | | US20060263635 |
| | | US20060182992<br>US20070103060 |

TABLE 4-continued
Hole injection materials
| MATERIAL | EXAMPLES OF MATERIAL | PUBLICATIONS |
|---|---|---|
| Cu complexes | 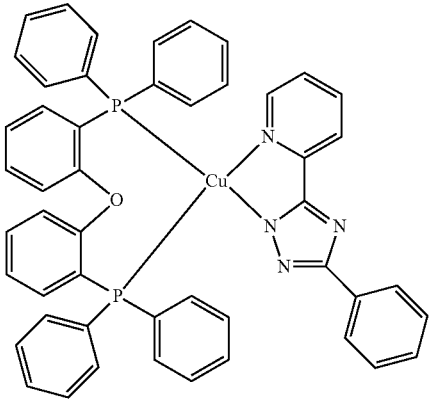 | WO2009000673 |
|  | 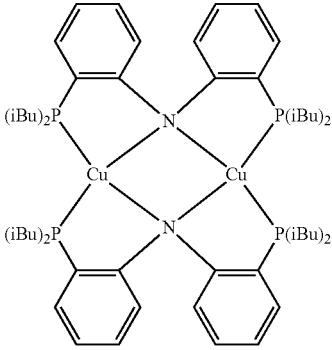 | US20070111026 |
| Gold complexes | 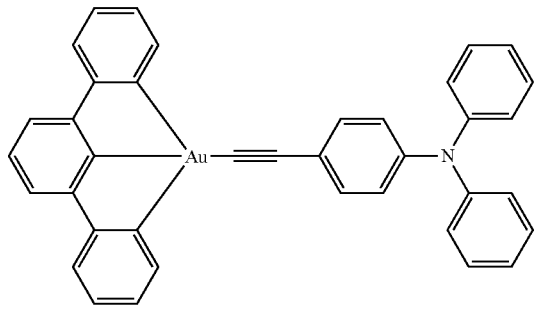 | Chem. Commun. 2906 (2005) |
| Rhenium(III) complexes | 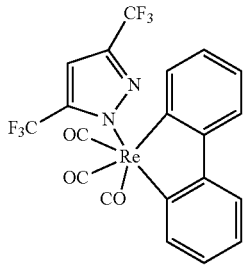 | Inorg. Chem. 42, 1248 (2003) |

TABLE 4-continued

Hole injection materials

| MATERIAL | EXAMPLES OF MATERIAL | PUBLICATIONS |
| --- | --- | --- |
| Osmium(II) complexes | | U.S. Pat. No. 7,279,704 |
| Deuterated organometallic complexes | | US20030138657 |
| Organometallic complexes with two or more metal centers | | US20030152802 |

TABLE 4-continued

| | Hole injection materials | |
|---|---|---|
| MATERIAL | EXAMPLES OF MATERIAL | PUBLICATIONS |
| | [Pt complex structure] | U.S. Pat. No. 7,090,928 |
| | Blue dopants | |
| Iridium(III) organometallic complexes | [Ir complex with difluorophenylpyridine and picolinate] | WO2002002714 |
| | [Ir complex with imidazole-phenyl ligand] | WO2006009024 |
| | [Ir complex with dimethylphenyl-imidazole ligand] | US20060251923<br>US20110057559<br>US20110204333 |
| | [Ir complex with N-methylimidazole ligand] | U.S. Pat. No. 7,393,599,<br>WO2006056418,<br>US20050260441,<br>WO2005019373 |

TABLE 4-continued

Hole injection materials

| MATERIAL | EXAMPLES OF MATERIAL | PUBLICATIONS |
| --- | --- | --- |
| | | U.S. Pat. No. 7,534,505 |
| | | WO2011051404 |
| | | U.S. Pat. No. 7,445,855 |
| | | US20070290359, US20080297033 US20100148663 |

TABLE 4-continued

| | Hole injection materials | |
|---|---|---|
| MATERIAL | EXAMPLES OF MATERIAL | PUBLICATIONS |
| | | U.S. Pat. No. 7,338,722 |
| | | US20020134984 |
| | | Angew. Chem. Int. Ed. 47, 4542 (2008) |
| | | Chem. Mater. 18, 5119 (2006) |
| | | Inorg. Chem. 46, 4308 (2007) |

TABLE 4-continued

Hole injection materials

| MATERIAL | EXAMPLES OF MATERIAL | PUBLICATIONS |
| --- | --- | --- |
| | | WO2005123873 |
| | | WO2005123873 |
| | | WO2007004380 |
| | | WO2006082742 |
| Osmium(II) complexes | | U.S. Pat. No. 7,279,704 |

TABLE 4-continued

| | Hole injection materials | |
|---|---|---|
| MATERIAL | EXAMPLES OF MATERIAL | PUBLICATIONS |
| | | Organometallics 23, 3745 (2004) |
| Gold complexes | | Appl. Phys. Lett. 74, 1361 (1999) |
| Platinum(II) complexes | | WO2006098120, WO2006103874 |
| Pt tetradentate complexes with at least one metal-carbene bond | | U.S. Pat. No. 7,655,323 |
| | Exciton/hole blocking layer materials | |
| Bathocuprine compounds (e.g., BCP, BPhen) | | Appl. Phys. Lett. 75, 4 (1999) |
| | | Appl. Phys. Lett. 79, 449 (2001) |

TABLE 4-continued
Hole injection materials
| MATERIAL | EXAMPLES OF MATERIAL | PUBLICATIONS |
|---|---|---|
| Metal 8-hydroxyquinolates (e.g., BAlq) | 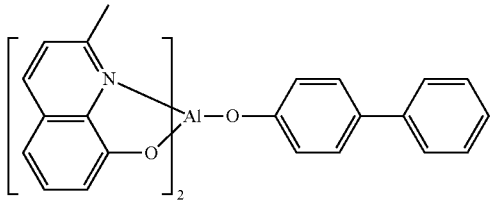 | Appl. Phys. Lett. 81, 162 (2002) |
| 5-member ring electron deficient heterocycles such as triazole, oxadiazole, imidazole, benzoimidazole | 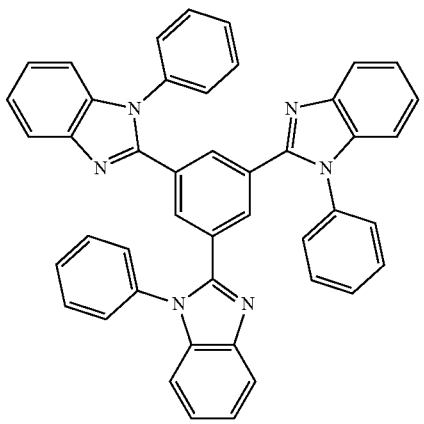 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 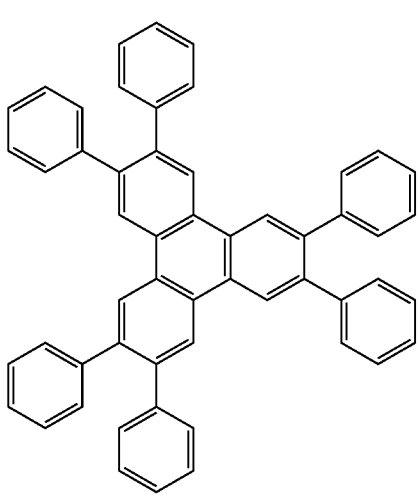 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 4-continued
Hole injection materials
| MATERIAL | EXAMPLES OF MATERIAL | PUBLICATIONS |
|---|---|---|
| Fluorinated aromatic compounds | 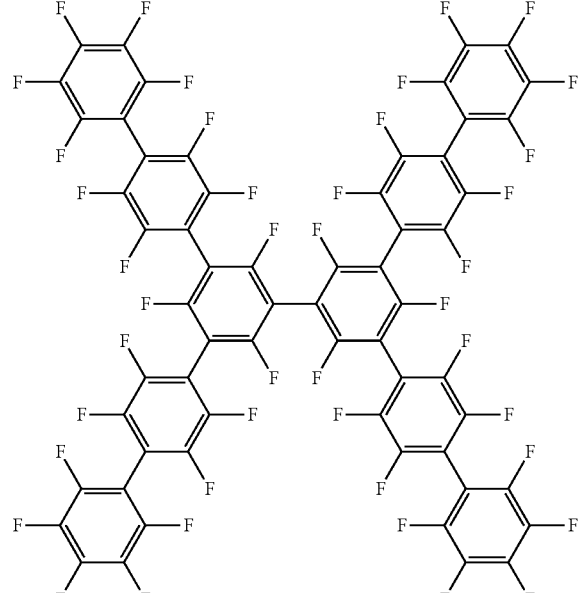 | Appl. Phys. Lett. 79, 156 (2001) |
| Phenothiazine-S-oxide | 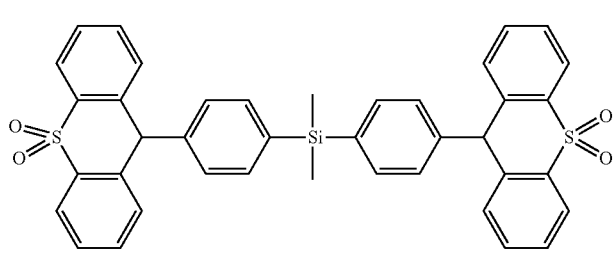 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 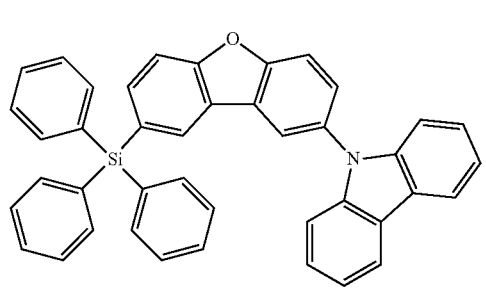 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 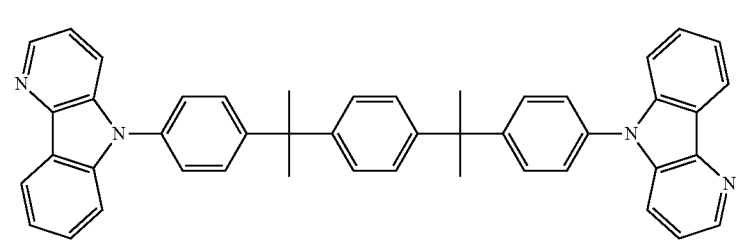 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE 4-continued
Hole injection materials
| MATERIAL | EXAMPLES OF MATERIAL | PUBLICATIONS |
|---|---|---|
| Electron transporting materials | | |
| Anthracene-benzoimidazole compounds | 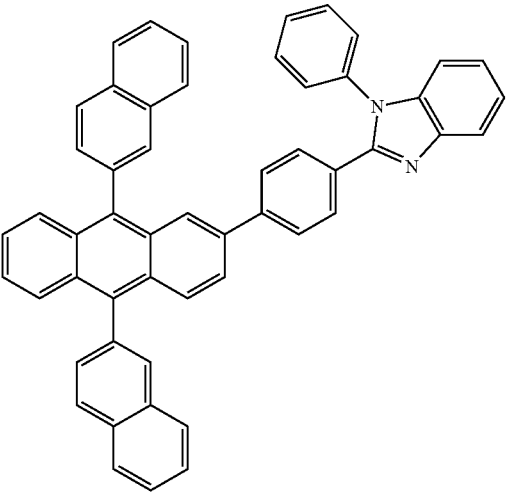 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 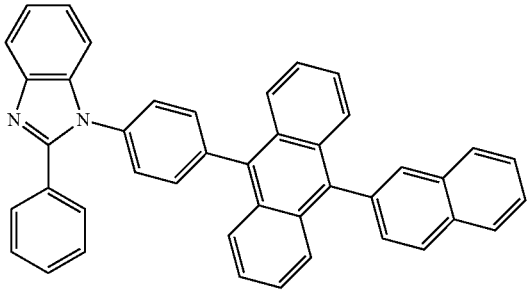 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 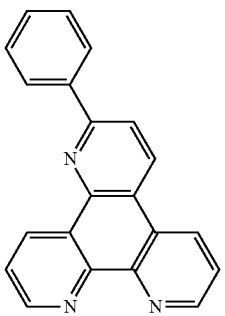 [SMILES: c1ccc(-c2ccc3c4cccnc4c4ncccc4c3n2)cc1] | US20090115316 |
| Anthracene-benzothiazole compounds | 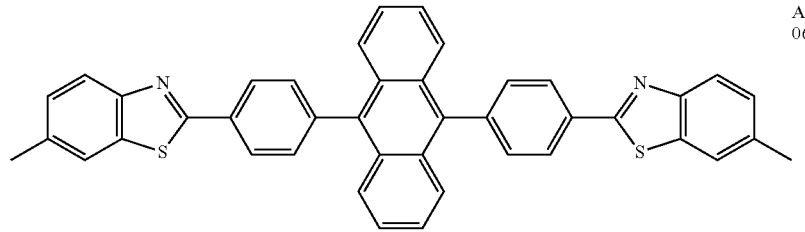 | Appl. Phys. Lett. 89, 063504 (2006) |

TABLE 4-continued

| | Hole injection materials | |
|---|---|---|
| MATERIAL | EXAMPLES OF MATERIAL | PUBLICATIONS |
| Metal 8-hydroxyquinolates (e.g., Alq3, Zrq4) | | Appl. Phys. Lett. 51, 913 (1987) U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE 4-continued
Hole injection materials
| MATERIAL | EXAMPLES OF MATERIAL | PUBLICATIONS |
|---|---|---|
| | 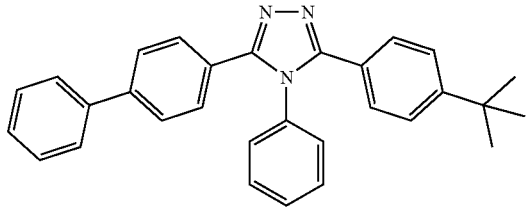 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 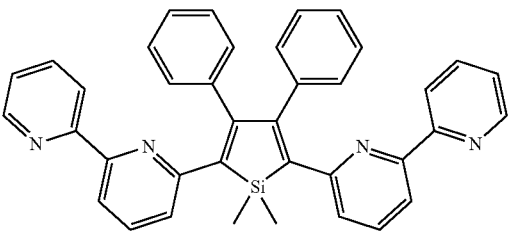 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 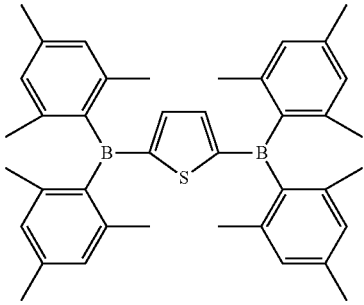 | J. Am. Chem. Soc. 120, 9714 (1998) |
| Fluorinated aromatic compounds | 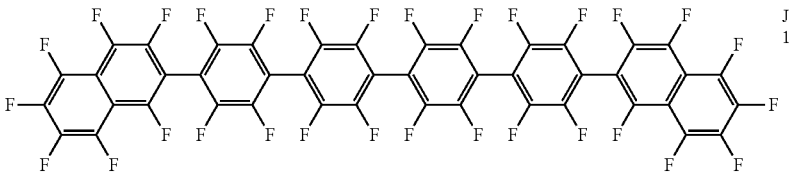 | J. Am. Chem. Soc. 122, 1832 (2000) |
| Fullerene (e.g., C60) | 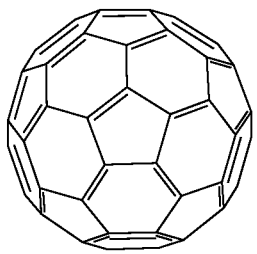 | US20090101870 |

TABLE 4-continued

Hole injection materials

| MATERIAL | EXAMPLES OF MATERIAL | PUBLICATIONS |
|---|---|---|
| Triazine complexes | | US20040036077 |
| Zn (N^N) complexes | | U.S. Pat. No. 6,528,187 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having a structure according to a formula (I)

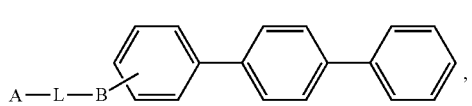

wherein A is selected from a group consisting of triphenylene, phenanthrene, anthracene, biphenyl, terphenyl, carbazole, dibenzothiophene, dibenzofuran, dibenzoselenophene, fluorene, azatriphenylene, azacarbazole, azadibenzothiophene, azadibenzofuran, azadibenzoselenophene, triazine, or combinations thereof;
wherein L is selected from a group consisting of a direct bond, benzene, biphenyl and terphenyl, pyridine, or combinations thereof, and wherein L is optionally further substituted with alkyl, halogen, hydrogen, deuterium, nitrite or aryl;
wherein B is selected from a group consisting of dibenzothiophene, dibenzofuran and dibenzoselenophene; and
wherein A and B are independently optionally further substituted with one or more substituents selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and for each of A and B, two adjacent substituents are optionally joined to form a ring.

2. The compound of claim 1, wherein the compound is of formula (II) or (III)

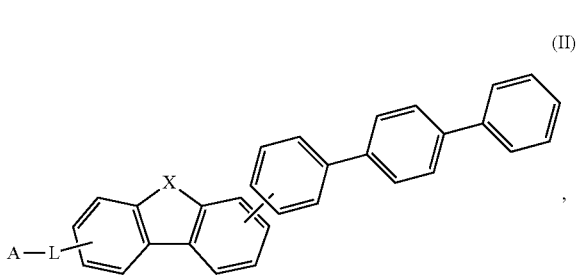

wherein X is selected from a group consisting of O, S and Se.

3. The compound of claim 1, wherein A is selected from the group consisting of

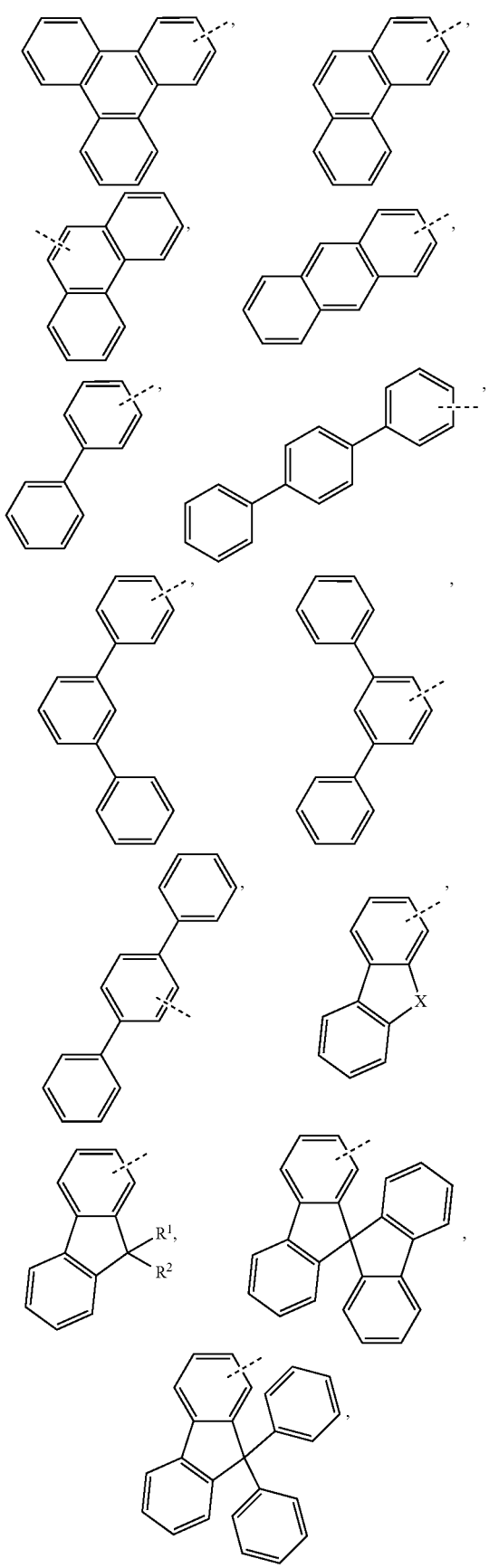
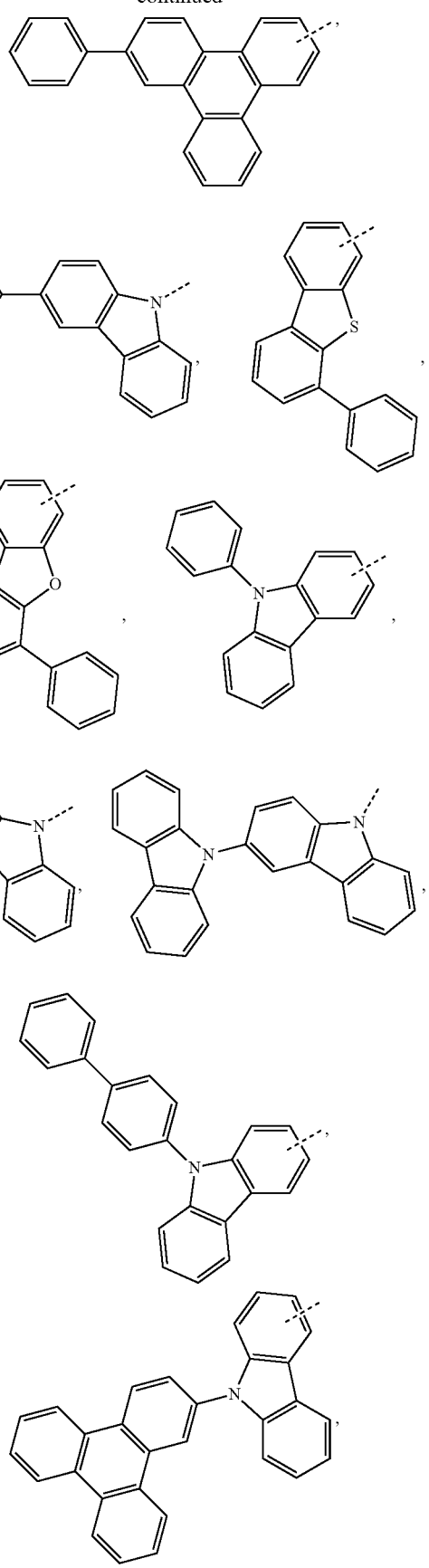

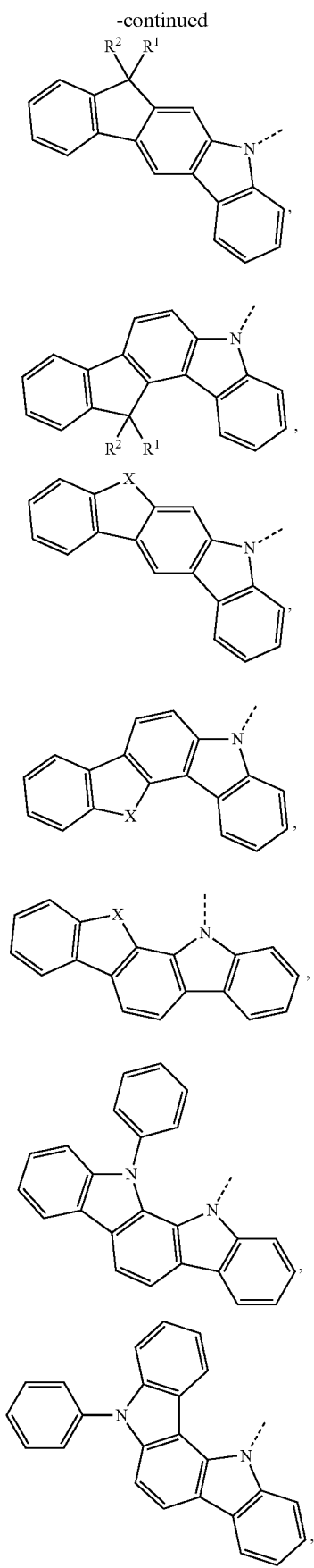
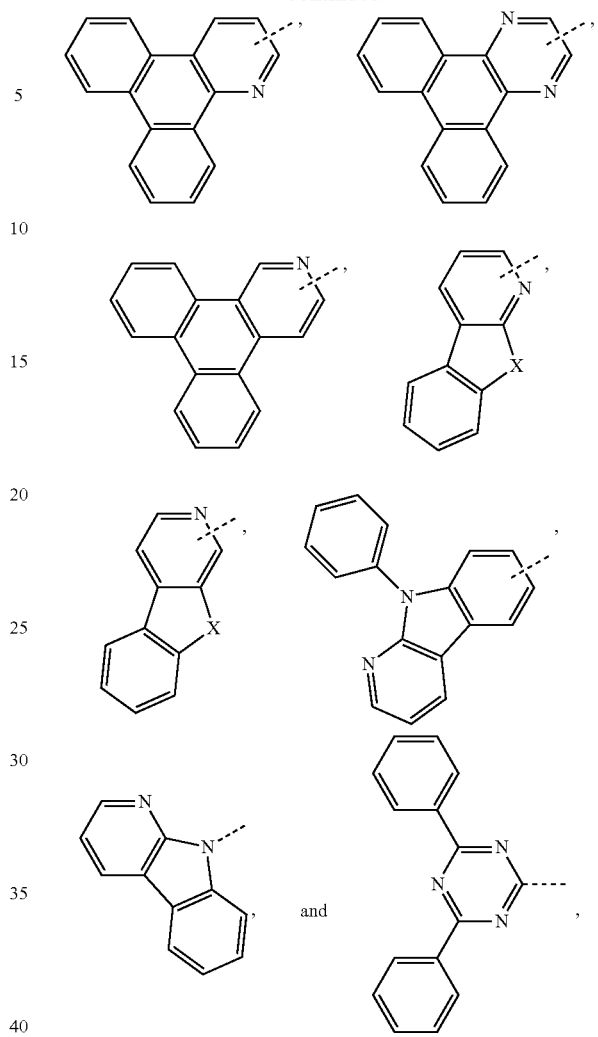
wherein X is S, O or Se; and
R¹ and R² are, independently, linear or branched alkyl with 1 to 12 carbon atoms, and R¹ and R² are optionally jointed to form a ring.
4. The compound of claim 1, wherein B is selected from the group consisting of
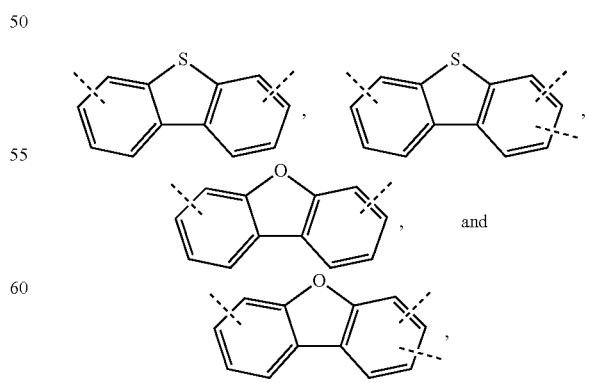
5. The compound of claim 1, wherein L is selected from the group consisting of a direct bond,

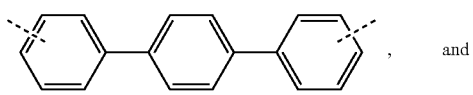

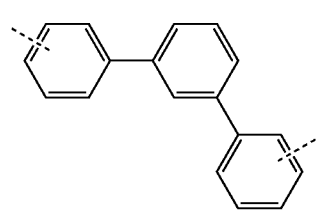

and

6. The compound of claim 1, wherein the compound is selected from the group consisting of

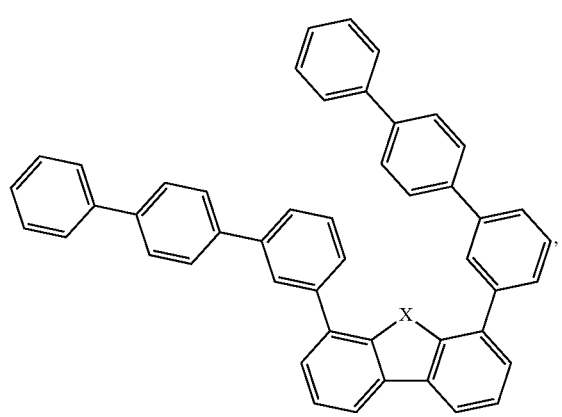

Compound 1, wherein X=O,
Compound 2, wherein X=S,
Compound 3, wherein X=Se,

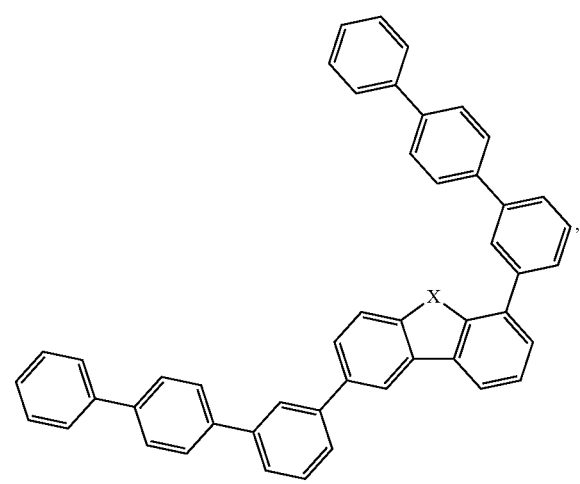

Compound 4, wherein X=O,
Compound 5, wherein X=S,
Compound 6, wherein X=Se,

-continued

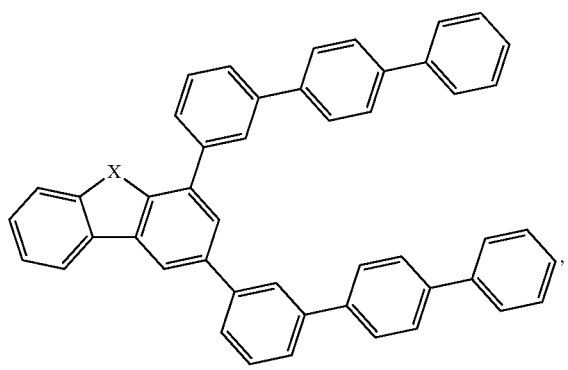

Compound 7, wherein X=O,
Compound 8, wherein X=S,
Compound 9, wherein X=Se,

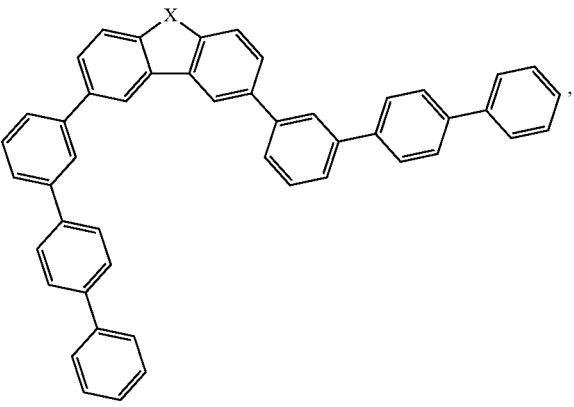

Compound 10, wherein X=O,
Compound 11, wherein X=S,
Compound 12, wherein X=Se,

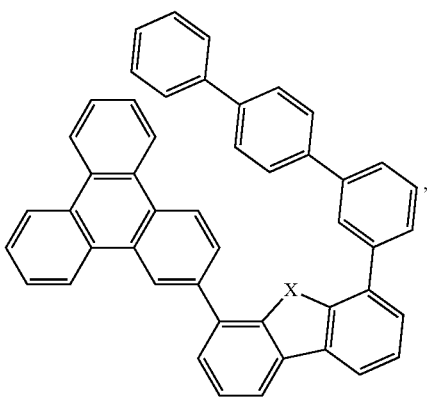

Compound 13, wherein X=O,
Compound 14, wherein X=S,
Compound 15, wherein X=Se,

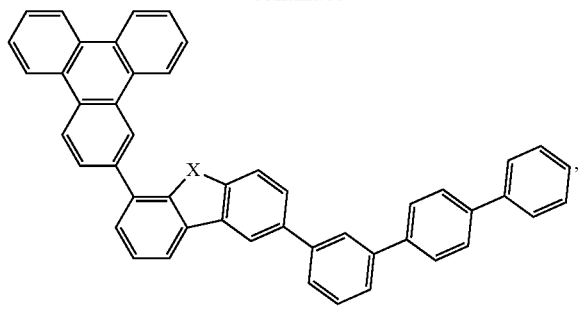

Compound 16, wherein X=O,
Compound 17, wherein X=S,
Compound 18, wherein X=Se,

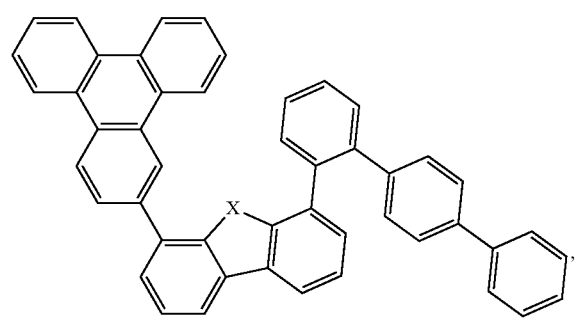

Compound 19, wherein X=O,
Compound 20, wherein X=S,
Compound 21, wherein X=Se,

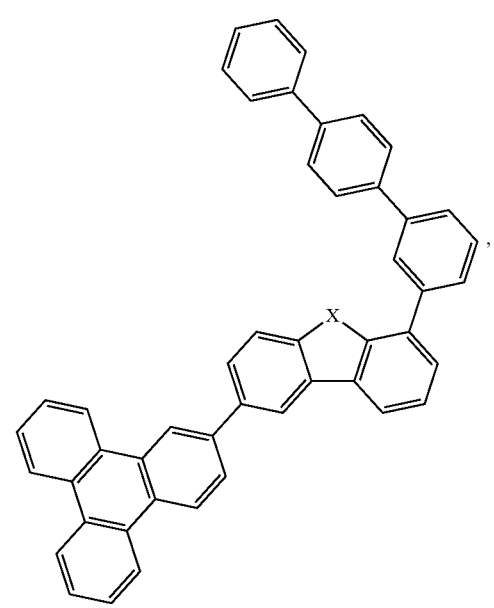

Compound 22, wherein X=O,
Compound 23, wherein X=S,
Compound 24, wherein X=Se,

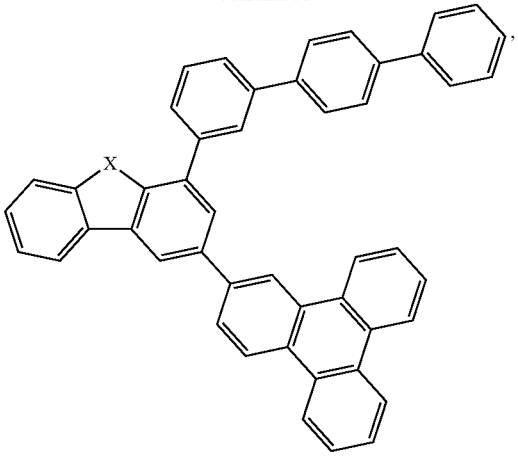

Compound 25, wherein X=O,
Compound 26, wherein X=S,
Compound 27, wherein X=Se,

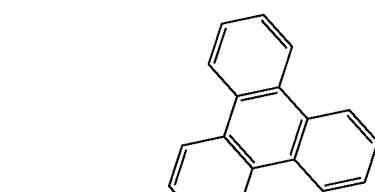

Compound 28, wherein X=O,
Compound 29, wherein X=S,
Compound 30, wherein X=Se,

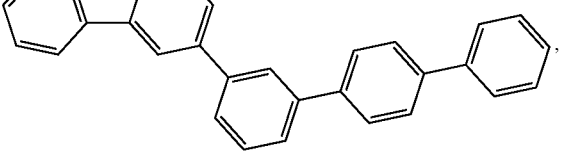

Compound 31, wherein X=O,
Compound 32, wherein X=S,
Compound 33, wherein X=Se,

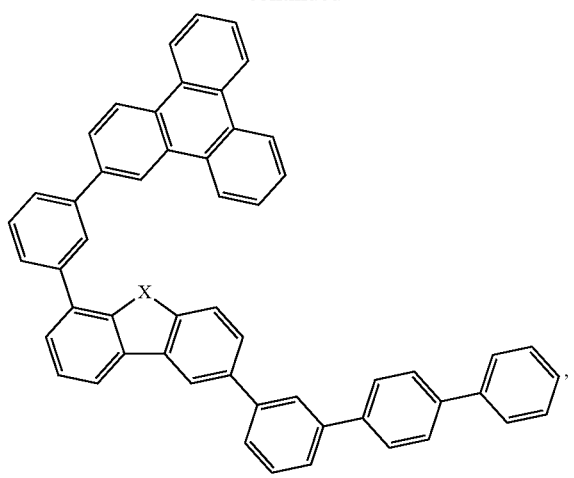

Compound 34, wherein X=O,
Compound 35, wherein X=S,
Compound 36, wherein X=Se,

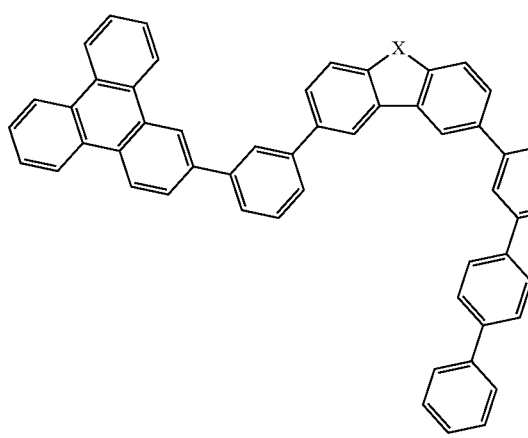

Compound 37, wherein X=O,
Compound 38, wherein X=S,
Compound 39, wherein X=Se,

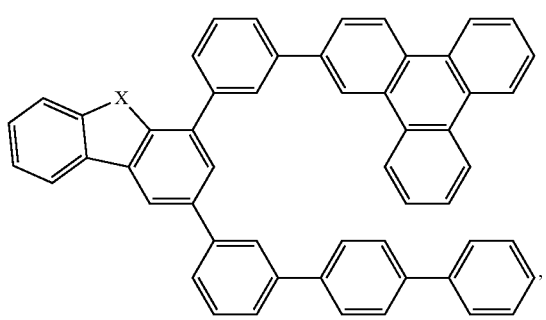

Compound 40, wherein X=O,
Compound 41, wherein X=S,
Compound 42, wherein X=Se,

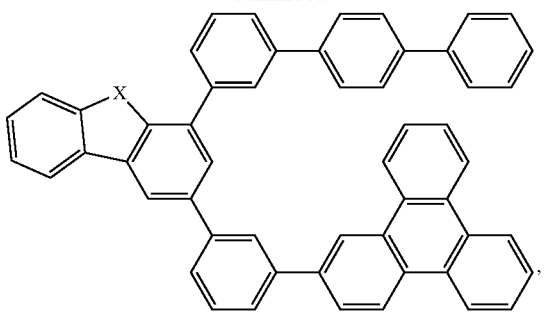

Compound 43, wherein X=O,
Compound 44, wherein X=S,
Compound 45, wherein X=Se,

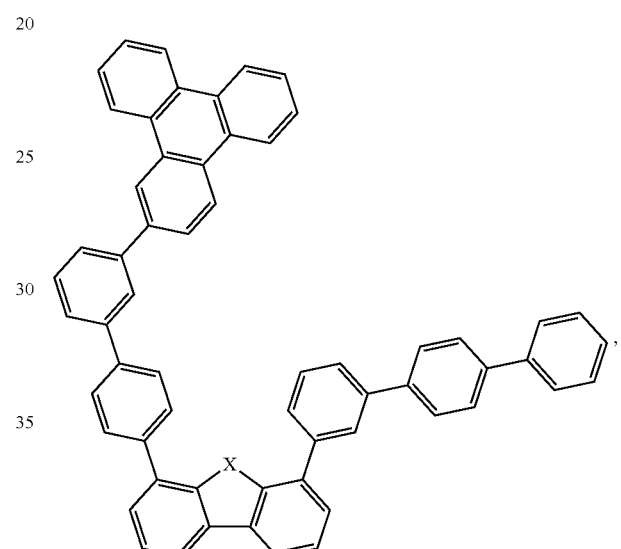

Compound 46, wherein X=O,
Compound 47, wherein X=S,
Compound 48, wherein X=Se,

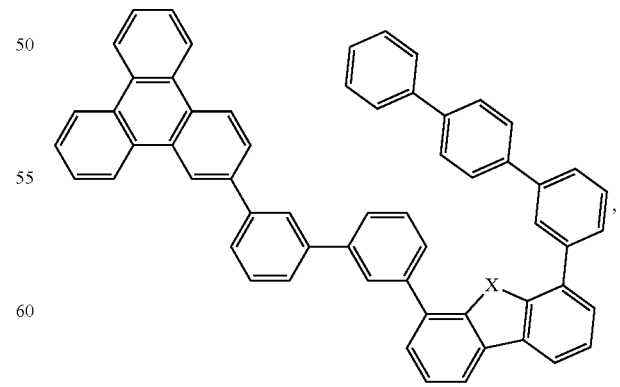

Compound 49, wherein X=O,
Compound 50, wherein X=S,
Compound 51, wherein X=Se,

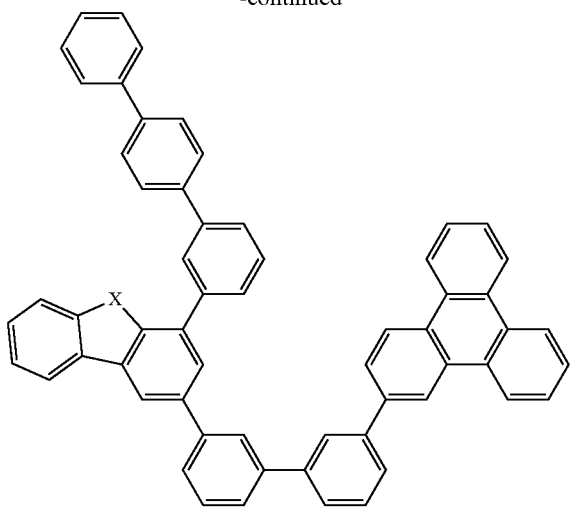

Compound 52, wherein X=O,
Compound 53, wherein X=S,
Compound 54, wherein X=Se,

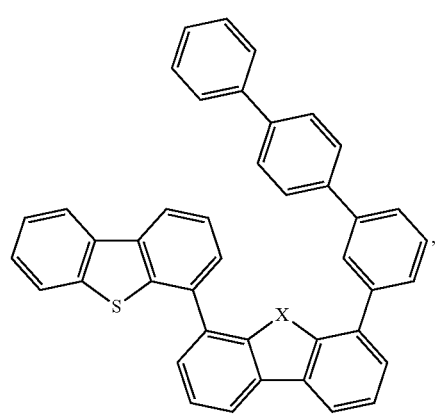

Compound 55, wherein X=O,
Compound 56, wherein X=S,
Compound 57, wherein X=Se,

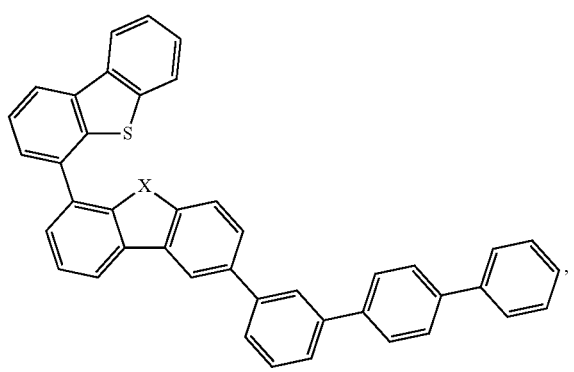

Compound 58, wherein X=O,
Compound 59, wherein X=S,
Compound 60, wherein X=Se,

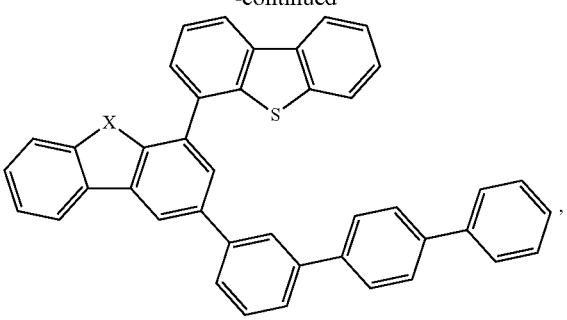

Compound 61, wherein X=O,
Compound 62, wherein X=S,
Compound 63, wherein X=Se,

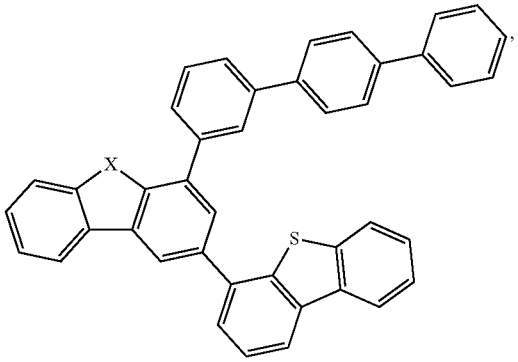

Compound 64, wherein X=O,
Compound 65, wherein X=S,
Compound 66, wherein X=Se,

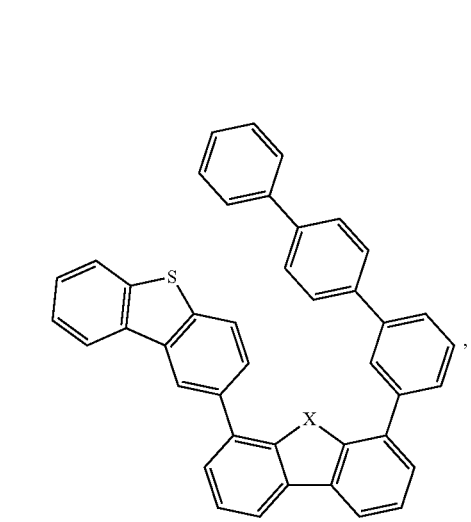

Compound 67, wherein X=O,
Compound 68, wherein X=S,
Compound 69, wherein X=Se,

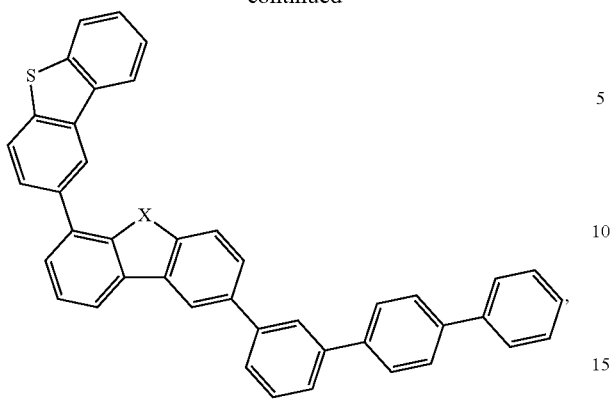

Compound 70, wherein X=O,
Compound 71, wherein X=S,
Compound 72, wherein X=Se,

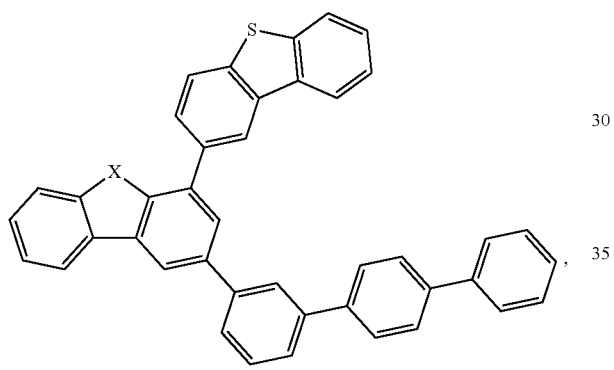

Compound 73, wherein X=O,
Compound 74, wherein X=S,
Compound 75, wherein X=Se,

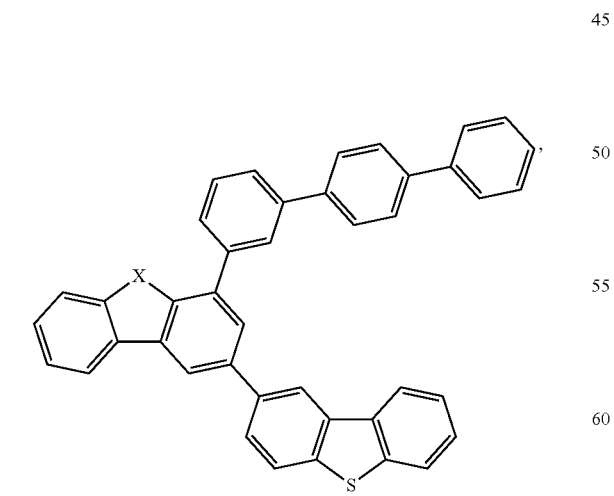

Compound 76, wherein X=O,
Compound 77, wherein X=S,
Compound 78, wherein X=Se,

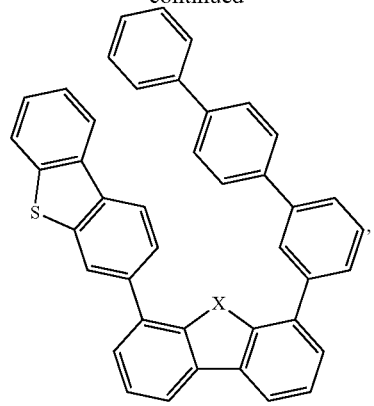

Compound 79, wherein X=O,
Compound 80, wherein X=S,
Compound 81, wherein X=Se,

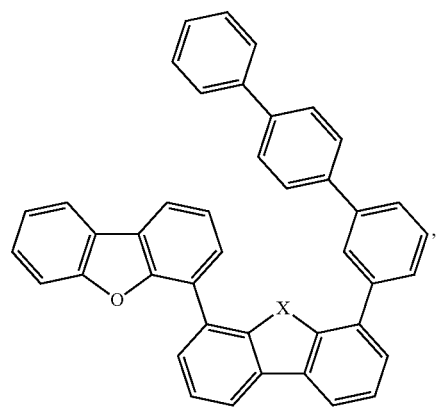

Compound 82, wherein X=O,
Compound 83, wherein X=S,
Compound 84, wherein X=Se,

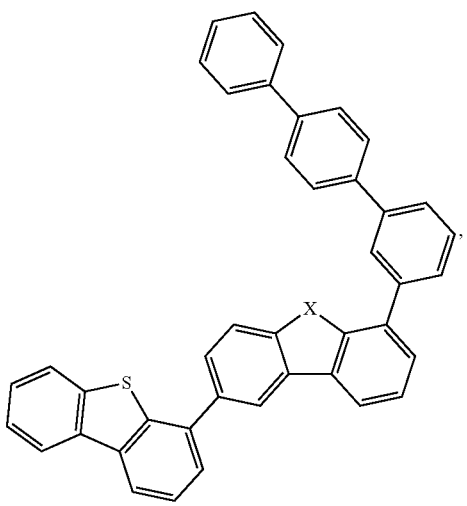

Compound 85, wherein X=O,
Compound 86, wherein X=S,
Compound 87, wherein X=Se,

-continued

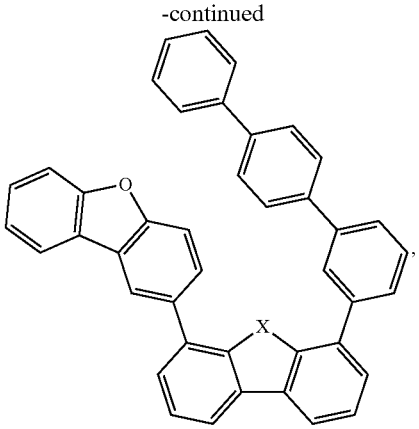

Compound 88, wherein X=O,
Compound 89, wherein X=S,
Compound 90, wherein X=Se,

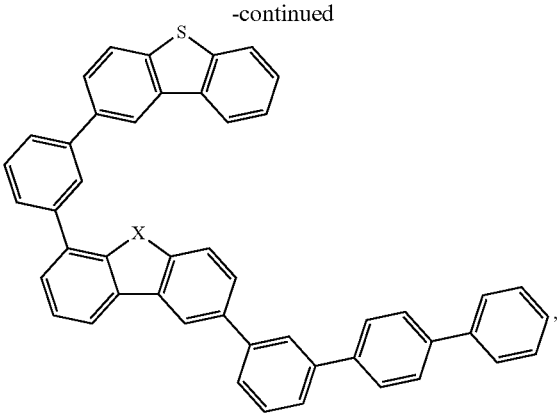

Compound 97, wherein X=O,
Compound 98, wherein X=S,
Compound 99, wherein X=Se,

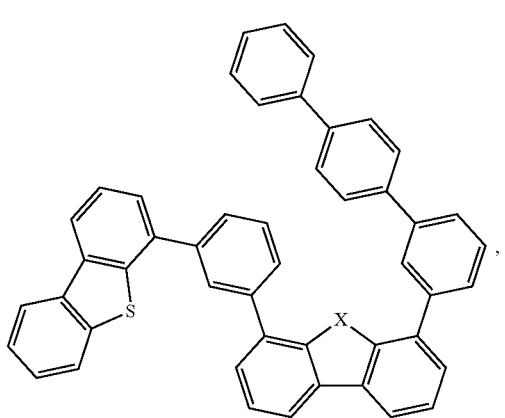

Compound 91, wherein X=O,
Compound 92, wherein X=S,
Compound 93, wherein X=Se,

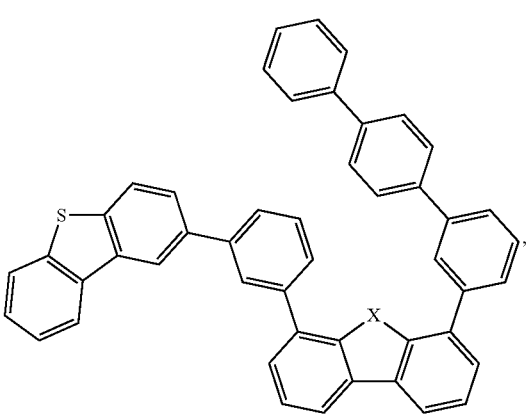

Compound 100, wherein X=O,
Compound 101, wherein X=S,
Compound 102, wherein X=Se,

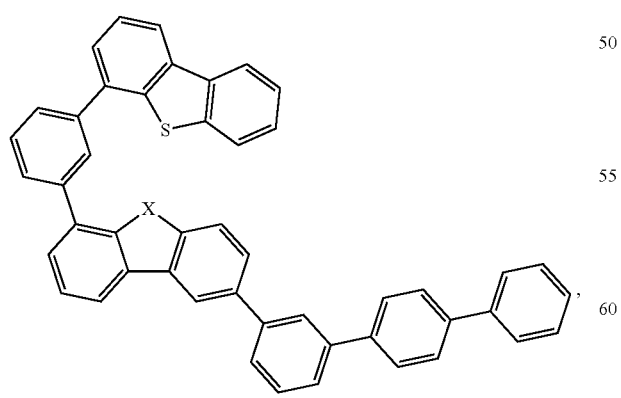

Compound 94, wherein X=O,
Compound 95, wherein X=S,
Compound 96, wherein X=Se,

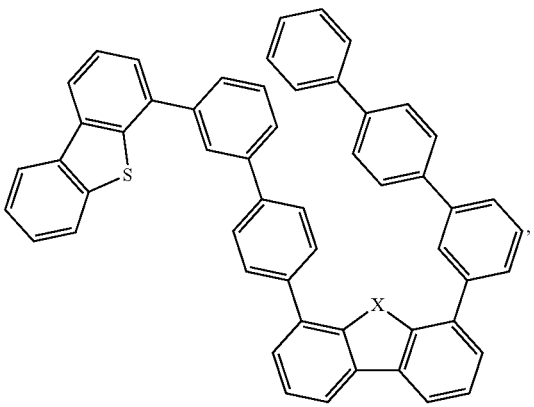

Compound 103, wherein X=O,
Compound 104, wherein X=S,
Compound 105, wherein X=Se, -continued

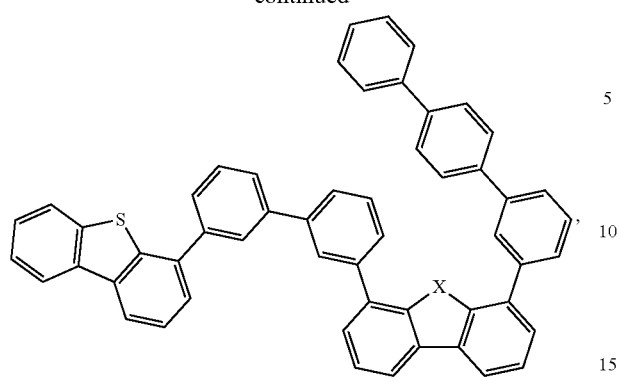

Compound 106, wherein X=O,
Compound 107, wherein X=S,
Compound 108, wherein X=Se,

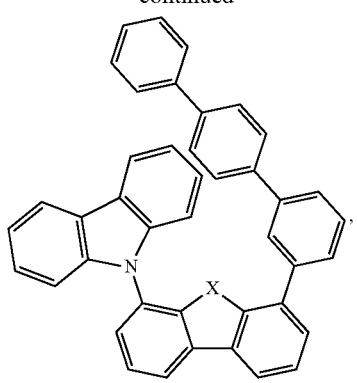

Compound 115, wherein X=O,
Compound 116, wherein X=S,
Compound 117, wherein X=Se,

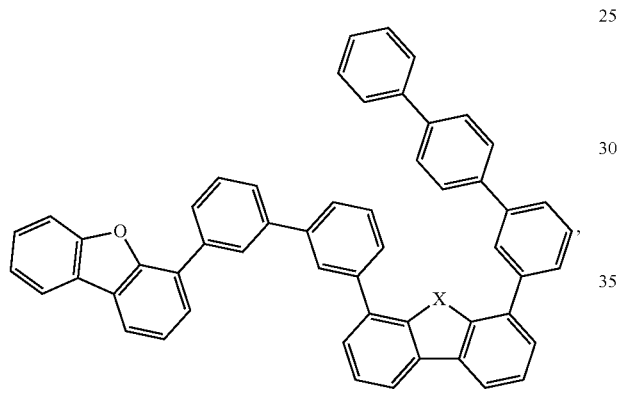

Compound 109, wherein X=O,
Compound 110, wherein X=S,
Compound 111, wherein X=Se,

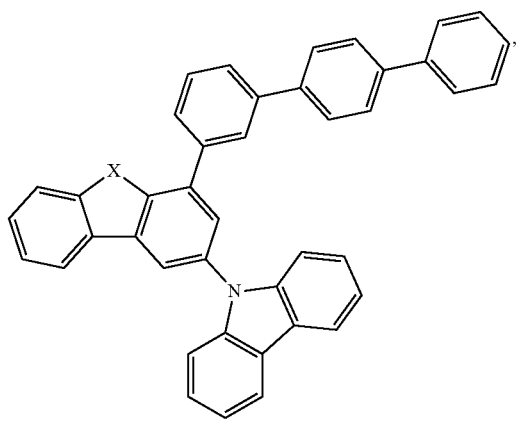

Compound 118, wherein X=O,
Compound 119, wherein X=S,
Compound 120, wherein X=Se,

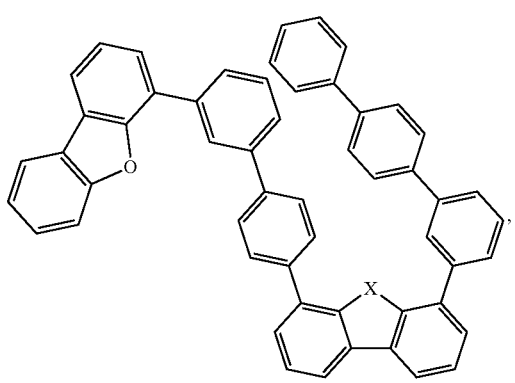

Compound 112, wherein X=O,
Compound 113, wherein X=S,
Compound 114, wherein X=Se,

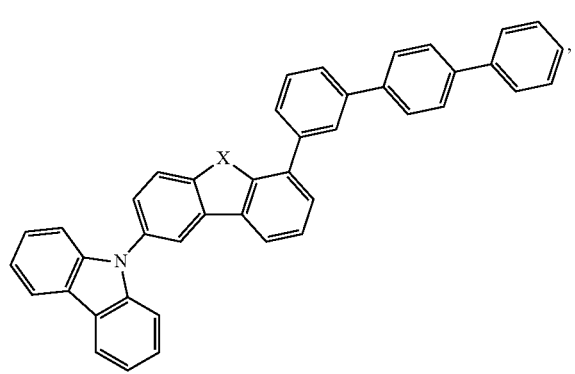

Compound 121, wherein X=O,
Compound 122, wherein X=S,
Compound 123, wherein X=Se, -continued

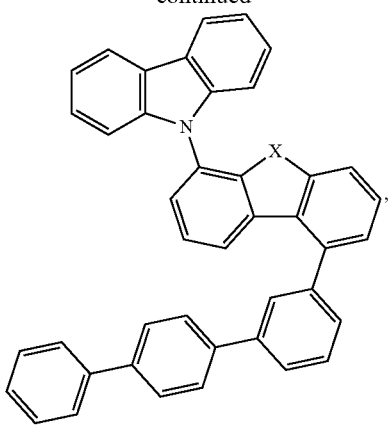

Compound 124, wherein X=O,
Compound 125, wherein X=S,
Compound 126, wherein X=Se,

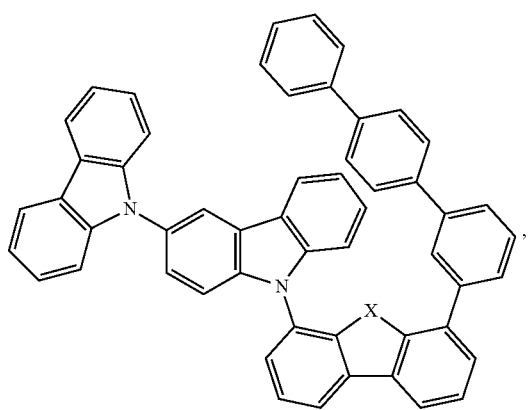

Compound 127, wherein X=O,
Compound 128, wherein X=S,
Compound 129, wherein X=Se,

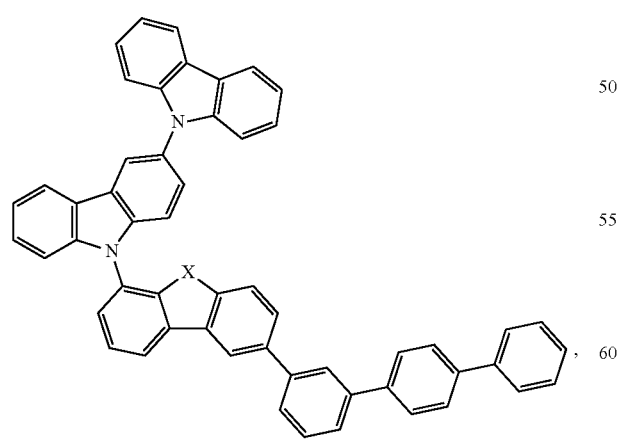

Compound 130, wherein X=O,
Compound 131, wherein X=S,
Compound 132, wherein X=Se, -continued

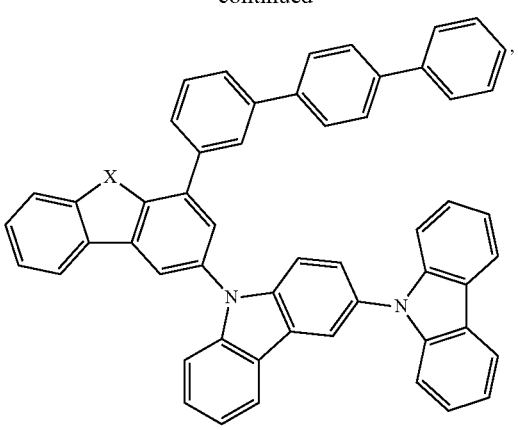

Compound 133, wherein X=O,
Compound 134, wherein X=S,
Compound 135, wherein X=Se,

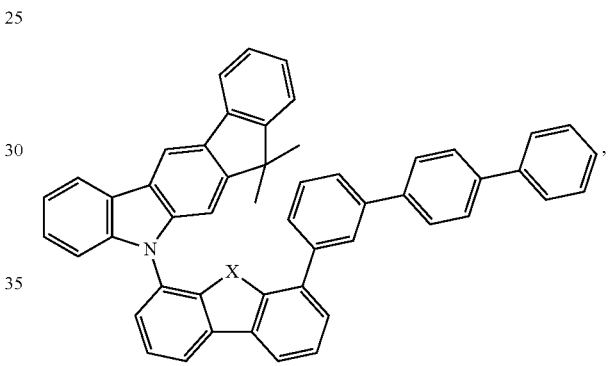

Compound 136, wherein X=O,
Compound 137, wherein X=S,
Compound 138, wherein X=Se,

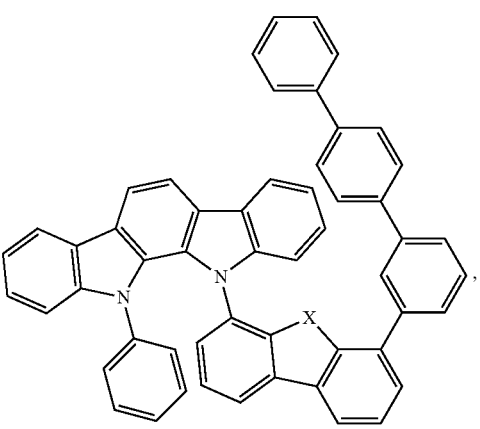

Compound 139, wherein X=O,
Compound 140, wherein X=S,
Compound 141, wherein X=Se, -continued

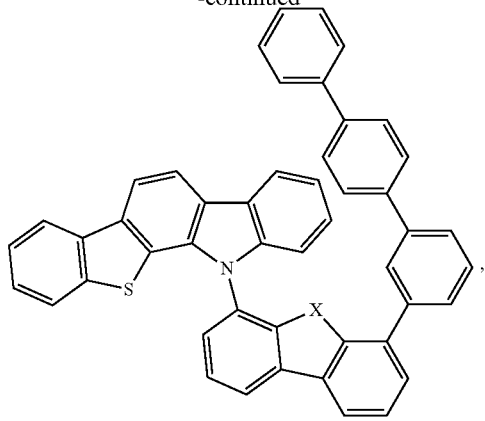

Compound 142, wherein X=O,
Compound 143, wherein X=S,
Compound 144, wherein X=Se,

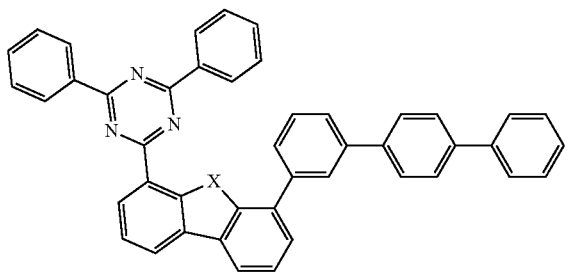

Compound 145, wherein X=O,
Compound 146, wherein X=S,
Compound 147, wherein X=Se,

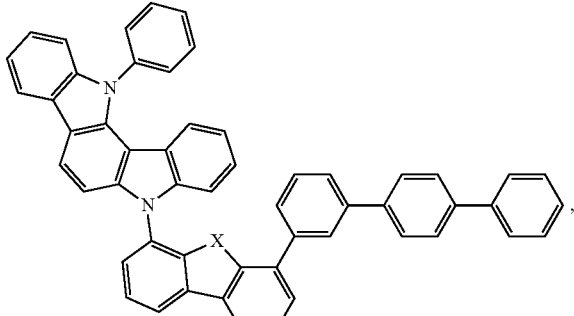

Compound 148, wherein X=O,
Compound 149, wherein X=S,
Compound 150, wherein X=Se,

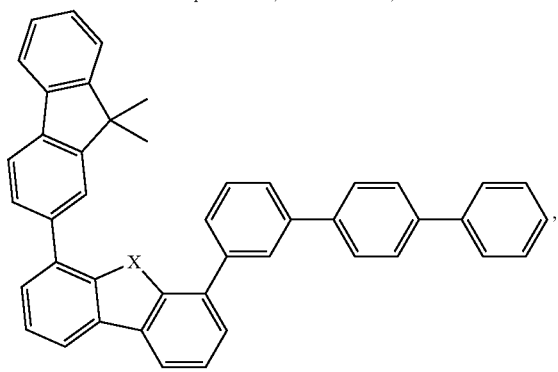

Compound 151, wherein X=O,
Compound 152, wherein X=S,
Compound 153, wherein X=Se, -continued

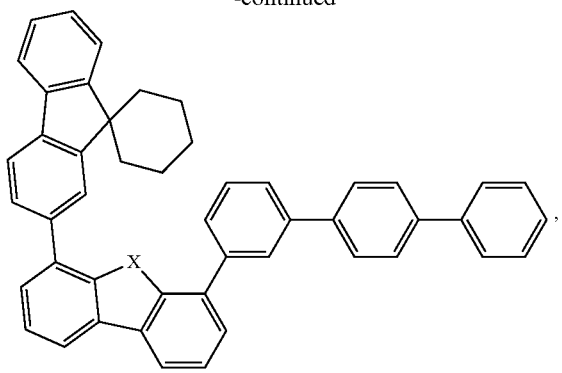

Compound 154, wherein X=O,
Compound 155, wherein X=S,
Compound 156, wherein X=Se, and

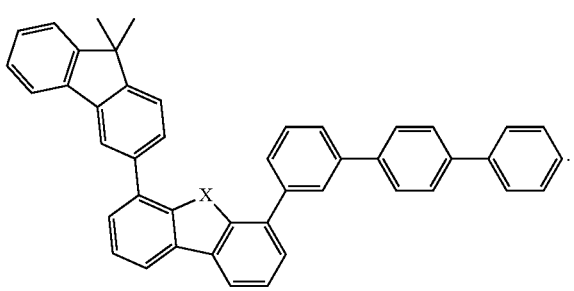

Compound 157, wherein X=O,
Compound 158, wherein X=S,
Compound 159, wherein X=Se, 7. A first device comprising a first phosphorescent organic light-emitting device, the phosphorescent organic light-emitting device comprising:
an anode;
a cathode; and
an organic layer, disposed between the anode and the cathode, comprising a compound having a formula (I)

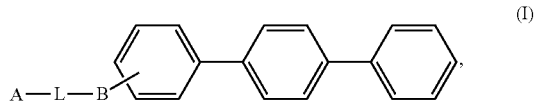

(I)

wherein A is selected from a group consisting of triphenylene, phenanthrene, anthracene, biphenyl, terphenyl, carbazole, dibenzothiophene, dibenzofuran, dibenzoselenophene, fluorene, azatriphenylene, azacarbazole, azadibenzothiophene, azadibenzofuran, azadibenzoselenophene, triazine, or combinations thereof;
wherein L is selected from a group consisting of a direct bond, benzene, biphenyl and terphenyl, pyridine, or combinations thereof, and wherein L is optionally further substituted with alkyl, halogen, hydrogen, deuterium, nitrile or aryl;
wherein B is selected from a group consisting of dibenzothiophene, dibenzofuran and dibenzoselenophene; and
wherein A and B are independently optionally further substituted with one or more substituents selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and for each of A and B, two adjacent substituents are optionally joined to form a fused ring.

8. The first device of claim 7, wherein the compound is of formula (II)

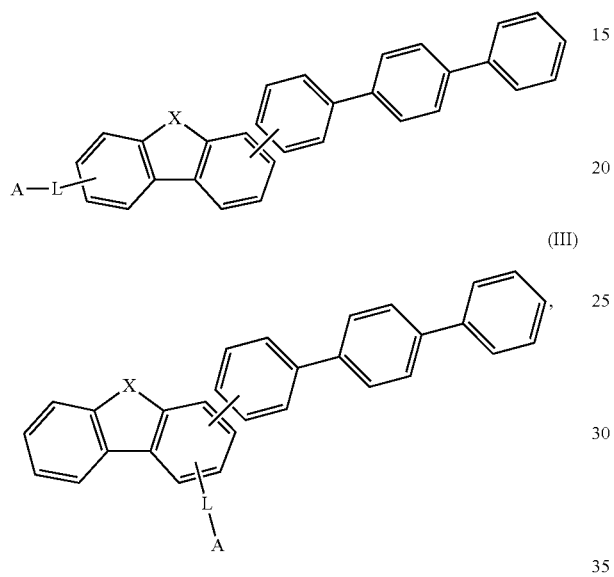

(II) or formula (III)

wherein X is selected from a group consisting of O, S and Se.

9. The first device of claim 7, wherein A is selected from the group consisting of

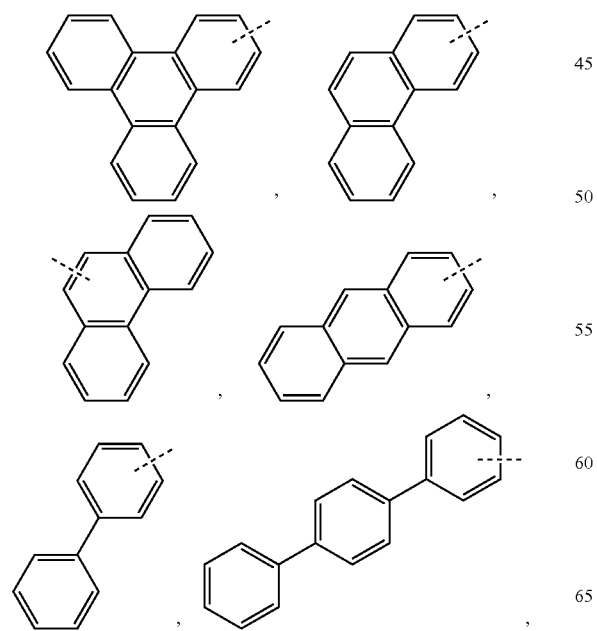

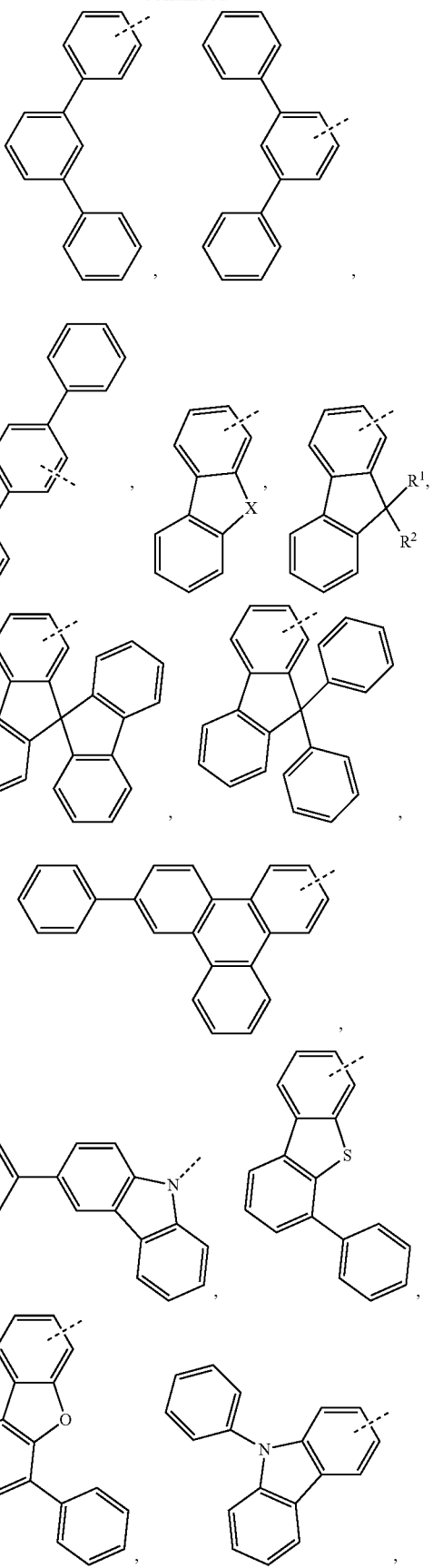

-continued
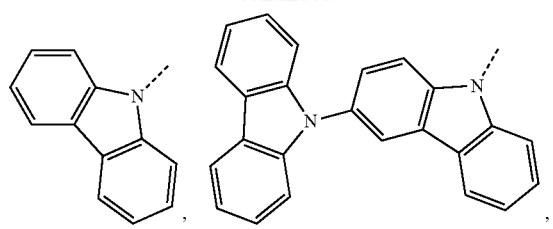
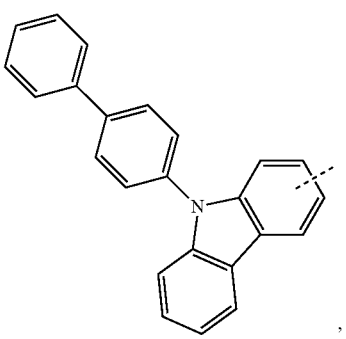
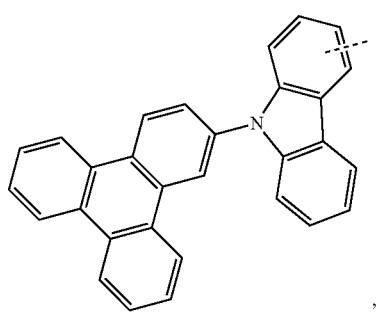
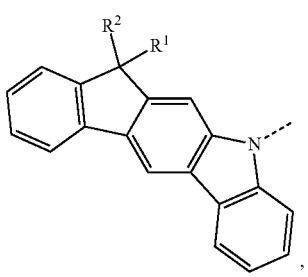
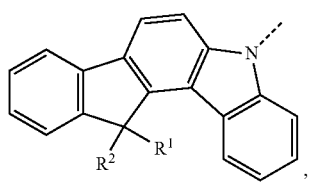
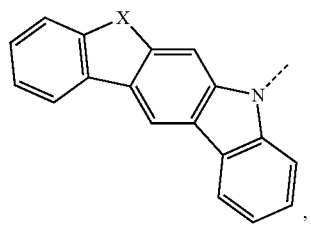
-continued
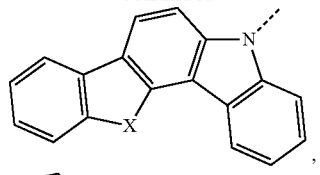
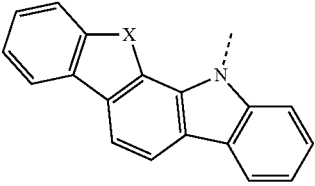
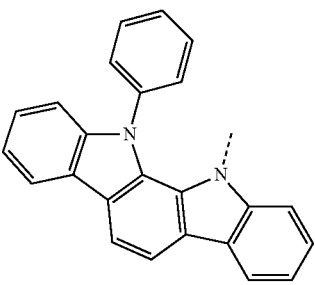
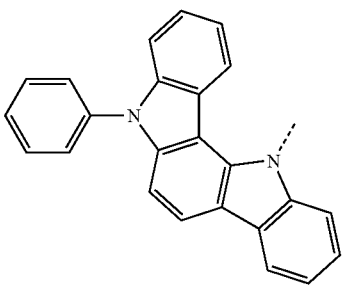
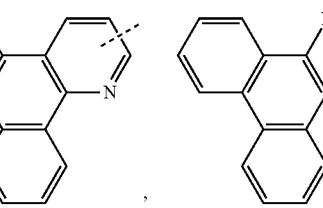
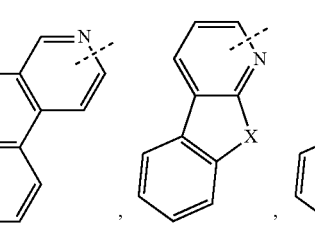
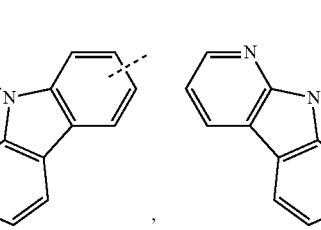
and

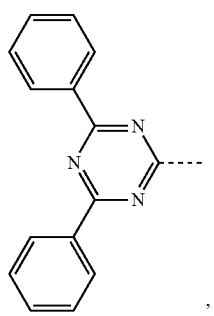

wherein X is S, O or Se; and

R$^1$ and R$^2$ are, independently, linear or branched alkyl with 1 to 12 carbon atoms, and R$^1$ and R$^2$ are optionally jointed to form a ring.

10. The first device of claim 7, wherein B is selected from the group consisting of

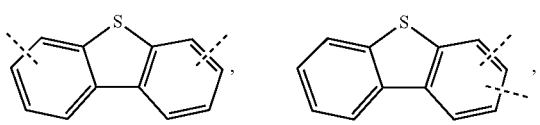

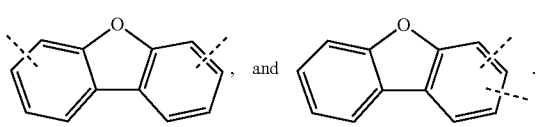

11. The first device of claim 7, wherein L is selected from the group consisting of a direct bond,

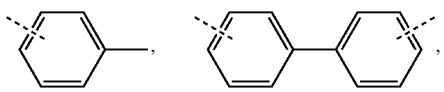

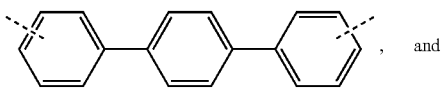

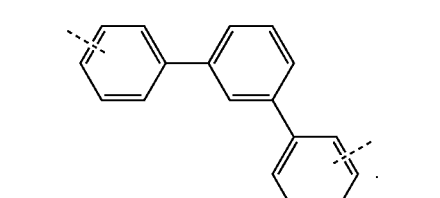

12. The first device of claim 7, wherein the compound is selected from the group consisting of

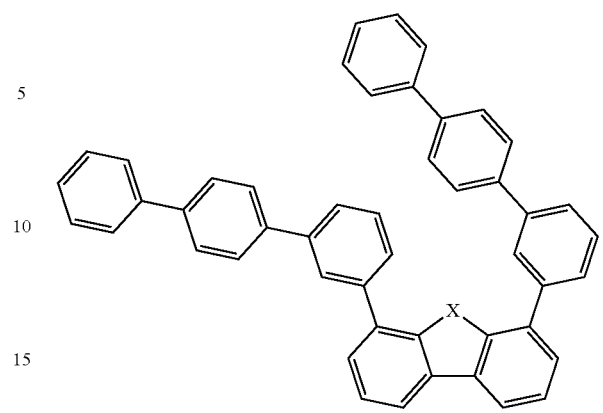

Compound 1, wherein X = O,
Compound 2, wherein X = S,
Compound 3, wherein X = Se,

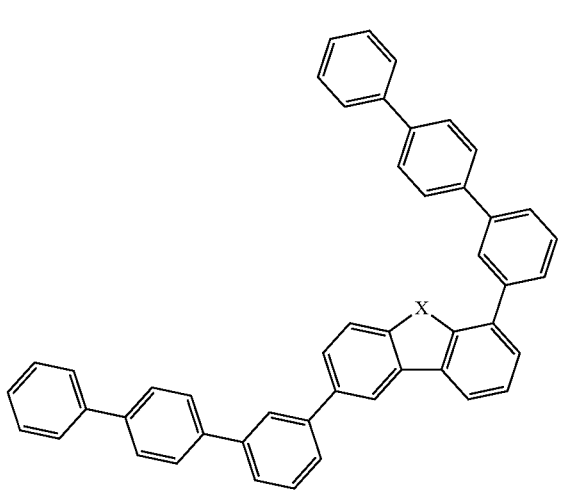

Compound 4, wherein X = O,
Compound 5, wherein X = S,
Compound 6, wherein X = Se,

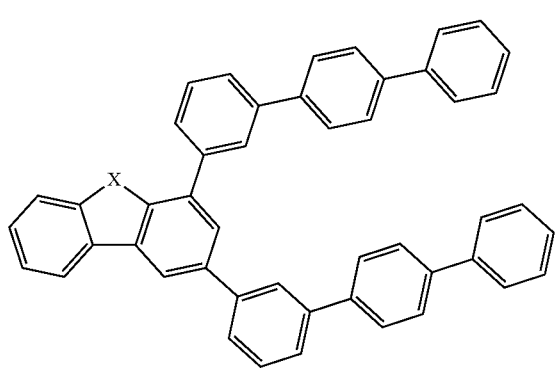

Compound 7, wherein X = O,
Compound 8, wherein X = S,
Compound 9, wherein X = Se, -continued

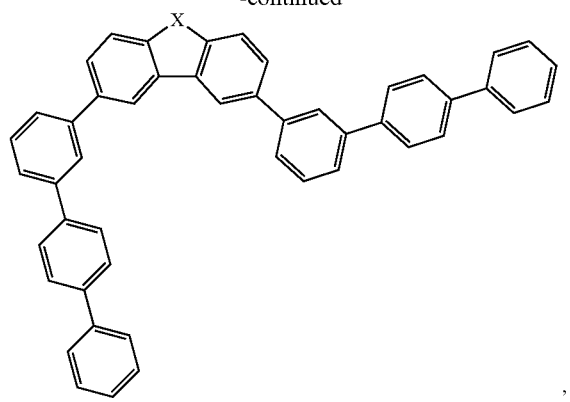

Compound 10, wherein X = O,
Compound 11, wherein X = S,
Compound 12, wherein X = Se,

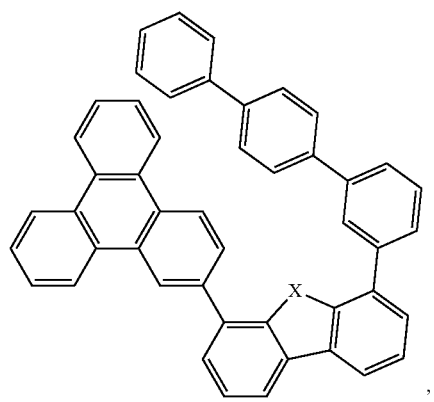

Compound 13, wherein X = O,
Compound 14, wherein X = S,
Compound 15, wherein X = Se,

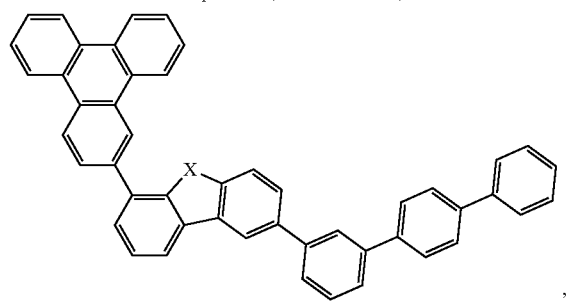

Compound 16, wherein X = O,
Compound 17, wherein X = S,
Compound 18, wherein X = Se,

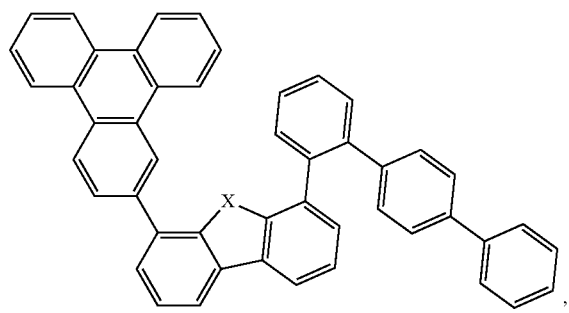

Compound 19, wherein X = O,
Compound 20, wherein X = S,
Compound 21, wherein X = Se, -continued

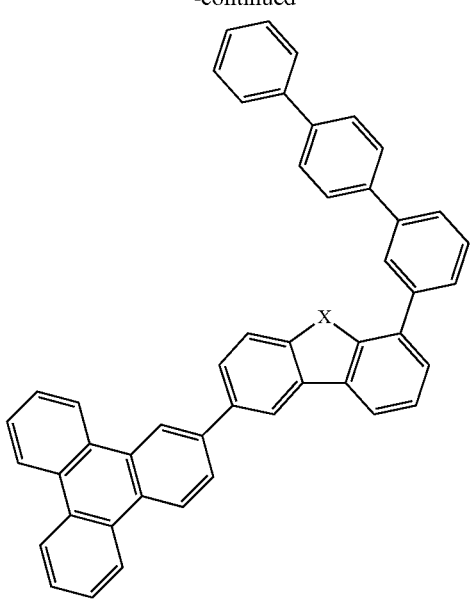

Compound 22, wherein X = O,
Compound 23, wherein X = S,
Compound 24, wherein X = Se,

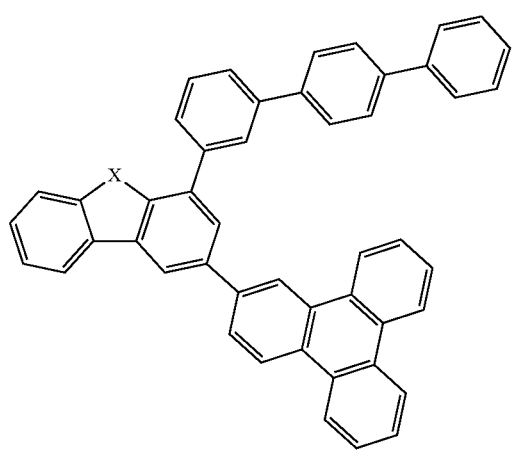

Compound 25, wherein X = O,
Compound 26, wherein X = S,
Compound 27, wherein X = Se,

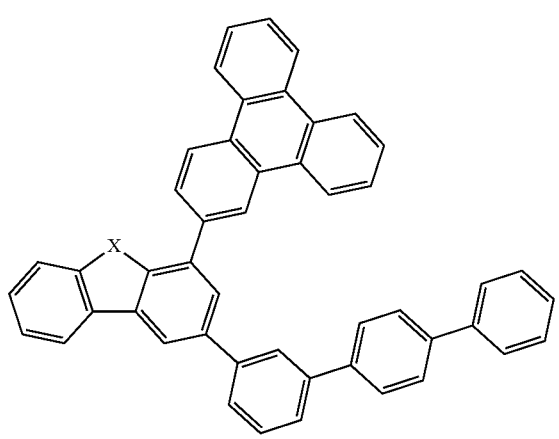

Compound 28, wherein X = O,
Compound 29, wherein X = S,
Compound 30, wherein X = Se,

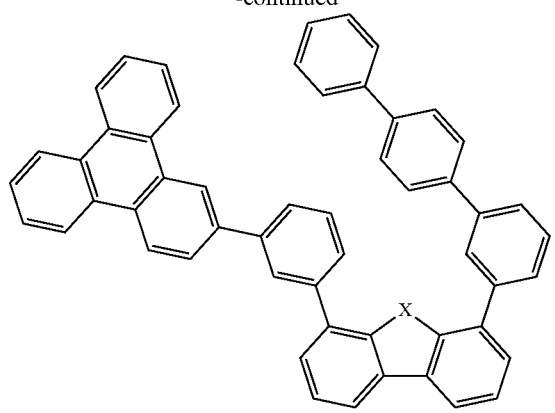

Compound 31, wherein X = O,
Compound 32, wherein X = S,
Compound 33, wherein X = Se,

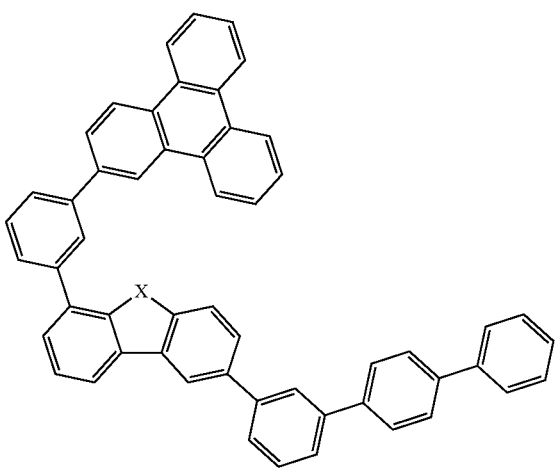

Compound 34, wherein X = O,
Compound 35, wherein X = S,
Compound 36, wherein X = Se,

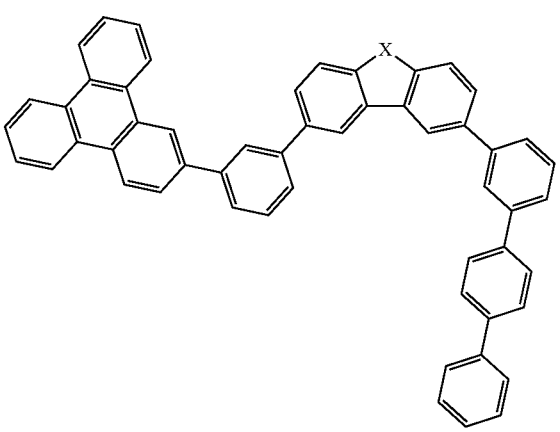

Compound 37, wherein X = O,
Compound 38, wherein X = S,
Compound 39, wherein X = Se,

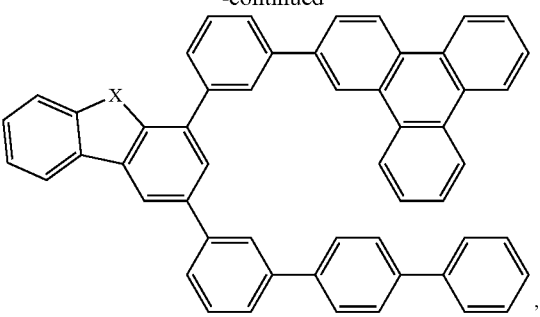

Compound 40, wherein X = O,
Compound 41, wherein X = S,
Compound 42, wherein X = Se,

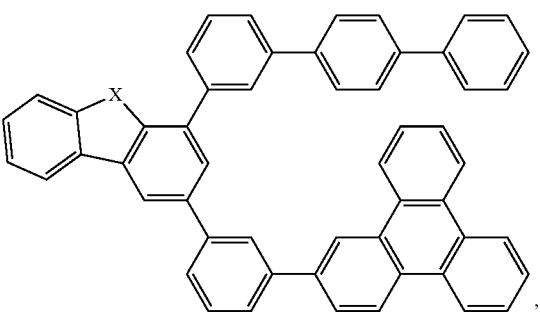

Compound 43, wherein X = O,
Compound 44, wherein X = S,
Compound 45, wherein X = Se,

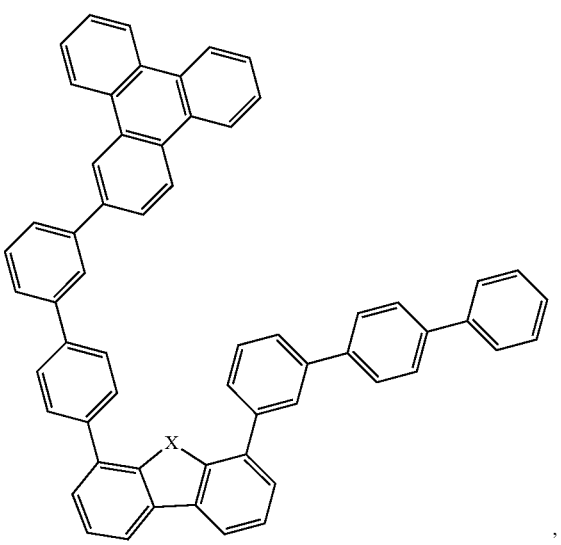

Compound 46, wherein X = O,
Compound 47, wherein X = S,
Compound 48, wherein X = Se,

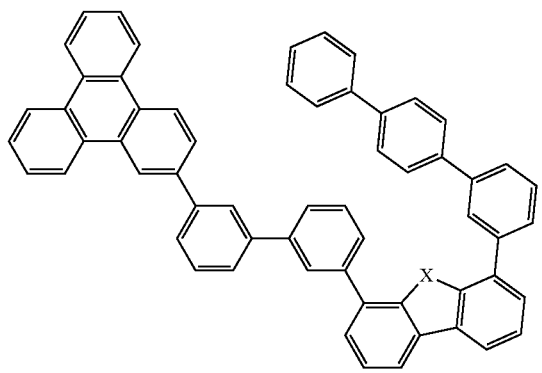

Compound 49, wherein X = O,
Compound 50, wherein X = S,
Compound 51, wherein X = Se,

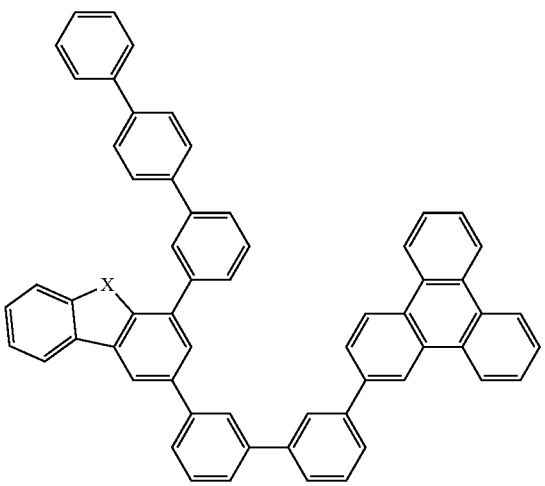

Compound 52, wherein X = O,
Compound 53, wherein X = S,
Compound 54, wherein X = Se,

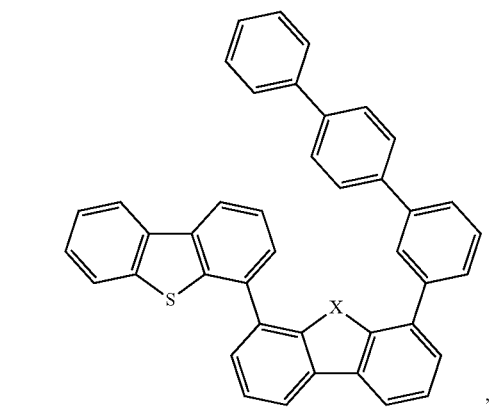

Compound 55, wherein X = O,
Compound 56, wherein X = S,
Compound 57, wherein X = Se,

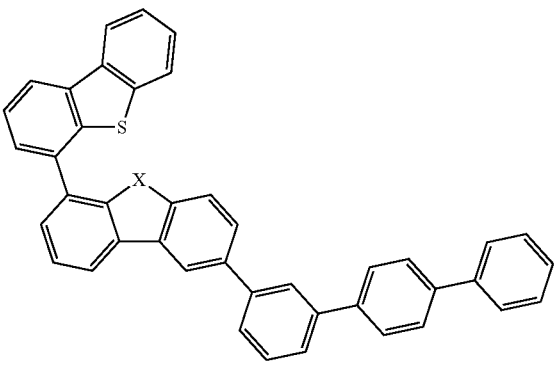

Compound 58, wherein X = O,
Compound 59, wherein X = S,
Compound 60, wherein X = Se,

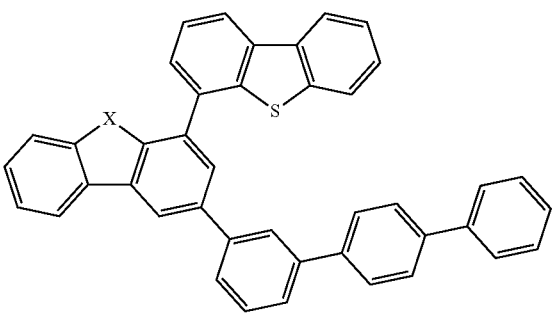

Compound 61, wherein X = O,
Compound 62, wherein X = S,
Compound 63, wherein X = Se,

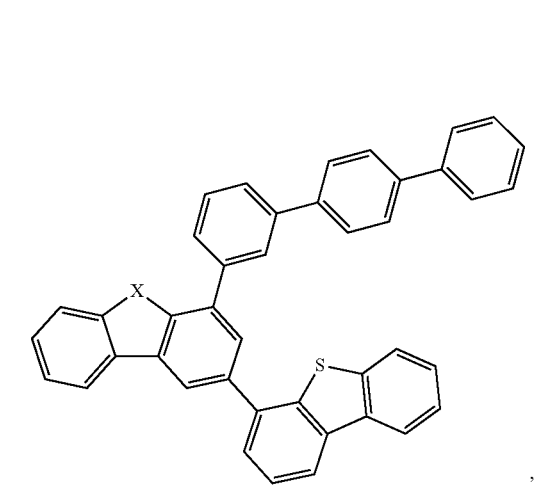

Compound 64, wherein X = O,
Compound 65, wherein X = S,
Compound 66, wherein X = Se,

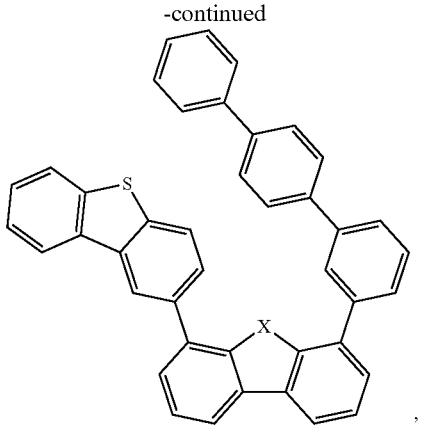

Compound 67, wherein X = O,
Compound 68, wherein X = S,
Compound 69, wherein X = Se,

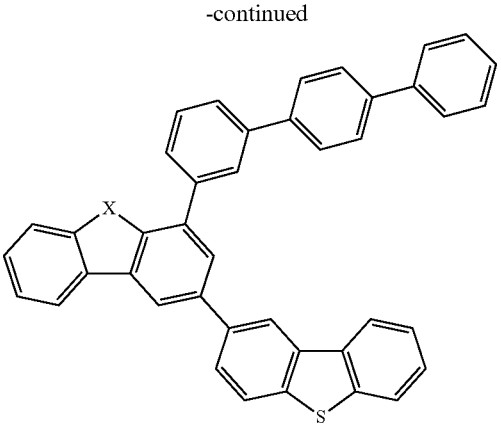

Compound 76, wherein X = O,
Compound 77, wherein X = S,
Compound 78, wherein X = Se,

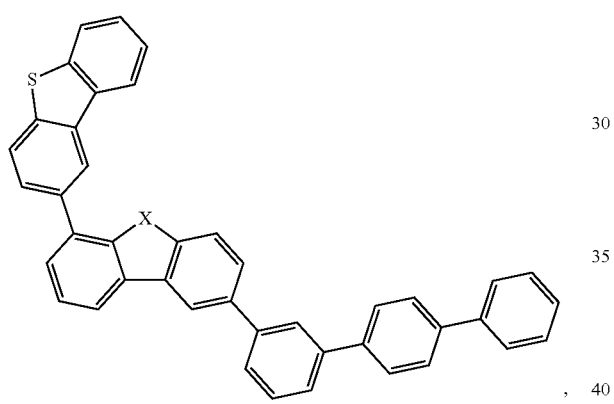

Compound 70, wherein X = O,
Compound 71, wherein X = S,
Compound 72, wherein X = Se,

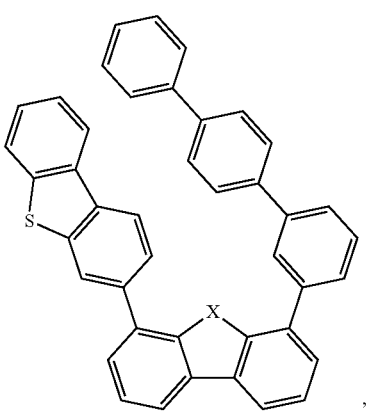

Compound 79, wherein X = O,
Compound 80, wherein X = S,
Compound 81, wherein X = Se,

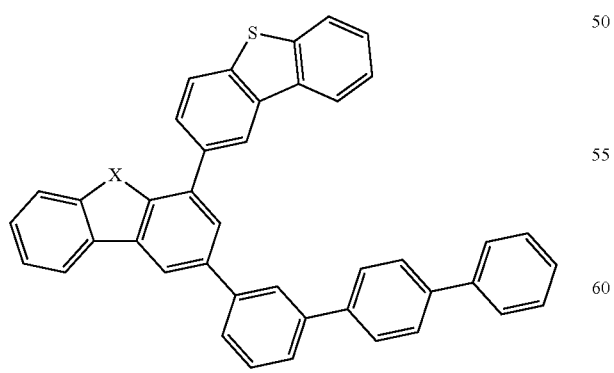

Compound 73, wherein X = O,
Compound 74, wherein X = S,
Compound 75, wherein X = Se,

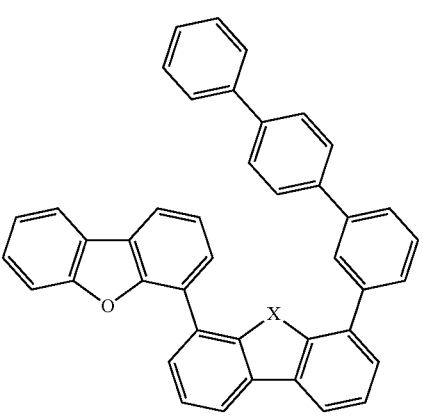

Compound 82, wherein X = O,
Compound 83, wherein X = S,
Compound 84, wherein X = Se,

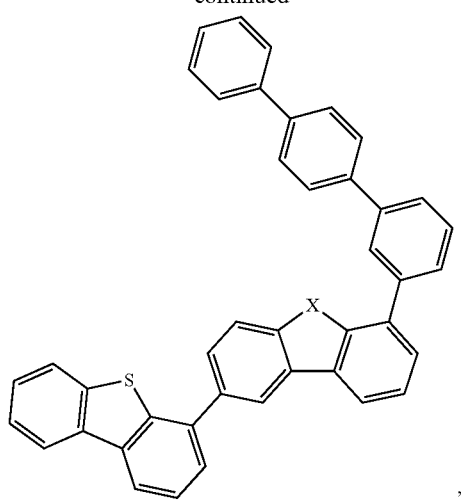

Compound 85, wherein X = O,
Compound 86, wherein X = S,
Compound 87, wherein X = Se,

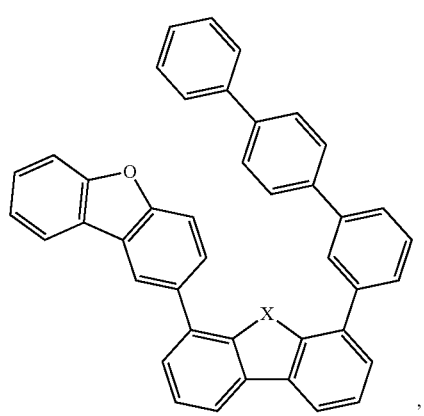

Compound 88, wherein X = O,
Compound 89, wherein X = S,
Compound 90, wherein X = Se,

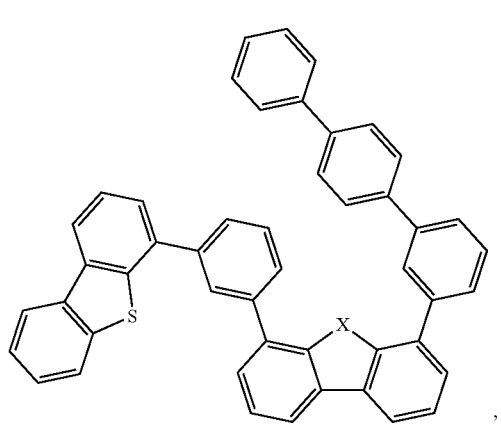

Compound 91, wherein X = O,
Compound 92, wherein X = S,
Compound 93, wherein X = Se,

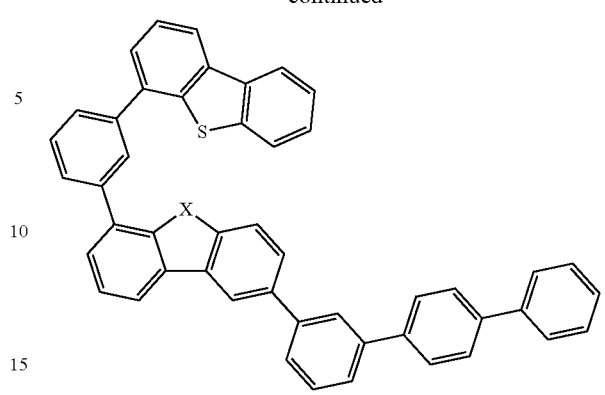

Compound 94, wherein X = O,
Compound 95, wherein X = S,
Compound 96, wherein X = Se,

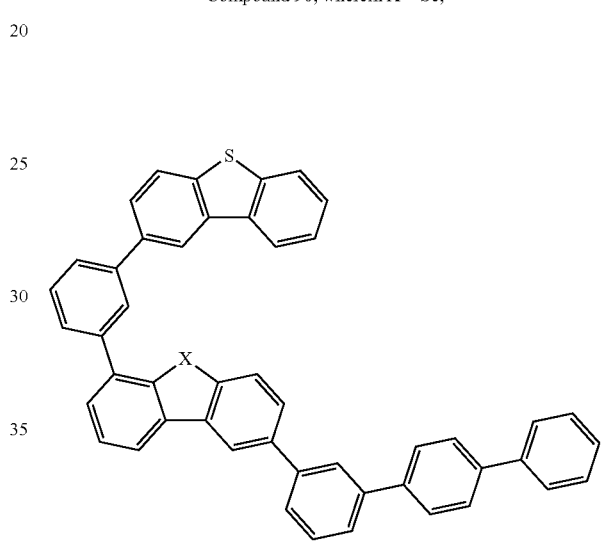

Compound 97, wherein X = O,
Compound 98, wherein X = S,
Compound 99, wherein X = Se,

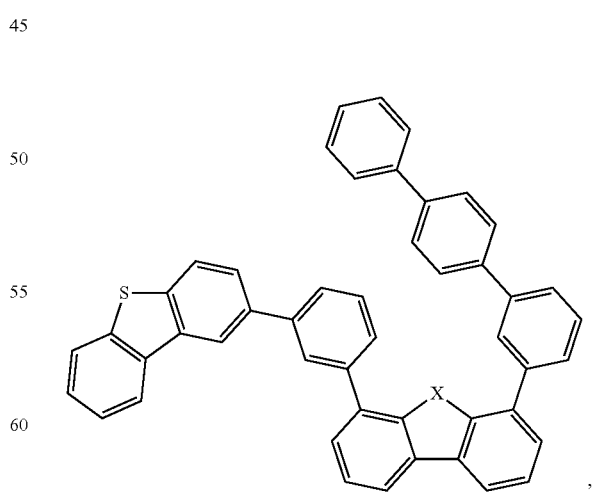

Compound 100, wherein X = O,
Compound 101, wherein X = S,
Compound 102, wherein X = Se,

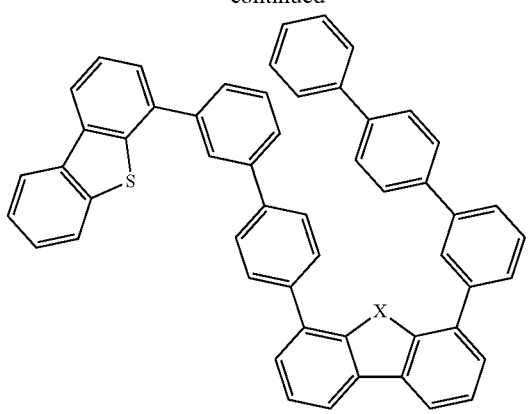

Compound 103, wherein X = O,
Compound 104, wherein X = S,
Compound 105, wherein X = Se,

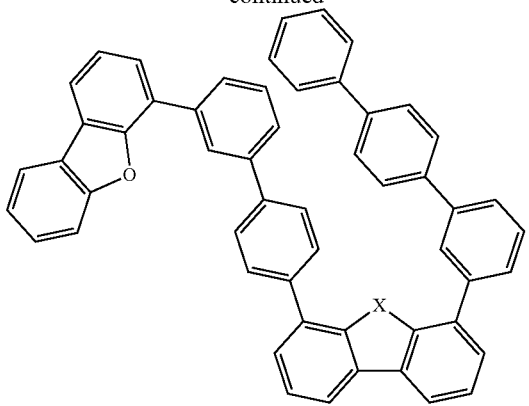

Compound 112, wherein X = O,
Compound 113, wherein X = S,
Compound 114, wherein X = Se,

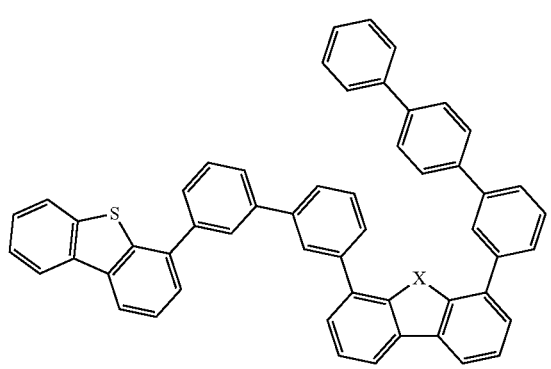

Compound 106, wherein X = O,
Compound 107, wherein X = S,
Compound 108, wherein X = Se,

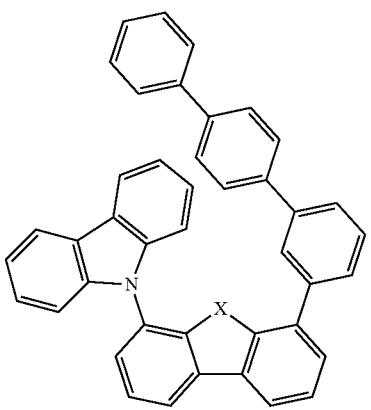

Compound 115, wherein X = O,
Compound 116, wherein X = S,
Compound 117, wherein X = Se,

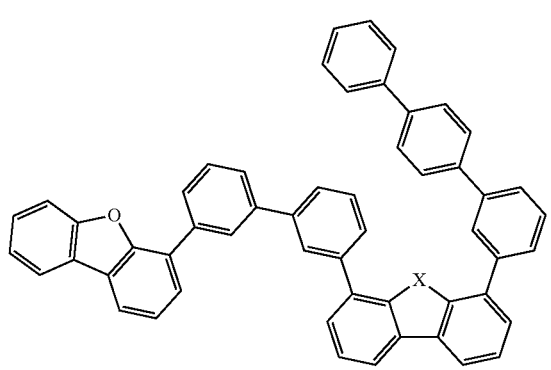

Compound 109, wherein X = O,
Compound 110, wherein X = S,
Compound 111, wherein X = Se,

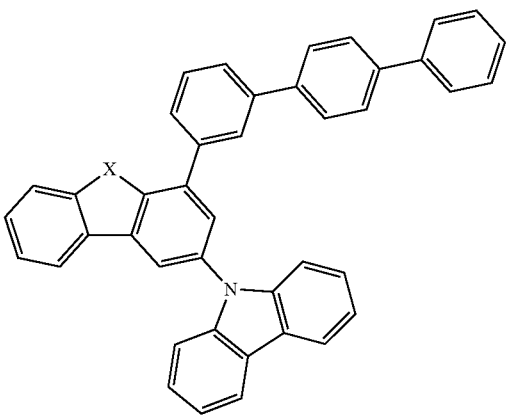

Compound 118, wherein X = O,
Compound 119, wherein X = S,
Compound 120, wherein X = Se,

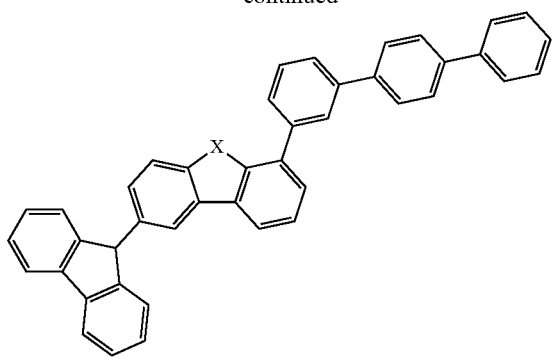

Compound 121, wherein X = O,
Compound 122, wherein X = S,
Compound 123, wherein X = Se,

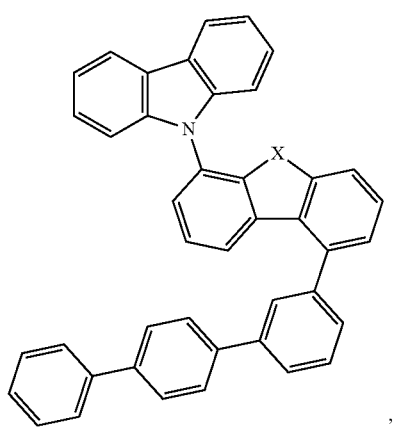

Compound 124, wherein X = O,
Compound 125, wherein X = S,
Compound 126, wherein X = Se,

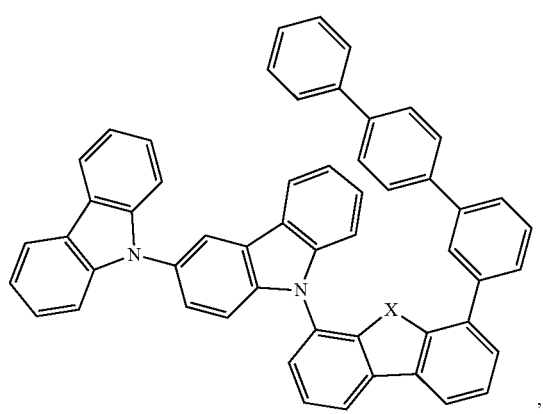

Compound 127, wherein X = O,
Compound 128, wherein X = S,
Compound 129, wherein X = Se,

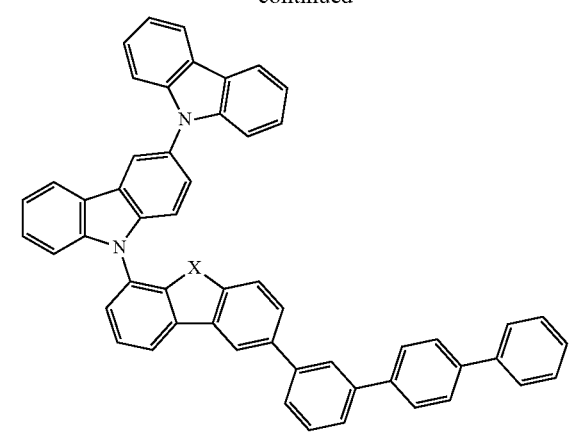

Compound 130, wherein X = O,
Compound 131, wherein X = S,
Compound 132, wherein X = Se,

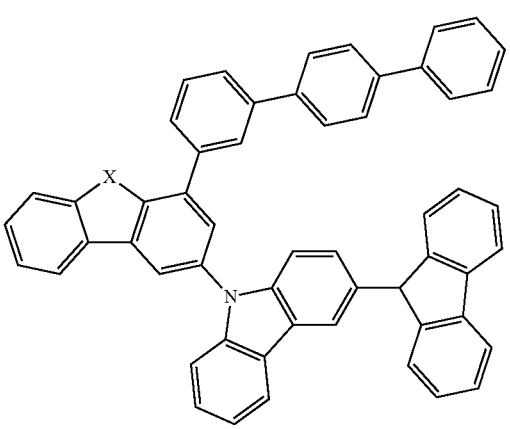

Compound 133, wherein X = O,
Compound 134, wherein X = S,
Compound 135, wherein X = Se,

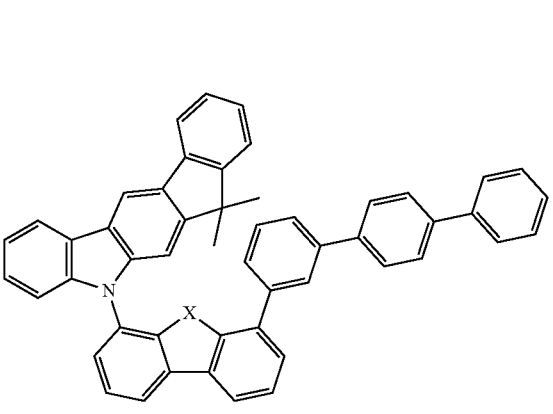

Compound 136, wherein X = O,
Compound 137, wherein X = S,
Compound 138, wherein X = Se, -continued

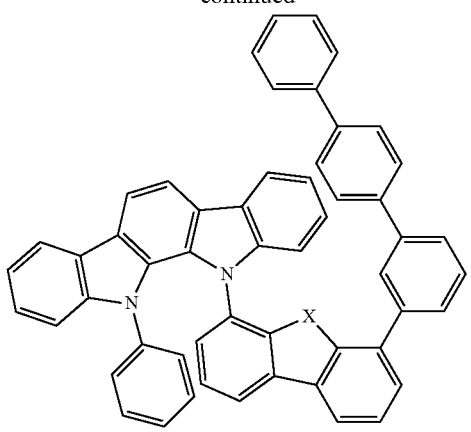

Compound 139, wherein X = O,
Compound 140, wherein X = S,
Compound 141, wherein X = Se,

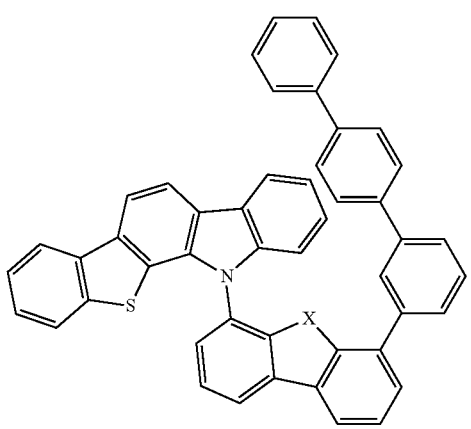

Compound 142, wherein X = O,
Compound 143, wherein X = S,
Compound 144, wherein X = Se,

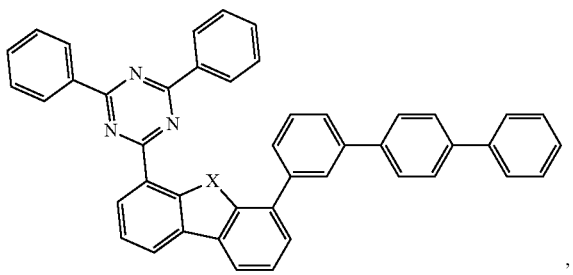

Compound 145, wherein X = O,
Compound 146, wherein X = S,
Compound 147, wherein X = Se, -continued

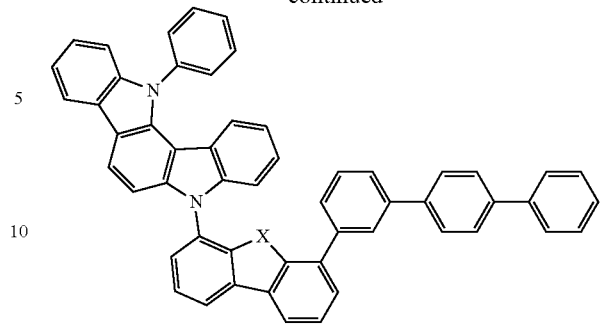

Compound 148, wherein X = O,
Compound 149, wherein X = S,
Compound 150, wherein X = Se,

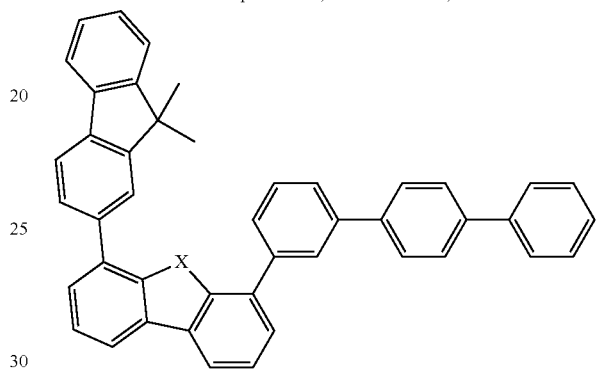

Compound 151, wherein X = O,
Compound 152, wherein X = S,
Compound 153, wherein X = Se,

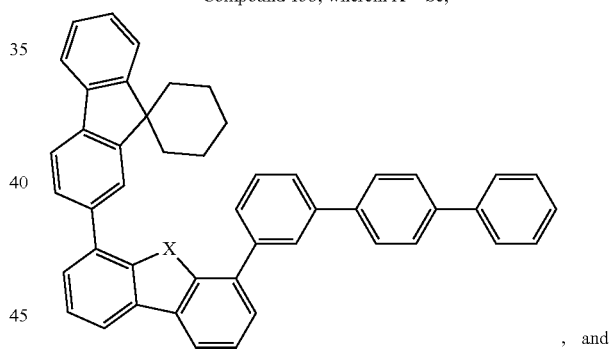

Compound 154, wherein X = O,
Compound 155, wherein X = S,
Compound 156, wherein X = Se,

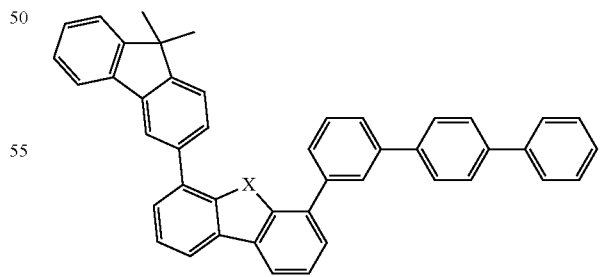

Compound 157, wherein X = O,
Compound 158, wherein X = S,
Compound 159, wherein X = Se,

13. The first device of claim 7, wherein the organic layer is an emissive layer and the compound of the formula (I) is a host.

14. The first device of claim 7, wherein the organic layer further comprising a phosphorescent emissive dopant.
15. The first device of claim 14, wherein the phosphorescent emissive dopant is a transition metal complex having at least one ligand selected from the group consisting of:
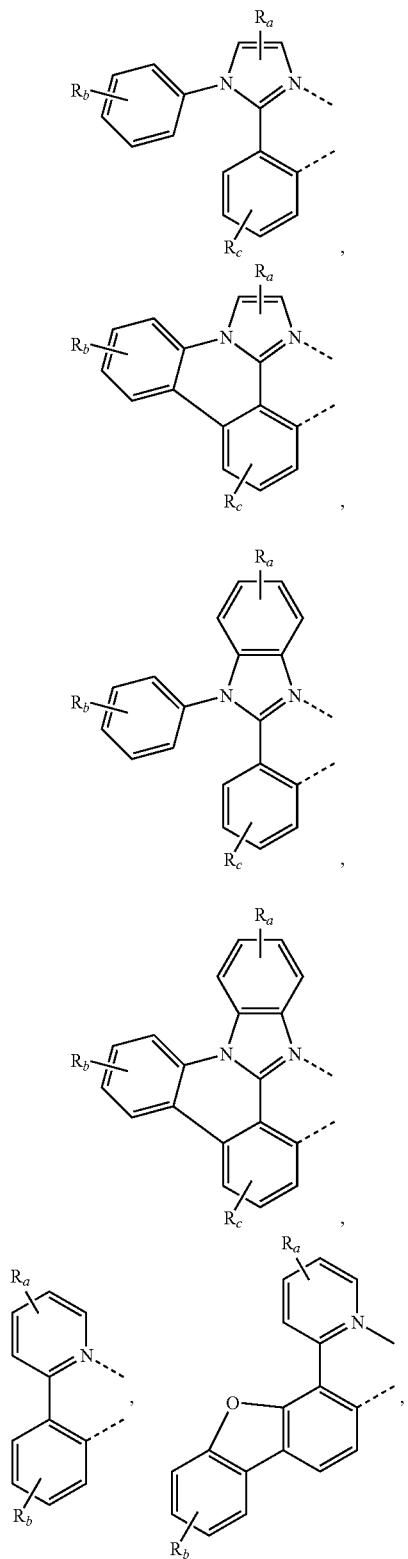
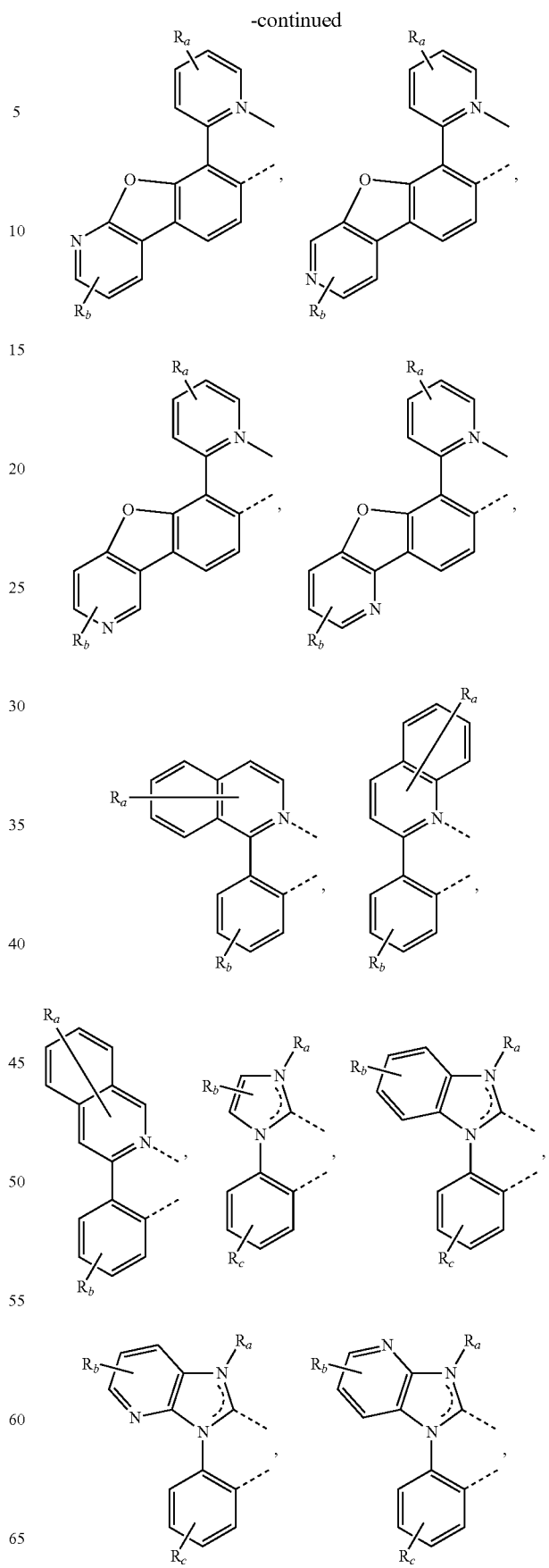

-continued

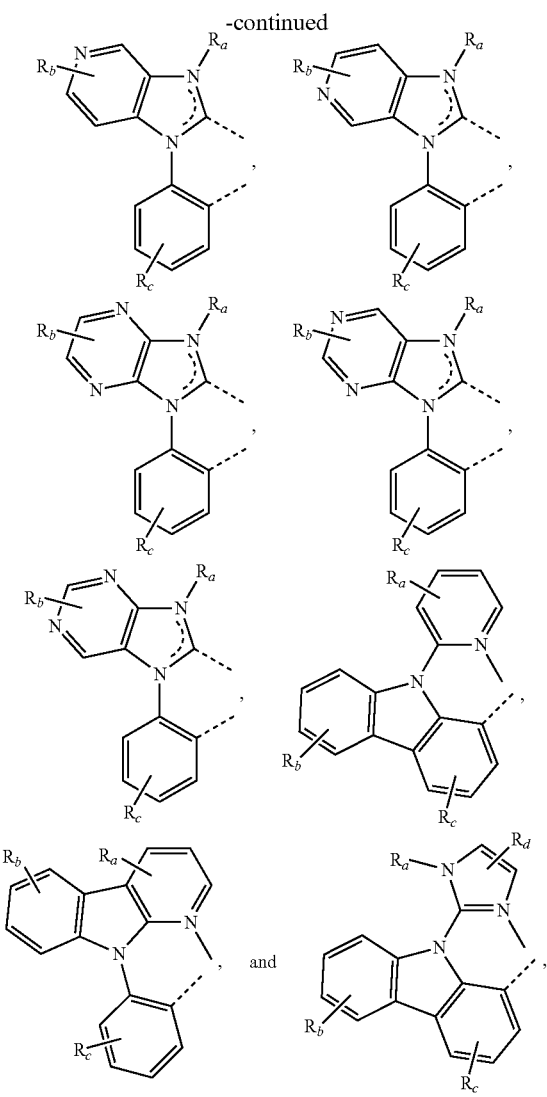

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

16. The first device of claim 7, wherein the organic layer is a blocking layer and the compound of the formula (I) is a blocking material in the organic layer.

17. The first device of claim 7, wherein the organic layer is an electron transporting layer and the compound of the formula (I) is an electron transporting material in the organic layer.

18. The first device of claim 7, wherein the first device is a consumer product.

19. The first device of claim 7, wherein the first device is an organic light-emitting device.

20. The first device of claim 7, wherein the first device comprises a lighting panel.

21. A formulation comprising the compound having a structure according to a formula (I)

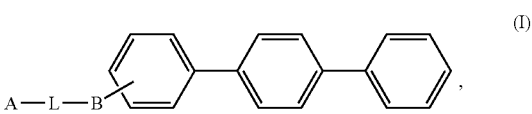
(I)

wherein A is selected from a group consisting of triphenylene, phenanthrene, anthracene, biphenyl, terphenyl, carbazole, dibenzothiophene, dibenzofuran, dibenzoselenophene, fluorene, azatriphenylene, azacarbazole, azadibenzothiophene, azadibenzofuran, azadibenzoselenophene, triazine, or combinations thereof;

wherein L is selected from a group consisting of a direct bond, benzene, biphenyl and terphenyl, pyridine, or combinations thereof, and wherein L is optionally further substituted with alkyl, halogen, hydrogen, deuterium, nitrile or aryl;

wherein B is selected from a group consisting of dibenzothiophene, dibenzofuran and dibenzoselenophene; and wherein A and B are independently optionally further substituted with one or more substituents selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, sulfanyl, sulfinyl, sulfonyl, phosphino, and combinations thereof, and for each of A and B, two adjacent substituents are optionally joined to form a fused ring.

* * * * *